(12) United States Patent
Besnard et al.

(10) Patent No.: US 9,079,895 B2
(45) Date of Patent: Jul. 14, 2015

(54) MORPHOLINO COMPOUNDS, USES AND METHODS

(71) Applicant: University of Dundee, Dundee, Scotland (GB)

(72) Inventors: Jeremy Besnard, Dundee (GB);
Andrew Lee Hopkins, Dundee (GB);
Ian Gilbert, Dundee (GB); Gian Filippo Ruda, Oxford (GB); Keren Abecassis, Cambridge (GB)

(73) Assignee: University of Dundee, Dundee, Scotland (GB)

( * ) Notice: Subject to any disclaimer, the term of this patent is extended or adjusted under 35 U.S.C. 154(b) by 0 days.

(21) Appl. No.: 14/085,714

(22) Filed: Nov. 20, 2013

(65) Prior Publication Data

US 2014/0148452 A1    May 29, 2014

Related U.S. Application Data

(63) Continuation of application No. PCT/GB2012/051194, filed on May 25, 2012.

(51) Int. Cl.

| | |
|---|---|
| C07D 413/14 | (2006.01) |
| C07D 413/06 | (2006.01) |
| C07D 209/08 | (2006.01) |
| C07D 209/12 | (2006.01) |
| C07D 265/30 | (2006.01) |

(52) U.S. Cl.
CPC ............ *C07D 413/14* (2013.01); *C07D 209/08* (2013.01); *C07D 209/12* (2013.01); *C07D 265/30* (2013.01); *C07D 413/06* (2013.01)

(58) Field of Classification Search
CPC .. C07D 413/14; C07D 413/06; C07D 265/30; C07D 209/12; C07D 209/08
USPC ........................................ 544/143; 514/275.2
See application file for complete search history.

(56) References Cited

U.S. PATENT DOCUMENTS 6,084,098 A    7/2000    Kover et al.

FOREIGN PATENT DOCUMENTS

WO    WO 98/07710    2/1998

OTHER PUBLICATIONS

International Search Report and Written Opinion of International Application No. PCT/GB2012/051194 with a mailing date of Oct. 8, 2012.
Berg, et al.; "(R)-(+)-2-[[[3-(Morpholinomethyl)-2H-chromen-8-yl]oxy]methyl]morpholine Methanesulfonate: A New Selective Rat 5-Hydroxytryptamine$_{1B}$ Receptor Antagonist"; J. Med. Chem.; vol. 41, No. 11, pp. 1934-1942 (1998).
Database Registry [Online]; Chemical Abstracts Service, Columbus, Ohio, US; Mar. 18, 2010; Database accession No. 1211465-15-4; Chemical Catalog; Suplier: Scientific Exchange, Inc.
Gross, et al.; "Asymmetric Deprotonations: Lithiation of N-(tert-Butoxycarbonyl)indoline with sec-Butyllithium/(−)-Sparteine"; J. Org. Chem.; vol. 62, No. 22, pp. 7679-7689 (1997).
Kulagowski, et al.; "Dopamine D4 Receptor Antagonists"; Current Pharmaceutical Design; vol. 3, No. 4, pp. 355-366 (1997).
Showell, et al.; "Binding of 2, 4-disubstituted morpholines at human D$_4$ dopamine receptors"; Bioorganic & Medicinal Chemistry; vol. 6, No. 1, pp. 1-8 (1998).
Stock, et al.; "5-Lipoxygenase-activating protein inhibitors. Part 2: 3-{5-((S)-1-Acetyl-2,3-dihydro-1H-indol-2-ylmethoxy)-3-tert-butylsulfanyl-1-[4-(methoxy-pyrimidin-2-yl)-benzyl]-1H-indol-2-yl}-2,2-dimethyl-propionic acid (AM679)-A potent FLAP inhibitor"; Bioorganic & Medicinal Chemistry Letters; vol. 20, pp. 213-217 (2010).
Zhao, et al.; "Indoline and Piperazine Containing Derivatives as a Novel Class of Mixed D$_2$/D$_4$ Receptor Antagonists. Part 2: Asymmetric Synthesis and Biological Evaluation"; Bioorganic & Medicinal Chemistry Letters; vol. 12, pp. 3111-3115 (2002).

*Primary Examiner* — Rebecca Anderson
(74) *Attorney, Agent, or Firm* — Perkins Coie LLP; Viola T. Kung

(57) ABSTRACT

The invention relates to morpholino-derivatives according to Formula (I) or stereoisomers or pharmaceutically acceptable salts or solvate thereof, wherein $R^1$, $R^2$, $R^3$, $R^4$, $R^5$, $R^6$, $R^7$, $R^8$, $R^9$, m and n are as defined in the specification. The compounds are antagonists, reverse agonists or agonists of G-protein coupled receptors, such as dopamine D4 and 5HT1a. The inventions also relates to pharmaceutical compositions comprising the compounds and methods involving the compounds and compositions. The compounds and compositions of the invention may in particular be used in the treatment of diseases and disorders, such as neurological and neurodegenerative diseases; or as lead compounds for the design and selection of further therapeutic compounds.

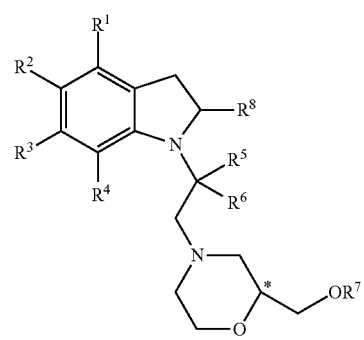

Formula I

18 Claims, No Drawings

MORPHOLINO COMPOUNDS, USES AND METHODS

This application is a continuation of PCT/GB2012/051194, filed May 25, 2012; which claims the priority of GB 1108825.9, filed May 25, 2011. The contents of the above-identified applications are incorporated herein by reference in their entirety.

FIELD OF THE INVENTION

The invention relates to novel morpholino compounds as well as compositions, uses and methods involving the compounds. In particular, the invention relates to morpholino compounds and derivatives that may be useful as antagonists of G-protein coupled receptors (GPCRs), or as lead molecules for the design and synthesis of therapeutic compounds.

BACKGROUND OF THE INVENTION

The serotonin receptors, also known as 5-hydroxytryptamine (5-HT) receptors, are a group of G protein-coupled receptors (GPCRs) and ligand-gated ion channels (LGICs) found in the central and peripheral nervous systems. They are activated by the neurotransmitter serotonin, a natural ligand. Once activated, the serotonin receptors modulate the release of many neurotransmitters, including glutamate, GABA, dopamine, epinephrine/norepinephrine, and acetylcholine; as well as many hormones, including oxytocin, prolactin, vasopressin, cortisol, corticotropin, and substance P. As a result, the serotonin receptors are involved in and influence many different biological and neurological processes such as aggression, anxiety, appetite, cognition, learning, memory, mood, nausea, sleep and thermoregulation. 5-HT receptors are, therefore, targets for a variety of pharmaceutical drugs, including many antidepressants, antipsychotics, anorectics, antiemetics, gastroprokinetic agents and antimigraine agents.

There are seven known serotonin receptor families, which are generally identified by the nomenclature 5HT1 (or 5-$HT_1$) to 5HT7 (5-$HT_7$), and some of these families include a plurality of subtypes. For example, the known subtypes of the 5HT1 family are named from 5HT1a (or 5-$HT_{1a}$) to 5HT1f (5-$HT_{1f}$).

5HT1a antagonists have been shown to exhibit cognitive enhancing effects in a number of animal models of learning and memory. They may also have utility in the treatment of anxiety, for enhancing the antidepressant effects of SSRI fluoxetine, and for potentially reversing the sexual dysfunction induced by chronic fluoxetine treatment (see e.g. Childers W. E. et al., (2010) "The synthesis and biological evaluation of quinolyl-piperazinyl piperidines as potent serotonin 5-HT1A antagonists", *J. Med. Chem.*, 53(10): 4066-4084; and Caliendo G. et al., (2005) "Derivatives as 5HT1A receptor ligands—past and present", *Curr. Med. Chem.* 12(15): 1721-1753).

Accordingly, it would be desirable to have further 5HT1a receptor antagonist and inverse agonist compounds; for example, that may be useful as therapeutics or as lead molecules in the treatment of neurological disorders.

5HT1a agonists such as the azapirones (buspirone, gepirone and tandospirone) have been reported to exert anxiolytic and anti-depressive activity in double-blind, placebo-controlled, and comparative trials and as such 5HT1a agonists may also be useful as therapeutics or as lead molecules in the treatment of neurological disorders.

Dopamine receptors are activated by the natural neurotransmitter ligand, dopamine. Like serotonin receptors, a large number of dopamine receptor subtypes are known in humans and other animals. The D4 receptor is generally considered to be dopamine D2-like, in that the activated receptor inhibits the adenylate cyclase enzyme, thereby reducing the intracellular concentration of the second messenger cyclic AMP (cAMP).

The dopamine D4 receptor has been linked to many neurological and psychiatric conditions including schizophrenia, Parkinson's disease, bipolar disorder, addictive behaviours, and eating disorders such as anorexia nervosa, bulimia nervosa and binge eating. In addition, dopamine D4 receptor antagonists have been reported to prevent stress-induced cognition dysfunction in primates (Arnsten et al. (2000), "The selective dopamine D4 receptor antagonist, PNU-101387G, prevents stress-induced cognitive deficits in monkeys", *Neuropsychopharmacology* 23, pp 405-410). Consequently, D4 antagonists have been linked to the treatment of cognitive dysfunction and amyotrophic lateral sclerosis. In addition, the dopamine D4 receptor is a target for drugs that are intended to treat schizophrenia and Parkinson's disease. A review of dopamine D4 ligands can be found in Löber S. et al., (2011) "Recent advances in the search for D(3)- and D(4)-selective drugs: probes, models and candidate", *Trends Pharmacol. Sci.*, 32(3), pp 148-57. For example, a dopamine receptor antagonist L-745,870 has been shown to suppress microglia activation in spinal cord and mitigates the progression in ALS model mice (Tanaka K. et al., (2008) *Exp. Neurol.*, 211(2), pp 378-86). Accordingly, there is a need for further dopamine D4 receptor antagonists for use in treating one or more neurological diseases.

Furthermore, polypharmaceutical drugs (i.e. drugs that show selectivity and activity against more than one useful therapeutic target at the same time), are desirable because of the great potential they offer as new or enhanced therapeutic molecules. For example, a compound capable of antagonising a combination of the 5HT1a and dopamine D4 receptors may provide potential novel approaches for enhancing cognitive function, such as in learning and memory; and for treating diseases of cognitive dysfunction, such as schizophrenia, depression, ALS, anxiety, Parkinson's disease and Alzheimer's disease. It would, therefore, be advantageous to have new polypharmaceutical compounds for the treatment of diseases, and especially neurological disorders.

The present invention addresses one or more of the above-mentioned needs or problems in the art.

SUMMARY OF THE INVENTION

In broad terms, the present invention relates to novel morpholino compounds, and in particular, morpholino-indoline derivatives. The compounds have activity as antagonists and inverse agonists of GPCRs, such as dopamine D4 and serotonin 5HT1a. In some cases the compounds of the invention are highly specific for only one GPCR; while in other cases the compounds exhibit useful polypharmacology, having activity for two or three GPCRs. The compounds may be used directly, or may be used in salt, solvate, derivative or prodrug forms. The compounds may be formulated or manufactured into pharmaceutical compositions and medicaments. The invention is also directed to methods, both in vitro and in vivo, using the compounds and compositions of the invention. Particularly useful therapeutic uses are directed towards the treatment of neurological or neurodegenerative diseases or disorders in mammals, such as humans.

Thus, in a first aspect, the invention provides a compound of Formula I:

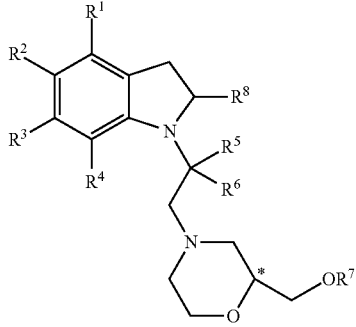

Formula I or a stereoisomer or a pharmaceutically acceptable salt or solvate thereof, wherein: $R^1$, $R^2$, $R^3$ and $R^4$ are each independently selected from hydrogen, halogen, hydroxy, optionally substituted alkyl, optionally substituted alkoxy; $R^5$ and $R^6$ are each hydrogen, or $R^5$ and $R^6$ together are =O; $R^7$ is hydrogen, optionally substituted alkyl, optionally substituted alkenyl, optionally substituted alkynyl, optionally substituted alkoxy, optionally substituted aryl, optionally substituted arylalkyl, optionally substituted heteroaryl, optionally substituted cycloalkyl, optionally substituted heterocycloalkyl, alkylcarbonyl, —C(O)—$R^a$; $R^a$ is selected from H, $(C_1\text{-}C_6)$ alkyl, $(C_1\text{-}C_6)$alkoxy, halo$(C_1\text{-}C_6)$alkyl, hydroxy$(C_1\text{-}C_6)$alkyl, $(C_5\text{-}C_6)$aryl, halo$(C_5\text{-}C_6)$aryl, hydroxy$(C_5\text{-}C_6)$aryl, alkoxy$(C_5\text{-}C_6)$aryl, $(C_5\text{-}C_6)$aryloxy, a 5 or 6 membered heteroaryl optionally substituted with halogen, hydroxy or alkoxy; and a 4 to 6 membered heterocycloalkyl optionally substituted with halogen, hydroxy or alkoxy; $R^8$ is hydrogen or optionally substituted alkyl; and the configuration at * is (R), (S) or a racemic mixture.

In some embodiments $R^5$, $R^6$ and $R^8$ are hydrogen. Thus, in beneficial aspects and embodiments, the invention provides a compound of Formula II, wherein $R^1$, $R^2$, $R^3$ and $R^4$ and $R^7$ are as defined above and elsewhere herein. In some embodiments, the compound of Formula II is preferably in the (S) configuration at the * carbon atom.

In accordance with an alternative aspect of the invention, further useful compounds are those wherein $R^5$ and $R^6$ together are =O. Hence, the invention also provides compounds of Formula III.

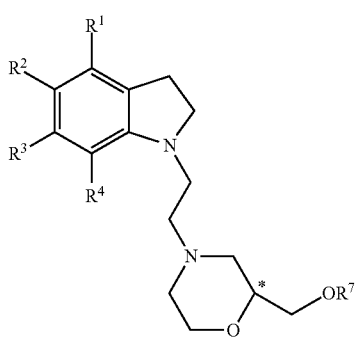

Formula II

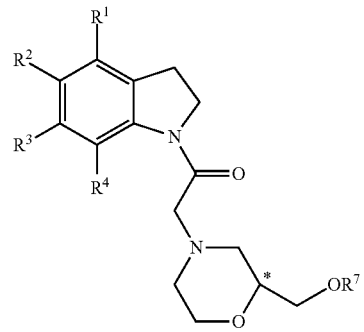

Formula III

In some embodiments $R^1$, $R^2$, $R^3$ and $R^4$ are each independently selected from hydrogen, chloro, fluoro, bromo, methyl, and methoxy. Typically two or more (i.e. 2, 3 or 4) of $R^1$, $R^2$, $R^3$ and $R^4$ are hydrogen.

$R^7$ in accordance with some beneficial embodiments is selected from the group consisting of: hydrogen, optionally substituted $(C_1\text{-}C_6)$alkyl, optionally substituted $(C_5\text{-}C_{15})$aryl, optionally substituted $(C_5\text{-}C_{15})$aryl$(C_1\text{-}C_6)$alkyl, an optionally substituted 5 to 15 membered heteroaryl, and an optionally substituted 4 to 15 membered heterocycloalkyl. Optional substituents may be any of those defined herein. A preferred group of substituents consists of halogen, hydroxy, $(C_1\text{-}C_6)$ alkyl, halo$(C_1\text{-}C_6)$alkyl, hydroxy$(C_1\text{-}C_6)$alkyl, $(C_1\text{-}C_6)$ alkoxy, halo$(C_1\text{-}C_6)$alkoxy, hydroxy$(C_1\text{-}C_6)$alkoxy; and the moiety may be substituted with one or more such substituent (e.g. 1, 2, 3 or 4).

A particularly useful advantageous $R^7$ group is defined by the following structure:

wherein:
X, Y and Z are independently selected from C and N; and where present, $R^9$, $R^{10}$, $R^{11}$, $R^{12}$ and $R^{13}$ are each independently selected from hydrogen, $(C_1\text{-}C_6)$alkyl, $(C_1\text{-}C_6)$alkoxy, halo$(C_1\text{-}C_6)$alkyl, hydroxy$(C_1\text{-}C_6)$alkyl, $(C_5\text{-}C_6)$aryl, halo$(C_5\text{-}C_6)$aryl, hydroxy$(C_5\text{-}C_6)$aryl, alkoxy$(C_5\text{-}C_6)$aryl, $(C_5\text{-}C_6)$aryloxy, a 5 or 6 membered heteroaryl optionally substituted with halogen, hydroxy or alkoxy; and a 4 to 6 membered heterocycloalkyl optionally substituted with halogen, hydroxy or alkoxy; and optionally, wherein two adjacent $R^9$, $R^{10}$, $R^{11}$, $R^{12}$ and $R^{13}$ groups are joined together with the ring atoms to which they are attached to form a ring selected from: an optionally substituted 4- to 6-membered cycloalkyl or heterocycloalkyl; or an optionally substituted 5- or 6-membered aryl or heteroaryl group, the optional substituents selected from one or more of hydroxyl, fluoro, chloro, bromo, methoxy, ethoxy, chloro$(C_1\text{-}C_2)$alkyl, and hydroxy$(C_1\text{-}C_2)$alkyl, —CN, —$CF_3$, —$NO_2$, —$NH_2$, and —NH$(C_1\text{-}C_4)$alkyl.

Where Z is nitrogen, $R^7$ may for example have one of the following structures, wherein $R^9$, $R^{10}$, $R^{12}$ and $R^{13}$ are as defined elsewhere:

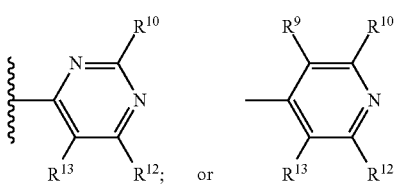

In other preferred embodiments, Z is carbon, such that $R^7$ may have the following structure:

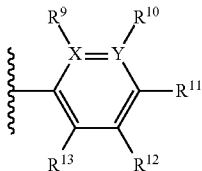

wherein $R^9$, $R^{10}$, $R^{11}$, $R^{12}$ and $R^{13}$ are as defined elsewhere.

Suitably, however, only 1 or X or Y is nitrogen. Thus, useful representative $R^7$ groups are defined by one of the following structures:

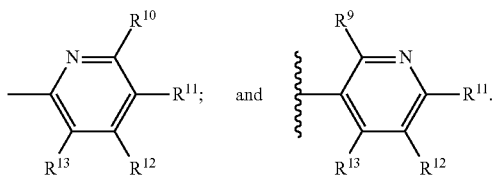

In other embodiments it is desirable that X, Y and Z are all carbon, in which case $R^7$ may have the following structural formula:

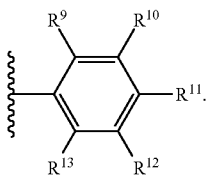

In some embodiments, $R^{10}$, $R^{11}$, $R^{12}$, $R^{13}$ and $R^{14}$ are, where present, each independently selected from hydrogen, $(C_1-C_6)$alkyl, $(C_1-C_6)$alkoxy, halo$(C_1-C_6)$alkyl, and hydroxy$(C_1-C_6)$alkyl. In other embodiments, $R^9$, $R^{10}$, $R^{11}$, $R^{12}$ and $R^{13}$, where present, are each independently selected from hydrogen, $(C_5-C_6)$aryl, halo$(C_5-C_6)$aryl, hydroxy$(C_5-C_6)$aryl, alkoxy$(C_5-C_6)$aryl, $(C_5-C_6)$aryloxy, a 5 or 6 membered heteroaryl optionally substituted with halogen, hydroxy or alkoxy; and a 4 to 6 membered heterocycloalkyl optionally substituted with halogen, hydroxy or alkoxy. In still other embodiments, two adjacent $R^9$, $R^{10}$, $R^{11}$, $R^{12}$ and $R^{13}$ groups are joined together with the ring atoms to which they are attached to form a ring selected from: an optionally substituted 4- to 6-membered cycloalkyl or heterocycloalkyl; or an optionally substituted 5- or 6-membered aryl or heteroaryl group, the optional substituents selected from one or more of hydroxyl, fluoro, chloro, bromo, methoxy, ethoxy, chloro$(C_1-C_2)$alkyl, and hydroxy$(C_1-C_2)$alkyl, —CN, —CF$_3$, —NO$_2$, —NH$_2$, and —NH$(C_1-C_4)$alkyl.

Advantageously, where $R^7$ comprises a 6-membered aryl or heteroaryl group, at least 1, 2 or 3 of $R^9$, $R^{10}$, $R^{11}$, $R^{12}$ and $R^{13}$ are hydrogen, and the rest are independently selected from: chloro, fluoro, methyl, ethyl, methoxy, and ethoxy. In one embodiment all of $R^9$, $R^{10}$, $R^{11}$, $R^{12}$ and $R^{13}$ are hydrogen. In some beneficial embodiments, 1 or 2 of $R^9$, $R^{10}$, $R^{11}$, $R^{12}$ and $R^{13}$ is selected from chloro, fluoro, methyl or methoxy; and the rest, where present, are hydrogen.

Preferred $R^7$ groups are phenyl; 2-, 3- or 4-methylphenyl; 2-, 3- or 4-chlorophenyl; 2-, 3- or 4-fluorophenyl, 2-, 3- or 4-methoxyphenyl; 2-, 3- or 4-pyridyl; 3-, 4-, 5- or 6-methylpyridin-2-yl; 3-, 4-, 5- or 6-chloropyridin-2-yl; 3-, 4-, 5- or 6-fluoropyridin-2-yl; 3-, 4-, 5- or 6-methoxypyridin-2-yl; 2-, 4-, 5- or 6-methylpyridin-3-yl; 2-, 4-, 5- or 6-chloropyridin-3-yl; 2-, 4-, 5- or 6-fluoropyridin-3-yl; 2-, 4-, 5- or 6-methoxypyridin-3-yl; 2- or 3-methylpyridin-4-yl; 2- or 3-chloropyridin-4-yl; 2- or 3-fluoropyridin-4-yl; 2- or 3-methoxypyridin-4-yl.

In any of the aspects and embodiments of the invention, $R^8$ may advantageously be selected from hydrogen, methyl, ethyl, chloro$(C_1-C_2)$alkyl, and hydroxy$(C_1-C_2)$alkyl. Preferred $R^8$ substituents are hydrogen or methyl.

In some preferred aspects and embodiments, the substituents are selected from: fluoro, chloro, bromo, hydroxy, amino, $(C_1-C_6)$alkyl and $(C_1-C_6)$alkoxy, wherein alkyl and alkoxy are optionally substituted by one or more chloro. A particularly preferred groups of substituents consists of: chloro, methyl, ethyl, methoxy and ethoxy, wherein methyl, ethyl, methoxy and ethoxy are optionally substituted by one or more chloro. Other possible substituent groups are defined elsewhere.

In particularly beneficial embodiments, the compound of the invention is a compound as exemplified herein, such as in Examples 2 to 58. Preferred compounds of the invention include compounds 14r, 15r, 16r, 17r, 18s, 19s, 20r, 20s, 21r, 21s, 22r, 22s, 23r, 23s, 24s, 25r, 25s, 26r, 26s, 27r, 27s, 28r, 28s, 29r and 32s; and/or compounds 60, 61, 62, 63, 64, 65, 66, 67, 68, 69 and 70. Preferred intermediates of the invention include compounds 47, 48s, 49r, 50, 51s and 52r.

The invention also encompasses compositions comprising one or more compound of the invention, or a salt, solvate, derivative or prodrug thereof.

For example, the compounds and derivatives of the invention may be formulated into pharmaceutical compositions. Therefore, in another aspect, the invention provides pharmaceutical compositions/therapeutics comprising one or more compound of the invention (and a pharmaceutically acceptable carrier). It is envisaged that the compounds and compositions of the invention may have pharmaceutical activity (in vitro, ex vivo or preferably in vivo) against one or more medical condition, disease or disorder. Preferably, the compounds of the invention are antagonists or inverse agonists of the target receptor. In some embodiments, however, the compounds may be agonsists or a receptor. Hence, the invention, in another aspect, provides for compounds of the invention for use in medicine; and in particular, for a use in treating specified medical indications or diseases associated with specified target molecules, such as a disease or disorder associated with GPCRs. Specific therapeutic targets for the compounds and compositions of the invention include the dopamine D4 receptor and/or the serotonin 5HT1a receptor. Suitably, the disease or disorder is a neurological or neurodegenerative disease or disorder. More suitably, the condition may be selected from: cognitive dysfunction, such as schizophrenia and amyotrophic lateral sclerosis; neurodegenerative diseases, such as Parkinson's disease, and Alzheimer's diseases; bipolar disorder; depression; anxiety; addictive behaviours; obsessive compulsive disorders; sexual dysfunction; and eating disorders, such as anorexia nervosa, bulimia nervosa and binge eating. The therapeutic compounds and compositions of the invention may be used independently, or as a combination therapy in combination with one or more further therapeutic agent of the invention or otherwise.

Methods for the treatment of a disease or condition in a subject are also envisaged. Furthermore, methods for antagonising a GPCR (such as those identified herein), comprising exposing the GPCR to one or more compounds or one or more compositions of the invention are encompassed. The methods may be performed in vitro, ex vivo or in vivo.

The invention further encompasses the use of a compound of the invention for the preparation of a medicament.

In another aspect of the invention, there is disclosed a process for preparing a compound of the invention, comprising: (a) reacting a compound of Formula XIII:

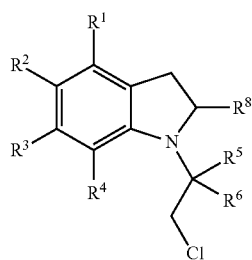

Formula XIII with a compound of Formula (XIV):

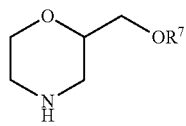

Formula XIV

The process of step (a) is generally carried out in the presence of a base, e.g. an organic base, such as a trialkyl amine. In some embodiments, the reaction takes place in the presence of a solvent, e.g. an organic solvent, such as an aprotic solvent.

$R^7$ of Formula XIV may be defined as elsewhere herein, in accordance with any aspect or embodiment of the invention. For example, $R^7$ may be selected from hydrogen, optionally substituted $(C_1-C_6)$alkyl, optionally substituted $(C_5-C_{15})$aryl, optionally substituted $(C_5-C_{15})$aryl$(C_1-C_6)$alkyl, an optionally substituted 5 to 15 membered heteroaryl, and an optionally substituted 4 to 15 membered heterocycloalkyl. Beneficially, when the product of step (a) is an intermediate in the preparation of a compound of Formula I, $R^7$ is suitably selected from hydrogen or $(C_1-C_6)$alkyl; and is preferably hydrogen.

Thus, in one aspect the invention relates to intermediate compounds useful in the preparation of the compounds of Formula I. The intermediate of the invention may be the product of step (a) above.

The process for preparing a compound of the invention may further comprise: (b) reacting the product of step (a) with a compound of formula $R^7$-LG to form a compound of Formula I:

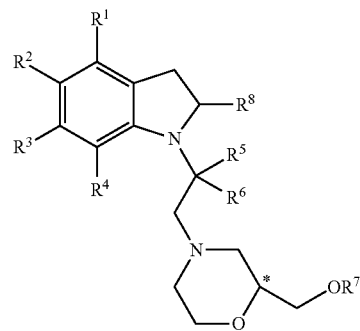

Formula I wherein LG is a leaving group, and wherein $R^7$ is defined elsewhere herein. Thus, $R^7$ of the compound of Formula I may be the same or different from $R^7$ in the product of step (a), which is replaced in step (b) by $R^7$ of the molecule $R^7$-LG. Suitably, LG is selected from halogen or hydroxy; and preferably LG is chloro or hydroxy.

The process of step (b) may be carried out in the presence of a base. In accordance with some embodiments, the base may be an organic base. A solvent, e.g. an organic solvent (such as THF or diethylether) may optionally be present. In some beneficial embodiments, the reaction may comprise a Mitsunobu reaction. A Mitsunobu reaction may suitably include a trialkyl or triaryl phosphine, such as triphenylphosphine ($Ph_3P$); and/or one or more further reagent, such as diethyl azodicarboxylate (DEAD). A Mitsunobu reaction may be particularly useful when the leaving group, LG is hydroxy. In accordance with some other embodiments, step (b) may be carried out in the presence of a non-organic base, such as an alkali metal hydride. A preferred alkali metal halide is NaH. Such non-organic bases may be preferred where the leaving group, LG is a halogen, such as bromo.

In yet another aspect, the invention provides for the use of a process according to the invention for preparing a compound of Formula I.

In addition or alternatively to their use a therapeutic agents per se, the compounds of the invention may be particularly useful as lead compounds for the design, selection and synthesis of further therapeutically-active agents; especially as lead compounds for the selection of further agonists or antagonists of GPCRs, such as dopamine D4 and/or serotonin 5HT1a.

It should be appreciated that in any aspect of the invention, unless otherwise stated, any feature of an embodiment of another aspect may be combined with features of that aspect to create an embodiment of the invention; and all such combinations are envisaged herein.

These and other features and advantages of the invention should be apparent to those skilled in the art from the teachings provided herein.

All references cited herein are incorporated by reference in their entirety.

DETAILED DESCRIPTION OF THE INVENTION

Described herein are compounds and compositions (e.g. organic molecules, research tools, pharmaceutical formulations and therapeutics); uses for the compounds and compositions of the invention; as well as corresponding methods, whether diagnostic, therapeutic or for research applications. The chemical synthesis and biological testing of the compounds of the invention are also described. Beneficially, the compounds, compositions, uses and methods have utility in research towards and/or the treatment of diseases in animals, such as humans. The diseases may be neurological or psychological disorders, and the disease targets may suitably be those associated with GPCRs: particularly dopamine receptors, such as D4, and/or serotonin receptors, such as 5HT1a. Preferred disease targets include schizophrenia, amyotrophic lateral sclerosis, Parkinson's disease, Alzheimer's disease, bipolar disorder, depression, anxiety, obsessive compulsive disorders, sexual dysfunction, and eating disorders. However, the compounds may also or alternatively be useful as lead molecules for the selection, screening and development of further derivatives that may have one or more improved beneficial drug property, as desired. Such further selection and screening may be carried out using the proprietary computational evolutionary algorithm described herein, or using any other suitable computational or physical selection and screening system known in the art. Thus, the invention also relates to the computational evolutionary algorithm used in the selection and screening of potential drug candidates, and in particular to identify the compounds and derivatives of the invention.

The compounds of the invention are generally morpholino derivatives, and are advantageously indoline-morpholino derivatives. The invention also encompasses salts, solvates and functional derivatives of the compounds of the invention.

General

Unless defined otherwise, all technical and scientific terms used herein have the same meaning as commonly understood by one of ordinary skill in the art (e.g. in organic, physical or theoretical chemistry; and biochemistry).

Unless otherwise indicated, the practice of the present invention employs conventional techniques in chemistry and chemical methods, biochemistry, pharmaceutical formulation, and delivery and treatment regimes for patients, which are within the capabilities of a person of ordinary skill in the art. Such techniques are also described in the literature cited herein, each of which is herein incorporated by reference.

Prior to setting forth the detailed description of the invention, a number of definitions are provided that will assist in the understanding of the invention.

In accordance with the invention, the term 'molecule' or 'molecules' is used interchangeably with the terms 'compound(s)', and sometimes a 'chemical structure'. The term 'drug' is typically used in the context of a pharmaceutical, pharmaceutical composition, medicament or the like, which has a known or predicted physiological or in vitro activity of medical significance; but such characteristics and qualities are not excluded in a molecule of the invention. The term 'drug' is therefore used interchangeably with the alternatives terms and phrases 'therapeutic (agent)', 'pharmaceutical (agent)', and 'active (agent)'. Therapeutics of the invention also encompass compositions and pharmaceutical formulations comprising the compounds of the invention.

Prodrugs and solvates of the compounds of the invention are also encompassed within the scope of the invention. The term 'prodrug' means a compound (e.g. a drug precursor) that is transformed in vivo to yield a compound of the invention or a pharmaceutically acceptable salt, solvate or ester of the compound. The transformation may occur by various mechanisms (e.g. by metabolic or chemical processes), such as by hydrolysis of a hydrolysable bond, e.g. in blood (see Higuchi & Stella (1987) "Pro-drugs as Novel Delivery Systems", vol. 14 of the *A.C.S. Symposium Series*; (1987) "Bioreversible Carriers in Drug Design", Roche, ed., *American Pharmaceutical Association and Pergamon Press*). The compositions and medicaments of the invention therefore may comprise prodrugs of the compounds of the invention.

In the context of the present invention, the terms 'individual', 'subject', or 'patient' are used interchangeably to indicate an animal that may be suffering from a medical condition and may be responsive to a molecule, pharmaceutical drug, medical treatment or therapeutic treatment regime of the invention. The animal is suitably a mammal, such as a human, cow, sheep, pig, mouse or rat. Preferably the subject is a human.

The term 'alkyl' refers to a monovalent, optionally substituted, saturated aliphatic hydrocarbon radical. Any number of carbon atoms may be present, but typically the number of carbon atoms in the alkyl group may be from 1 to about 20, from 1 to about 12, from 1 to about 6 or from 1 to about 4. Usefully, the number of carbon atoms is indicated, for example, a C1-12 alkyl (or $C_{1-12}$ alkyl) refers to any alkyl group containing 1 to 12 carbon atoms in the chain. An alkyl group may be a straight chain (i.e. linear), branched chain, or cyclic. 'Lower alkyl' refers to an alkyl of 1 to 6 carbon atoms in the chain, and may have from 1 to 4 carbon atoms, or 1 to 2 carbon atoms. Thus, representative examples of lower alkyl radicals include methyl, ethyl, n-propyl, n-butyl, n-pentyl, n-hexyl, isopropyl, isobutyl, isopentyl, amyl ($C_5H_{11}$), sec-butyl, tert-butyl, sec-amyl, tert-pentyl, 2-ethylbutyl, 2,3-dimethylbutyl, and the like. 'Higher alkyl' refers to alkyls of 7 carbons and above, including n-heptyl, noctyl, n-nonyl, n-decyl, n-dodecyl, n-tetradecyl, n-hexadecyl, n-octadecyl, n-eicosyl, and the like, along with branched variations thereof. A linear carbon chain of say 4 to 6 carbons would refer to the chain length not including any carbons residing on a branch, whereas in a branched chain it would refer to the total number. Optional substituents for alkyl and other groups are described below.

The term 'substituted' means that one or more hydrogen atoms (attached to a carbon or heteroatom) is replaced with a selection from the indicated group of substituents, provided that the designated atom's normal valency under the existing circumstances is not exceeded. The group may be optionally substituted with particular substituents at positions that do not significantly interfere with the preparation of compounds falling within the scope of this invention and on the understanding that the substitution(s) does not significantly adversely affect the biological activity or structural stability of the compound. Combinations of substituents are permissible only if such combinations result in stable compounds. By 'stable compound' or 'stable structure', it is meant a compound that is sufficiently robust to survive isolation to a useful degree of purity from a reaction mixture and/or formulation into an efficacious therapeutic agent. By 'optionally substituted' it is meant that the group concerned is either unsubstituted, or at least one hydrogen atom is replaced with one of the specified substituent groups, radicals or moieties.

Any radical/group/moiety described herein that may be substituted (or optionally substituted) may be substituted with one or more (e.g. one, two, three, four or five) substituents, which are independently selected from the designated group of substituents. Thus, substituents may be selected from the group: halogen (or 'halo', e.g. F, Cl and Br), hydroxyl (—OH), amino (—$NH_2$), thiol (—SH), cyano (—CN), (lower) alkyl, (lower) alkoxy, (lower) alkenyl, (lower) alkynyl, aryl, heteroaryl, (lower) alkylthio, oxo, haloalkyl, hydroxyalkyl, nitro (—$NO_2$), phosphate, azido (—$N_3$), alkoxycarbonyl, carboxy, alkylcarboxy, alkylamino, dialkylamino, aminoalkyl, alkylaminoalkyl, dialkylaminoalkyl, thioalkyl, alkylsulfonyl, arylsulfinyl, alkylaminosulfonyl, arylaminosulfonyl, alkylsulfonylamino, arylsulfonylamino, carbamoyl, alkylcarbamoyl, dialkylcarbamoyl, arylcarbamoyl, alkylcarbonylamino, arylcarbonylamino, cycloalkyl, heterocycloalkyl, unless otherwise indicated. Alternatively, where the substituents are on an aryl or other cyclic ring system, two adjacent atoms may be substituted with a methylenedioxy or ethylenedioxy group. More suitably, the substituents are selected from: halogen, hydroxy, amino, thiol, cyano, $(C_1-C_6)$alkyl, $(C_1-C_6)$alkoxy, $(C_1-C_6)$alkenyl, $(C_1-C_6)$alkynyl, aryl, aryl$(C_1-C_6)$alkyl, aryl$(C_1-C_6)$alkoxy, heteroaryl, $(C_1-C_6)$alkylthio, oxo, halo$(C_1-C_6)$alkyl, hydroxy$(C_1-C_6)$alkyl, nitro, phosphate, azido, $(C_1-C_6)$alkoxycarbonyl, carboxy, $(C_1-C_6)$alkylcarboxy, $(C_1-C_6)$alkylamino, di$(C_1-C_6)$alkylamino, amino$(C_1-C_6)$alkyl, $(C_1-C_6)$alkylamino$(C_1-C_6)$alkyl, di$(C_1-C_6)$alkylamino$(C_1-C_6)$alkyl, thio$(C_1-C_6)$alkyl, $(C_1-C_6)$alkylsulfonyl, arylsulfinyl, $(C_1-C_6)$alkylaminosulfonyl, arylaminosulfonyl, $(C_1-C_6)$alkylsulfonylamino, arylsulfonylamino, carbamoyl, $(C_1-C_6)$alkylcarbamoyl, di$(C_1-C_6)$alkylcarbamoyl, arylcarbamoyl, $(C_1-C_6)$alkylcarbonylamino, arylcarbonylamino, $(C_1-C_6)$cycloalkyl, and heterocycloalkyl. Still more suitably, the substituents are selected from one or more of: fluoro, chloro, bromo, hydroxy, $(C_1-C_6)$alkyl, $(C_1-C_6)$haloalkyl, $(C_1-C_6)$alkoxy, $(C_5-C_6)$aryl, a 5- or 6-membered heteroaryl, $(C_4-C_6)$cycloalkyl, a 4- to 6-membered heterocycloalkyl, cyano, $(C_1-C_6)$alkylthio, amino, —NH(alkyl), —NH($(C_1-C_6)$cycloalkyl), —N($(C_1-C_6)$alkyl)$_2$, —OC(O)—$(C_1-C_6)$alkyl, —OC(O)—$(C_5-C_6)$aryl, —OC(O)—$(C_1-C_6)$cycloalkyl, carboxy and —C(O)O—$(C_1-C_6)$alkyl. Most suitably, the substituents are selected from one or more of: fluoro, chloro, bromo, hydroxy, amino, $(C_1-C_6)$alkyl and $(C_1-C_6)$alkoxy, wherein alkyl and alkoxy are optionally substituted by one or more chloro. Particularly preferred substituents are: chloro, methyl, ethyl, methoxy and ethoxy.

The term 'halo' refers to a monovalent halogen radical chosen from chloro, bromo, iodo, and fluoro. A 'halogenated' compound is one substituted with one or more halo substituent. Preferred halo groups are F, Cl and Br, and most preferred is Cl.

When used herein, the term 'independently', in reference to the substitution of a parent moiety with one or more substituents, means that the parent moiety may be substituted with any of the listed substituents, either individually or in combination, and any number of chemically possible substituents may be used. In any of the embodiments, where a group is substituted, it may contain up to 5, up to 4, up to 3, or 1 and 2 substituents. As a non-limiting example, useful substituents include: phenyl or pyridine, independently substituted with one or more lower alkyl, lower alkoxy or halo substituents, such as: chlorophenyl, dichlorophenyl, trichlorophenyl, tolyl, xylyl, 2-chloro-3-methylphenyl, 2,3-dichloro-4-methylphenyl, etc.

"Alkylene" or "alkylenyl" means a difunctional group obtained by removal of a hydrogen atom from an alkyl group as defined above. Non-limiting examples of alkylene include methylene, ethylene and propylene. 'Lower alkylene' means an alkylene having from 1 to 6 carbon atoms in the chain, and may be straight or branched. Alkylene groups are optionally substituted. Preferred alkylene groups are —$(CR_2)_n$— where n is from 1 to 6, and R is independent selected from H, F, Cl, $NH_2$ or wherein $R_2$ is =O. More preferably, n is 1, 2 or 3 and R is H. Most preferable alkylene groups are —$(CH_2)_2$— and —$CH_2$—CO—.

The term 'alkenyl' refers to a monovalent, optionally substituted, unsaturated aliphatic hydrocarbon radical. Therefore, an alkenyl has at least one carbon-carbon double bond (C=C). The number of carbon atoms in the alkenyl group may be indicated, such as from 2 to about 20. For example, a $C_{2-12}$ alkenyl (or $C_{2-12}$ alkenyl) refers to an alkenyl group containing 2 to 12 carbon atoms in the structure. Alkenyl groups may be straight (i.e. linear), branched chain, or cyclic. 'Lower alkenyl' refers to an alkenyl of 1 to 6 carbon atoms, and may have from 1 to 4 carbon atoms, or 1 to 2 carbon atoms. Representative examples of lower alkenyl radicals include ethenyl, 1-propenyl, 1-butenyl, 1-pentenyl, 1-hexenyl, isopropenyl, isobutenyl, and the like. Higher alkenyl refers to alkenyls of seven carbons and above, such as 1-heptenyl, 1-octenyl, 1-nonenyl, 1-decenyl, 1-dodecenyl, 1-tetradecenyl, 1-hexadecenyl, 1-octadecenyl, 1-eicosenyl, and the like, along with branched variations thereof. Optional substituents include are described elsewhere.

'Alkenylene' means a difunctional group obtained by removal of a hydrogen from an alkenyl group that is defined above. Non-limiting examples of alkenylene include —CH=CH—, —C(CH$_3$)=CH—, and —CH=CHCH$_2$—.

'Alkynyl' and 'lower alkynyl' is defined similarly to the term 'alkenyl', except that it includes at least one carbon-carbon triple bond.

The term 'alkoxy' refers to a monovalent radical of the formula RO—, where R is any alkyl, alkenyl or alkynyl as defined herein. Alkoxy groups may be optionally substituted by any of the optional substituents described herein. 'Lower alkoxy' has the formula RO—, where the R group is a lower alkyl, alkenyl or alkynyl. Representative alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Preferred alkoxy groups are methoxy and ethoxy.

The term 'aryl' as used herein refers to a substituted or unsubstituted aromatic carbocyclic radical containing from 5 to about 15 carbon atoms; and preferably 5 or 6 carbon atoms. An aryl group may have only one individual carbon ring, or may comprise one or more fused rings in which at least one ring is aromatic in nature. A 'phenyl' is a radical formed by removal of a hydrogen atom from a benzene ring, and may be substituted or unsubstituted. A 'phenoxy' group, therefore, is a radical of the formula RO—, wherein R is a phenyl radical. 'Benzyl' is a radical of the formula R—$CH_2$—, wherein R is phenyl, and 'benzyloxy' is a radical of the formula RO—, wherein R is benzyl. Non-limiting examples of aryl radicals include, phenyl, naphthyl, benzyl, biphenyl, furanyl, pyridinyl, indanyl, anthraquinolyl, tetrahydronaphthyl, a benzoic acid radical, a furan-2-carboxylic acid radical, and the like.

A 'heteroaryl' group is herein defined as a substituted or unsubstituted 'aryl' group in which one or more carbon atoms in the ring structure has been replaced with a heteroatom, such as nitrogen, oxygen or sulphur. Generally the heteroaryl group contains one or two heteroatoms. A preferred heteroatom is N. Exemplary heteroaryl groups include: furan, benzofuran, isobenzofuran, pyrrole, indole, isoindole, thiophene, benzothiophene, benzo[c]thiophene, imidazole, benzimidazole, purine, pyrazole, indazole, oxazole, benzoxazole, isoxazole, benzisoxazole, thiazole, benzothiazole, pyridine, quinoline, isoquinoline, pyrazine, quinoxaline, acridine, pyrimidine, quinazoline, pyridazine and cinnoline.

The terms 'heterocycle' or 'heterocyclic' group as used herein refer to a monovalent radical of from about 4- to about 15-ring atoms, and preferably 4-, 5- or 6-ring members.

Generally the heterocyclic group contains one or two heteroatoms, selected independently from nitrogen, oxygen and sulphur. A preferred heteroatom is N. A heterocyclic group may have only one individual ring, or may comprise one or more fused rings in which at least one ring contains a heteroatom. It may be fully saturated or partially saturated, and may be substituted or unsubstituted as in the case or aryl and heteroaryl groups. Representative examples of unsaturated 5-membered heterocycles with only one heteroatom include 2- or 3-pyrrolyl, 2- or 3-furanyl, and 2- or 3-thiopenyl. Corresponding partially saturated or fully saturated radicals include 3-pyrrolin-2-yl, 2- or 3-pyrrolindinyl, 2- or 3-tetrahydrofuranyl, and 2- or 3-tetrahydrothiophenyl. Representative unsaturated 5-membered heterocyclic radicals having two heteroatoms include imidazolyl, oxazolyl, thiazolyl, pyrazolyl, and the like. The corresponding fully saturated and partially saturated radicals are also included. Representative examples of unsaturated 6-membered heterocycles with only one heteroatom include 2-, 3-, or 4-pyridinyl, 2H-pyranyl, and 4H-pryanyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two heteroatoms include 3- or 4-pyridazinyl, 2-, 4-, or 5-pyrimidinyl, 2-pyrazinyl, morpholino, and the like. The corresponding fully saturated and partially saturated radicals are also included, e.g. 2-piperazine. The heterocyclic radical is bonded through an available carbon atom or heteroatom in the heterocyclic ring directly to the entity or through a linker such as an alkylene such as methylene or ethylene.

Molecules and Compounds

The compounds of the invention are morpholino derivatives. More suitably, the compounds are morpholino-isoindole derivatives.

The compounds of the invention may also be useful in therapeutic and non-therapeutic applications. Non-therapeutic applications include diagnostic tests and in vitro assays. A particularly beneficial application for the compounds of the invention is as polypharmaceutical drugs for the specific/intended targeting of more than one therapeutic target, so as to achieve an advantageous therapeutic activity.

One or more compounds of the invention may exist in unsolvated and/or solvated forms, with pharmaceutically acceptable solvents such as water, ethanol, and the like, and it is intended that the invention embrace both solvated and unsolvated forms. 'Solvate' means a physical association between a compound of this invention and one or more solvent molecules, such as ionic and hydrogen bonding. In certain instances the solvate will itself be capable of isolation, e.g. when one or more solvent molecules are incorporated into a crystal lattice of the crystalline solid. Thus, a solvate encompasses both solution-phase and solids of the compounds of the invention. Non-limiting examples of suitable solvates include ethanolates and methanolates. A 'hydrate', as commonly understood in the art represents a solvate in which the solvent is water.

The preparation of solvates is generally known in the art (for example, see Caira et al. (2004), J. Pharmaceutical Sci., 93(3), 601-611; Tonder et al. (2004), AAPS PharmSciTech., 5(1), article 12; and Bingham et al., (2001), Chem. Commun., 603-604), which described the preparation of solvates, hemisolvates and hydrates. A typical, non-limiting, process for the preparation of solvates and crystals of the compounds of the invention involves dissolving the compound or its derivative in a desired amount of the solvent, optionally at a higher than ambient temperature, and cooling the solution at a rate sufficient to form crystals which are then isolated by standard methods. The solvent may be organic, water, or may comprise and suitable mixtures of organic liquids and water. Various analytical techniques such as I. R. spectroscopy, can be used to study the crystals, for example, to show the presence of the solvent (or water) in the crystals as a solvate (or hydrate).

Also within the scope of the invention are salts, which can be formed from the compounds of the invention. Indeed, reference to a compound of the invention should be understood to include reference to salts thereof, unless otherwise stated. Thus, all acid and base salts of the compounds of the invention are considered for the purposes of the invention to be equivalent to the free forms of the corresponding compounds. The term 'salt', as used herein, includes acidic or basic salts formed with inorganic and/or organic acids. Zwitterions may also be formed from the compounds of the invention, for example, when a compound of the invention contains both a basic moiety (e.g. pyridine or an imidazole), and an acidic moiety (e.g. a carboxylic acid), and such forms are incorporated within the salts of the invention. Beneficially, the salts are non-toxic, such that they may be pharmaceutically and/or physiologically acceptable. However, other salts may also have utility in non-therapeutic applications.

Salts of the compounds of Formula I, for example, may be formed by reacting a compound of Formula I with an acid or base (e.g. HCl), and then allowing the salt to precipitate. The reaction may be conducted in a medium which encourages precipitation/crystallisation, or the medium (e.g. an aqueous medium containing water) may be at least partially removed, such as by lyophilisation, so as to encourage precipitation of the salt of the invention. The amount of acid or base added may suitably be a molar-equivalent amount (i.e. 1:1).

Any suitable acid addition salts can be formed, such as, but are not limited to: acetates, ascorbates, benzoates, citrates, hydrochlorides, hydrobromides, lactates, maleates, nitrates, oxalates, phosphates, propionates, salicylates, succinates, and sulfates. Acids which are suitable for the formation of pharmaceutically acceptable salts from basic compounds are generally known to the person of skill in the art (see for example, The Orange Book, Food & Drug Administration, Washington, D.C.; Stahl et al, (2002), Handbook of Pharmaceutical Salts. Properties, Selection and Use, Camille G. (eds.) Zurich: Wiley-VCH; Berge et al. (1977) J. Pharmaceutical Sci., 66(1), 1-19; Gould, (1986), International J. Pharmaceutics, 33, 201-217; and Anderson et al. (1996), The Practice of Medicinal Chemistry, Academic Press, New York.

Examples of basic salts that may be used or manufactured in accordance with the invention include, but are not limited to: ammonium salts, alkali metal salts (e.g. sodium and potassium salts), alkaline earth metal salts (e.g. calcium and magnesium salts), organic amines (e.g. dicyclohexylamines, t-butyl amines), and amino acid salts (e.g. arginine, lysine). Furthermore, basic nitrogen-containing groups within the compounds or derivatives of the invention may be quarternised with suitable molecules such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides).

Any of the above acid salts and base salts may be pharmaceutically acceptable salts within the context of the invention.

Pharmaceutically acceptable esters of the present compounds also fall within the scope of the invention. Such esters may include any of the following non-limiting groups: (i) carboxylic acid esters obtained by esterification of the hydroxy groups, in which the non-carbonyl moiety of the carboxylic acid portion of the ester grouping is selected from straight or branched chain alkyl (e.g. acetyl, n-propyl, t-butyl, or n-butyl), alkoxyalkyl (e.g. methoxymethyl), aralkyl (e.g. benzyl), aryloxyalkyl (e.g. phenoxymethyl), aryl (e.g. phenyl optionally substituted with, for example, halogen, or $C_1$-$C_4$alkoxy or amino); (ii) sulfonate esters, such as alkyl- or aralkylsulfonyl (e.g. methanesulfonyl); (iii) amino acid esters (e.g. L-valyl or L-isoleucyl); (iv) phosphonate esters; and (v) mono-, di- or triphosphate esters.

The compounds of the invention generally contain asymmetric or chiral centers (such as asymmetric/chiral carbon atoms), and therefore, exist in different stereoisomeric forms. The chiral centres of the compounds of present invention can have either the S or R configuration as defined by the IUPAC 1974 recommendations. It is intended that all stereoisomeric forms of the compounds, salts etc. of the invention are encompassed within the scope of the invention, including mixtures, such as racemic mixtures of the stereoisomeric forms. Geometric isomers of the compounds of the invention are also incorporated: for example, where a compound has a double bond or a fused ring, the cis- and trans-forms of the molecules, as well as mixtures thereof are included. If desired, diastereomeric mixtures of the compounds of the invention may be separated into their individual diastereomers on the basis of their physical chemical differences using methods known in the art. By way of example, chromatographic and/or fractional crystallisation procedures may be used. Enantiomers may be separated, if desired, by use of chiral HPLC column. Alternatively, enantiomeric mixtures may also be separated by converting the mixture into a diastereomeric mixture by reacting with an appropriate optically active compound (e.g. a chiral auxiliary agent, such as a chiral alcohol or Mosher's acid, MTPA or similar agents). The resultant diastereomers can then be separated and converted back to the corresponding pure enantiomers (e.g. by hydrolysis). Positional isomers, such as 4-pyridyl and 3-pyridyl are also considered to fall within the scope of the invention.

Compounds of the invention, including solvates, salts, esters and prodrugs thereof, may also exist in different tautomeric forms (for example: amide and imino ethers; keto-enol and imine-enamine forms). All such tautomeric forms are encompassed within the scope of the invention.

Individual stereoisomers of the compounds of the invention may, for example, be substantially free of other isomers, or may be admixed, for example, as racemates with one or more other stereoisomers. The terms 'salt', 'solvate', 'ester' and 'prodrug' in respect of the compounds of the invention are intended to equally apply to any enantiomers, stereoisomers, rotamers, tautomers, positional isomers, or racemates of the compounds.

Synthesis of Compounds

The compounds of the invention, including the compounds of Formula I may be prepared according to the general reaction Scheme A. Intermediates and starting materials used in the reaction procedures are mostly known compounds, which are commercially available or may be prepared according to art-known procedures. According to some embodiments, both enantiomers of the morpholino core for use in steps A3 and A4 of Scheme A may be prepared according to general reaction Scheme B.

The first steps (B1 and B2) in the synthesis of the morpholin-2-yl methanol intermediates (compounds 54 and 56) of general reaction Scheme B, is to react epichlorohydrin with N-benzylethanolamine to form (4-benzylmorpholin-2-yl) methanol. (R) or (S) stereoisomers as appropriate, are formed using either the (R) or (S) form of epichlorohydrin. The reaction may take place in solution or in an organic solvent, such as a mixture of water and isopropanol. A preferred solvent is 1:1 water/isopropanol. Beneficially, epichlorohydrin may be dissolved in a pre-formed solution of N-benzylethanolamine. Conveniently, the reaction may be performed at room temperature (e.g. between 20 and 25° C.; preferably between 23 and 25° C.), and optionally may be continued at a lower temperature, such as −20° C. At −20° C. the reaction may be continued overnight (e.g. for a further 8 to 16 hours).

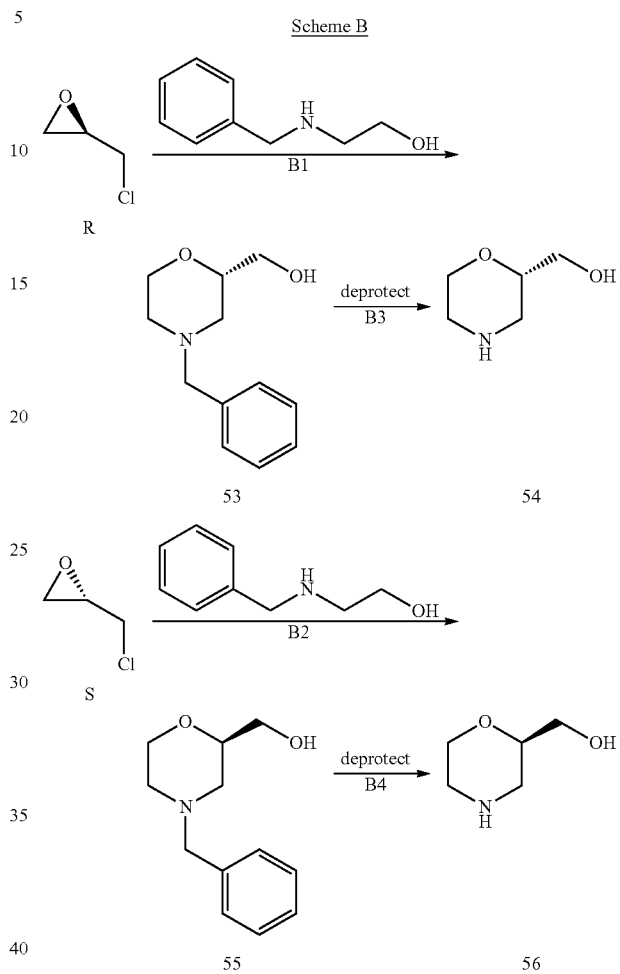

Scheme B

In the next steps (B3 and B4), the intermediate, (4-benzylmorpholin-2-yl)methanol, is deprotected by removing the benzyl moiety so as to form the required morpholin-2-yl-methanol intermediates (compounds 54 and 56). This may be achieved by reducing compounds 53 and 54, e.g. using $H_2$ in the presence of a reduction catalyst, such as a palladium catalyst, and particularly Pd/C. Alternatively Pd(OH)$_2$ may be used as a catalyst. Conveniently, the reduction/deprotection reaction may take place in a solvent, for example, an organic solvent (e.g. methanol).

A more specific protocol for the synthesis of compounds 54 and 56 is depicted in Scheme BB, below.

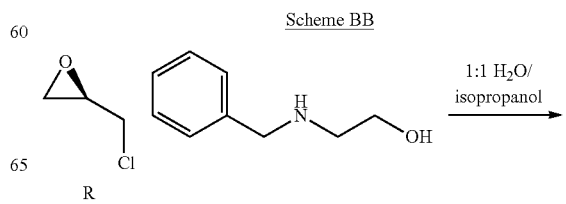

Scheme BB

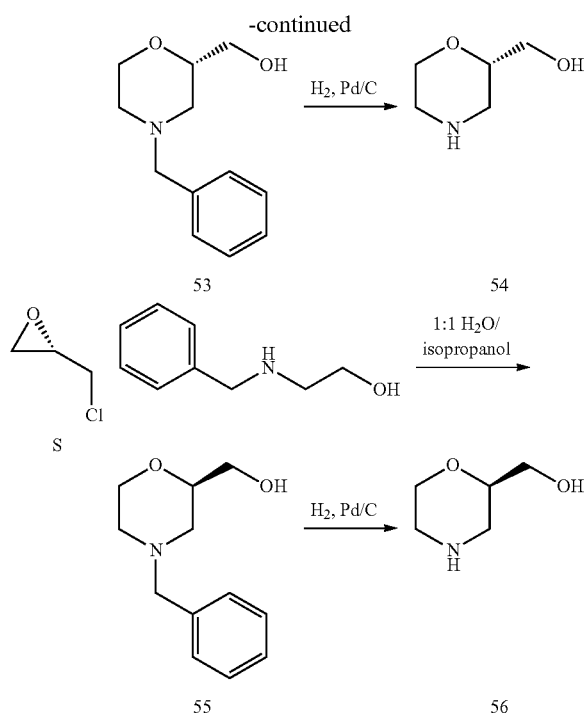

pared (see also Henegar (2008), "Concise Synthesis of (S)—N-BOC-2-Hydroxymethylmorpholine and (S)—N-BOC-Morpholine-2-carboxylic Acid", *J. Organic Chem.*, 73, pp 3662-3665).

In the first step the intermediate of Formula IV where $R^1$ to $R^4$ and $R^8$ are defined elsewhere herein is reacted with chloroacetyl chloride to form the intermediate of Formula V (step A1). The reaction suitably takes place in the presence of a base and/or solvent. Conveniently, the intermediate of Formula IV (e.g. indoline or a substituted derivative thereof) may first be dissolved in an organic solvent, such as dichloromethane (DCM); and a base, such as a tertiary amine (e.g. triethylamine; TEA) may be added. The reaction process may be aided by agitation, e.g. by stirring at room temperature, and the reaction may be quenched using water before the compound of Formula V is extracted.

According to step A3, to prepare the compound of Formula VII, the chloro substituent on the compound of Formula V is replaced by reacting with hydroxymethylmorpholine, which may have been prepared according to reaction Scheme B. Hydroxymethylmorpholine may be in the (R) or (S) configuration, or may be a racemic mixture, according to requirements. To promote the reaction, the mixture of hydroxymethylmorpholine and the compound of Formula V may be heated, suitably in the presence of a base (e.g. a amide) and a solvent. Beneficially the base may be a tertiary amide, such as TEA. Any suitable solvent may be used, such as a polar aprotic solvent, e.g. acetonitrile. A convenient way to heat the reaction mixture is to irradiate the mixture, Reaction Scheme A illustrates exemplary routes by which compounds and intermediates of the invention may be prepared Scheme A

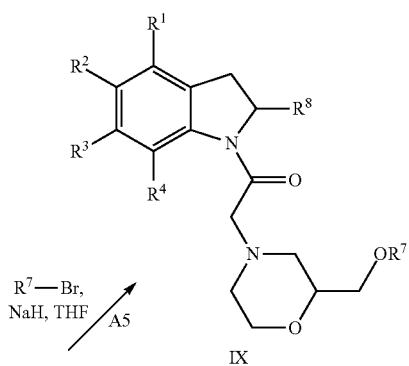

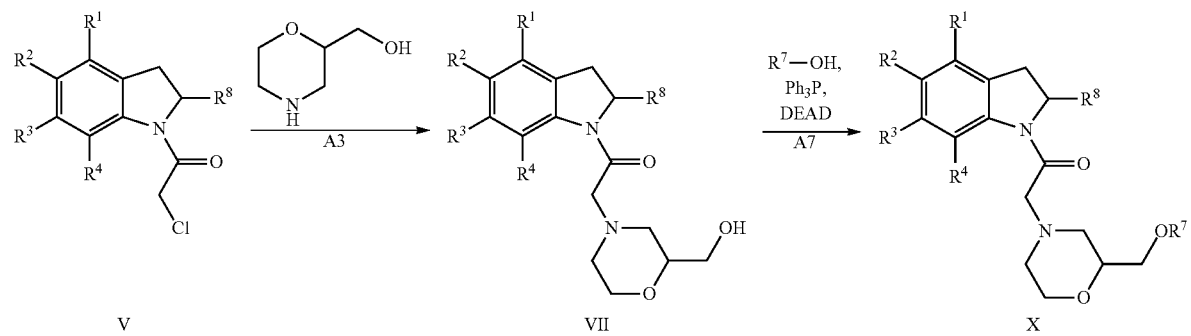

-continued

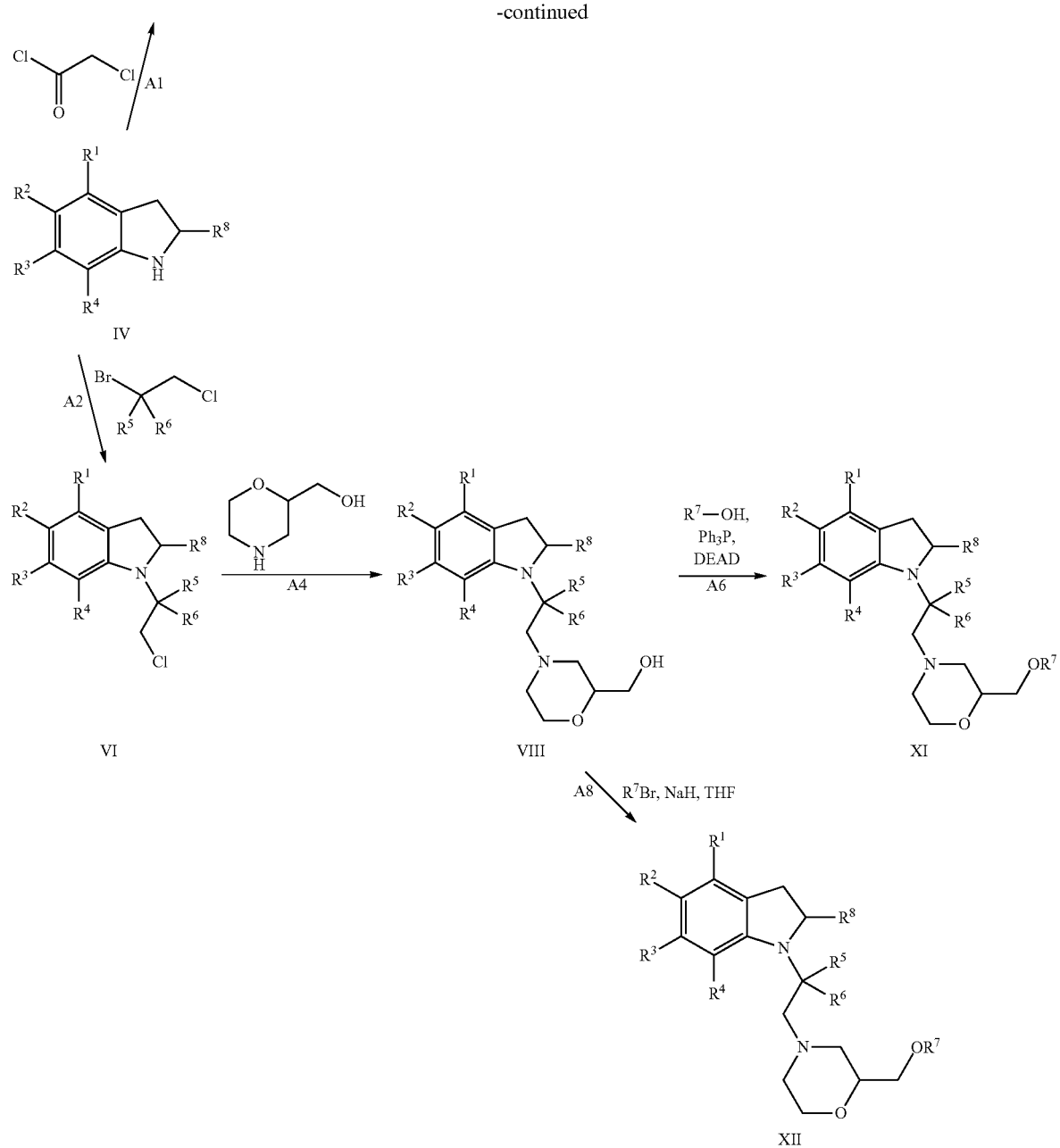

e.g. using a microwave. The mixture may be heated, for example, at 100° C. for a sufficient period of time (e.g. 30 mins).

The intermediate of Formula VII may be converted into the products of Formula IX or Formula X, using the process of step A5 or A7, according to preference. In accordance with step A5, the compound of Formula VII is reacted with a compound of the formula $R^7$—Br, where $R^7$ is as defined elsewhere herein, so that the $R^7$ group replaces the hydrogen of the hydroxyl group on the compound of Formula VII. Suitably, the reaction takes place in the presence of a base and optionally a solvent. Preferably a strong base, such as an alkali metal halide (e.g. NaH) is used. Generally an organic solvent is used, for example, THF. It may be an advantage to heat the reaction mixture, e.g. to at least 100° C. In one embodiment, the reaction mixture is sealed in a microwave vial and irradiated with microwaves to heat it to approximately 170° C., for example, for approximately 1.5 hrs.

The compound of Formula X is prepared by reacting the compound of Formula VII with an alcohol of the formula $R^7$—OH, such as described in Lin et al. (1997), "Structure-Activity Studies on 2-Methyl-3-(2(S)-pyrrolidinylmethoxy) pyridine (ABT-089): An Orally Bioavailable 3-Pyridyl Ether Nicotinic Acetylcholine Receptor Ligand with Cognition-Enhancing Properties", *J. Med. Chem.*, 40, pp 385-390. Suitably, the reaction is a Mitsunobu reaction. The Mitsunobu reaction can be performed in the presence of a trialkyl or triarylphosphine (preferably triphenylphosphine) and a dialkyl azodicarboxylate, such as diethyl azodicarboxylate (DEAD) or di-isopropyl azodicarboxylate (DIAD). In one embodiment, the alcohol, the compound of Formula VII, and the trialkylphosphine are dissolved in a suitable organic solvent, such as THF or diethyl ether. Finally, the dialkyl azocarboxylate is added (preferably also dissolved in the organic solvent). Any suitable reaction conditions can be used, such as (but not limited to) incubation at approximately 0° C. overnight (e.g. up to approximately 17 hrs).

In the lower half of reaction Scheme A, step A2, the intermediate of Formula VI is synthesised from the intermediate of Formula IV by reacting with 2-chloro-1-bromoethane, where $R^1$ to $R^4$ and $R^8$ are defined elsewhere, and $R^5$ and $R^6$ are hydrogen. Suitable the reaction takes place in the presence of a base, such as an amide. Preferred bases are tertiary amides, such as TEA. Generally, a solvent is also used. Useful solvents include polar aprotic solvents, e.g. acetonitrile. To promote the reaction, the mixture may be heated, e.g. by irradiation in a microwave, for example, at approximately 80° C. for a sufficient period of time (e.g. 1 hr). In some cases the reaction may be performed at a temperature of up to 100° C. for a period of up to approximately 12 hrs.

In step A4, the compound of Formula VIII is prepared by reacting the compound of Formula VI with hydroxymethylmorpholine, in a similar (or the same) manner as described in relation to step A3. The hydromethylmorpholine may be prepared according to reaction Scheme B, and may be in the (R) or (S) configuration, or may be a racemic mixture, according to requirements. To promote the reaction, the mixture of hydroxymethylmorpholine and the compound of Formula VI may be heated, suitably in the presence of a base (e.g. an amide) and a solvent. Beneficially the base is a tertiary amide, such as TEA. Any suitable solvent may be used, such as a polar aprotic solvent, e.g. acetonitrile. A convenient way to heat the reaction mixture is to irradiate the mixture, e.g. using a microwave. The mixture may be heated, for example, at 100° C. for a sufficient period of time (e.g. 2 hrs); optionally followed by a higher temperature, such as approximately 120° C. for 40 mins; and optionally followed by a further incubation, such as at approximately 110° C. for 1 hr. In another embodiment, the reaction may be performed at a temperature of approximately 90° C. for a period of up to approximately 3 hrs.

The intermediate of Formula VIII may be converted into the products of Formula XI or Formula XII, using the process of step A6 or A8, respectively, according to preference. Step A6 may be performed in generally the same manner as step A7, described above; while step A8 may be carried out in generally the same manner as that of step A5 already described. The invention further relates to compounds of Formulas IX, X, XI and XII, wherein $R^1$ to $R^8$ are as defined herein.

Specific compounds of the invention can, for example, be prepared following the more specific reaction procedure illustrated in Scheme AA. The person of skill in the art can readily perform the disclosed reaction steps having regard to the teaching provided above, the common general knowledge and the specific protocols described in the Examples.

In each step of the reaction procedure the desired compound may be purified prior to carrying out the next reaction in the procedure. Any suitable means of purification can be used. Generally, purification of intermediates and compounds of the invention is by flash column chromatography. Conveniently, the products of the reaction may be loaded onto a silica gel column and the intermediate or compound of the invention may be eluted using a suitable solvent. The speed/manner in which products are eluted from the column depends on the retention factor (Rf) of the molecule concerned. Often the solvent used to elute the products is a mixture of solvents, which may be applied as a gradient of increasing polarity, so as to elute the products from the column according to their charge. Any suitable solvents or solvent mixtures can be used, such as DCM and/or methanol; hexane and/or ethylacetate. The person of skill in the art is well aware of suitable ways for purifying the compounds of the invention by column chromatography, and alternative ways of purifying chemical compounds.

Scheme AA

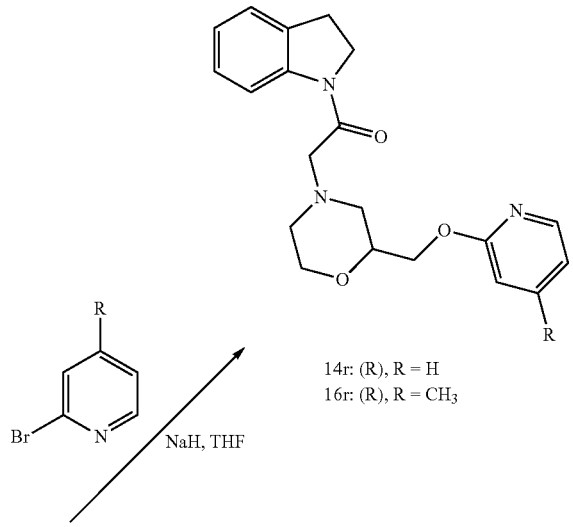

14r: (R), R = H
16r: (R), R = $CH_3$

-continued

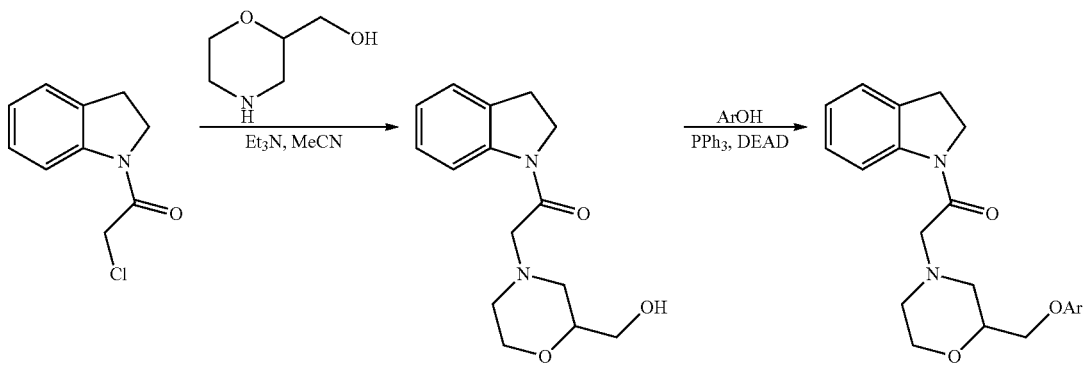

47

48 (S)
49 (R)

18s: (S), Ar = phenyl
20r: (R), Ar = 3-pyridyl
20s: (S), Ar = 3-pyridyl
22r: (R), Ar = 3-chloropyridyl
22s: (S), Ar = 3-chloropyridyl
24s: (S), Ar = 3-methoxyphenyl

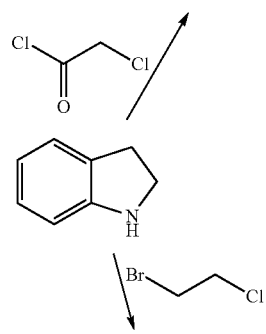

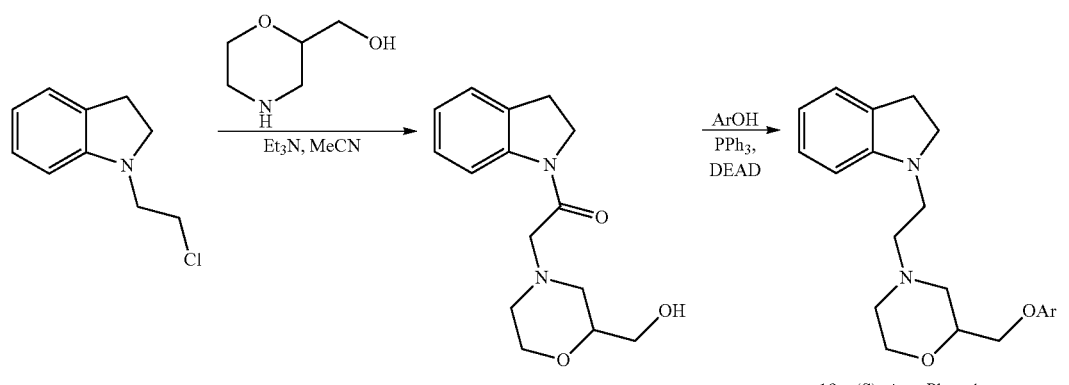

50

51 (S)
52 (R)

19s: (S), Ar = Phenyl
21r: (R), Ar = 3-pyridinyl
21s: (S), Ar = 3-pyridinyl
23r: (R), Ar = 3-chlorophenyl
23s: (S), Ar = 3-chlorophenyl
25r: (R), Ar = 3-methoxyphenyl
25s: (S), Ar = 3-methoxyphenyl
26r: (R), Ar = 2-methylpyridin-3yl
26s: (S), Ar = 2-methylpyridin-3-yl
27r: (R), Ar = 5-chloropyridin-3-yl
27s: (S), Ar = 5-chloropyridin-3-yl
28r: (R), Ar = 4-methylpyridin-3-yl
28s: (S), Ar = 4-methylpyridin-3-yl
29r: (R), Ar = 2,5-dimenthylpyridin-3-y
32s: (S), Ar = 4-fluorophenyl

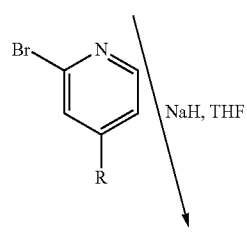

-continued

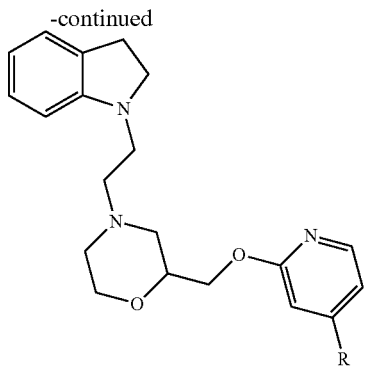

15r: (R), R = H
17r: (R), R = CH₃

Stereoisomers of the compounds of the invention may be resolved (if desired) in any suitable manner, such as by the procedures outlined elsewhere herein. Where the compound of the invention is a racemic mixture any proportion of R and S enantiomers may be present (e.g. between 40:60 and 60:40, such as approximately 50:50). Where the compounds of the invention are pure enantiomers, e.g. R or S stereoisomers, they are preferably at least 80% pure stereoisomer, at least 90% pure stereoisomer, or at least 95% pure stereoisomer. Suitably, a pure stereoisomer is at least 98%, at least 99% or at least 99.9% pure of the other stereoisomer.

The compounds of the invention may also be purified from contaminants using procedures well know in the art, and those described herein. Generally, the isolated compounds of the invention (where pure stereoisomers or racemic) are at least 50% pure from other contaminants (such as reaction bi-products or starting materials). Suitably, compounds of the invention are at least 70%, at least 80%, at least 90% or at least 95% pure. In some preferred embodiments, the compounds of the invention are at least 98%, at least 99% or at least 99.9% pure.

Diseases, Disorders and Medical Conditions

The molecules, compounds, therapeutic agents and pharmaceutical compositions of the invention may be evolved, selected and optimised to have activity against any desired target molecule. Typically, the target molecule is a protein or peptide. The target molecule may be a wild-type or a mutated protein or peptide, such as may be associated with a disease or condition. Beneficially, the disease or condition is in a mammal, and more suitably in a human subject.

Therapeutic uses and applications for the compounds and compositions of the invention include the treatment of various neurological disorders and related conditions; psychological (psychiatric) disorders and related conditions, such as eating disorders; and cancers/neoplastic diseases and related conditions. Neurological disorders include, amongst others: Parkinson's disease, Alzheimer's disease, amyotrophic lateral sclerosis, depression, anxiety, cognitive dysfunction, head injury, spinal cord injury, acute hypertension, meningitis, encephalitis, cerebral malaria, multiple sclerosis, and encephalopathy; Other therapeutic uses for the compounds and compositions of the invention may include the treatment of microbial infections and associated conditions, for example, bacterial, viral, fungal or parasitic infection; diabetic and other proliferative retinopathies; inflammation and inflammatory-related conditions.

The molecule or pharmaceutical may be suitable for single target therapy or for polypharmacology. Suitable target proteins are GPCRs, particularly dopamine and serotonin receptors. The some embodiments the compounds of the invention are directed towards dopamine D4, dopamine D2 and/or serotonin 5HT receptors. Preferred 5HT1 targets for compounds of the invention include 5HT1a. In particularly suitable embodiments, the compounds of the invention are antagonists of the above receptors. In some embodiments the compounds of the invention are beneficially selective for one GPCR; whereas for polypharmacological applications it is advantageous for the compounds of the invention to be selective antagonists of at least two GPCRs, such as dopamine D4 and serotonin 5HT1a.

Antagonists and inverse agonists of dopamine D4 identified in accordance with the invention may be useful in the treatment of diseases and conditions such as schizophrenia, Parkinson's disease, amyotrophic lateral sclerosis, Alzheimer's disease, cognitive dysfunction and/or myoclonus dystonia. Antagonists and inverse agonists of serotonin 5HT1a may be useful in the treatment of diseases and conditions such as anxiety, depression (particularly in combination with SSRI fluoxetine), and for sexual dysfunction (e.g. induced by chronic fluoxetine treatment). In addition, they may be used to enhance cognitive functions, such as learning and memory.

Polypharmacological compounds of the invention are particularly advantageous in treating certain diseases and conditions. By way of example, suitable polypharmacology (multi-target) protein combinations against which molecules of the invention may be optimised include: (1) 5HT1a receptor and dopamine D4 receptor. A compound capable of antagonising 5HT1a and dopamine D4 optionally in combination with an antagonist of dopamine D2 and/or 5HT1d may be useful for treating diseases of cognitive dysfunction, such as schizophrenia, depression, Parkinson's disease and/or Alzheimer's disease; (2) dopamine D3 receptor and dopamine D4 receptor; acetylcholinesterase and dopamine D3 receptor; and acetylcholinesterase and dopamine D4 receptor. An antagonist of the dopamine D3 receptor and/or the dopamine D4 receptor optionally in combination with an inhibitor of acetylcholinesterase may be useful in cognition enhancement; (3) a combination of a 5HT1a receptor agonist and a dopamine D2 receptor antagonist may be useful as an antipsychotic drug; (4) 5HT1a receptor and NERT; 5HT1a receptor and SERT; 5HT1a receptor and NERT and SERT; 5HT1a receptor and dopamine D3 receptor; 5HT1a receptor and dopamine D4 receptor; and 5HT1a receptor and alpha 2A receptor. An antagonist of the 5HT1a receptor and/or the dopamine D3 receptor and/or the dopamine D4 receptor and/or the alpha 2A receptor optionally in combination with an inhibitor of NERT and/or SERT may be useful as an anti-depressive medicament; and (4) acetylcholinesterase and a 5HT1a receptor. An antagonist of the 5HT1a receptor and/or the dopamine D4 receptor optionally in combination with an inhibitor of acetylcholinesterase may be useful in cognition enhancement.

Alternatively, the above or different diseases and disorders may be treated using combinations of the compounds of the invention, each of which has been selected and/or optimised to bind one or more disease target (i.e. compounds having binding affinity and, hence, agonist or antagonist activity). In this case, the invention encompasses suitable combinations of the molecules of the invention to treat any of the above and other diseases or conditions. The invention also encompasses the use of compounds and therapeutics of the invention in combination with other (known) pharmaceutical agents for the treatment of one or more disease or disorder.

Dosage Forms, Medicaments and Pharmaceuticals

The compound, molecule or agent of the invention may be used to treat (e.g. cure, alleviate or prevent) one or more diseases, infections or disorders. Thus, in accordance with the invention, the compounds and molecules may be manufactured into medicaments or may be incorporated or formulated into pharmaceutical compositions.

The molecules, compounds and compositions of the invention may be administered by any convenient route, for example, methods of administration include intradermal, intramuscular, intraperitoneal, intravenous, subcutaneous, intranasal, epidural, oral, sublingual, intranasal, intravaginal, transdermal, rectally, by inhalation, or topically to the skin. Delivery systems are also known to include, for example, encapsulation in liposomes, microgels, microparticles, microcapsules, capsules, etc. Any other suitable delivery system known in the art is also envisioned in use of the present invention. Administration can be systemic or local. The mode of administration may be left to the discretion of the practitioner.

The dosage administered will, of course, vary depending upon known factors, such as the pharmacodynamic properties of the particular active agent; the chosen mode and route of administration; the age, health and weight of the recipient; the nature of the disease or disorder to be treated; the extent of the symptoms; any simultaneous or concurrent treatments; the frequency of treatment; and the effect desired. In general, a daily dosage of active agent of between about 0.001 and about 1000 mg/kg of body weight can be expected. For some applications, the dosage may suitably be within the range of about 0.01 to about 100 mg/kg; or between about 0.1 to about 10 mg/kg. Depending on known factors, such as those noted above, the required dosage of the active agent of the invention may be administered in a single daily dose, or the total daily dosage may be administered in divided doses of two, three, or four times daily.

Dosage forms of the pharmaceutical compositions of the invention suitable for administration may contain from about 1 mg to about 1000 mg of the active ingredient per unit. In such compositions the compound of the invention will ordinarily be present in an amount of about 0.5-95% by weight based on the total weight of the composition.

The 'effective amount' or 'therapeutically effective amount' is meant to describe an amount of compound or a composition of the invention that is effective in curing, inhibiting, alleviating or preventing any of the above-mentioned diseases or disorders, or the amount necessary to achieve a physiological or biochemically-detectable effect. Thus, at the effect amount, the compound or agent is able to produce the desired therapeutic, ameliorative, inhibitory or preventative effect.

When administered to a subject, an agent, including inhibitors and antagonists of the invention is suitably administered as a component of a composition that comprises a pharmaceutically acceptable carrier or vehicle. One or more additional pharmaceutical acceptable carrier (such as diluents, adjuvants, excipients or vehicles) may be combined with the compound of the invention in a pharmaceutical composition. Suitable pharmaceutical carriers are described in "*Remington's Pharmaceutical Sciences*" by E. W. Martin. Pharmaceutical formulations and compositions of the invention are formulated to conform to regulatory standards and according to the chosen route of administration.

Acceptable pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and colouring agents may be used. When administered to a subject, the pharmaceutically acceptable vehicles are preferably sterile. Water is a suitable vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or buffering agents.

The medicaments and pharmaceutical compositions of the invention can take the form of solutions, suspensions, emulsion, tablets, pills, pellets, powders, gels, capsules (for example, capsules containing liquids or powders), modified-release formulations (such as slow or sustained-release formulations), suppositories, emulsions, aerosols, sprays, suspensions, or any other form suitable for use. Other examples of suitable pharmaceutical vehicles are described in Remington's Pharmaceutical Sciences, Alfonso R. Gennaro ed., Mack Publishing Co. Easton, Pa., 19th ed., 1995, see for example pages 1447-1676.

Suitably, the therapeutic compositions or medicaments of the invention are formulated in accordance with routine procedures as a pharmaceutical composition adapted for oral administration (more suitably for humans). Compositions for oral delivery may be in the form of tablets, lozenges, aqueous or oily suspensions, granules, powders, emulsions, capsules, syrups, or elixirs, for example. Thus, in one embodiment, the pharmaceutically acceptable vehicle is a capsule, tablet or pill.

Orally administered compositions may contain one or more agents, for example, sweetening agents such as fructose, aspartame or saccharin; flavouring agents such as peppermint, oil of wintergreen, or cherry; colouring agents; and preserving agents, to provide a pharmaceutically palatable preparation. When the composition is in the form of a tablet or pill, the compositions may be coated to delay disintegration and absorption in the gastrointestinal tract, so as to provide a sustained release of active agent over an extended period of time. Selectively permeable membranes surrounding an osmotically active driving compound are also suitable for orally administered compositions. In these dosage forms, fluid from the environment surrounding the capsule is imbibed by the driving compound, which swells to displace the agent or agent composition through an aperture. These dosage forms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade. For oral formulations, the location of release may be the stomach, the small intestine (the duodenum, the jejunum, or the ileum), or the large intestine. One skilled in the art is able to prepare formulations that will not dissolve in the stomach, yet will release the material in the duodenum or elsewhere in the intestine. Suitably, the release will avoid the deleterious effects of the stomach environment, either by protection of the peptide (or derivative) or by release of the peptide (or derivative) beyond the stomach environment, such as in the intestine. To ensure full gastric resistance a coating impermeable to at least pH 5.0 would be essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac, which may be used as mixed films.

To aid dissolution of the therapeutic agent into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. Potential nonionic detergents that could be included in the formulation as surfactants include: lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants, when used, could be present in the formulation of the compound or derivative either alone or as a mixture in different ratios.

Typically, compositions for intravenous administration comprise sterile isotonic aqueous buffer. Where necessary, the compositions may also include a solubilising agent.

Another suitable route of administration for the therapeutic compositions of the invention is via pulmonary or nasal delivery.

Additives may be included to enhance cellular uptake of the therapeutic agent of the invention, such as the fatty acids oleic acid, linoleic acid and linolenic acid.

The therapeutic agents of the invention may also be formulated into compositions for topical application to the skin of a subject.

Where the invention provides more than one active agent for use in combination, generally, the agents may be formulated separately or in a single dosage form, depending on the prescribed most suitable administration regime for each of the agents concerned.

When the therapeutic agents are formulated separately, the pharmaceutical compositions of the invention may be used in a treatment regime involving simultaneous, separate or sequential administration with the other one or more therapeutic agent. The other therapeutic agent(s) may comprise a compound of the invention or a therapeutic agent known in the art).

The molecules and pharmaceutical compositions of the invention may be formulated and suitable for administration to the central nervous system (CNS) and/or for crossing the blood-brain bather (BBB).

The invention will now be described by way of the following non-limiting examples.

EXAMPLES

Unless otherwise defined, all technical and scientific terms used herein have the same meaning as commonly understood by one of ordinary skill in the art to which this invention belongs.

Commercially available reagents and standard techniques in organic chemistry and biochemistry were generally used.

Unless otherwise specified, the practice of the present invention employs conventional techniques in medicine, pharmacology and biochemistry, which are within the capabilities of a person of ordinary skill in the art. Where common molecular biology techniques are described it is expected that a person of skill in the art would have knowledge of such techniques, for example from standard texts such as Sambrook J. et al., (2001) *Molecular Cloning: a Laboratory Manual*, Cold Spring Harbor Press, Cold Spring Harbor, N.Y.

Example 1

Morpholino Derivatives as Modulators of Dopamine D4, 5HT1a and 5HT1d Receptors

The compounds of the invention are morpholino derivatives, and generally comprise a morpholino moiety linked to an isoindole (or methyl-isoindole) moiety via a linker group. The morpholino group has a substitution, which creates a chiral centre. Individual R and S morpholino enantiomers were synthesised and assayed separately with the chirality designated by the compound number suffix. Direct analogues with and without a carbonyl oxygen in the linker group were also synthesised and assayed. The methyl-isoindole group introduces a second chiral centre and so separate R and S enantiomers were prepared for these compounds as well.

The morpholino analogues were profiled against the panel of 20 GPCRs as described below. These 20 receptors include 12 serotonin receptors, 3 alpha1 adreno-receptors and five dopamine receptors. In general, the compounds of the prior art are unable to clearly distinguish between some of these closely related receptors, meaning that a specific-binding interaction between a compound and a desired GPCR is extremely difficult to achieve.

The receptor binding data for the synthesised compounds against the 20 receptors are displayed in Table 1.

TABLE 1

Experimental Receptor Binding Data - Ki (nM). Data is the average of at least two experiments.

| Compound | 5HT1a | 5HT1b | 5HT1d | 5HT1e | 5HT2a | 5HT2b | 5HT2c | 5HT3 | 5HT4 | 5HT5 |
|---|---|---|---|---|---|---|---|---|---|---|
| 14r | 7324 | — | — | — | — | — | — | — | — | — |
| 15r | 2883 | — | — | — | — | 600 | — | — | — | — |
| 16r | 2298 | — | — | — | — | — | — | — | — | — |

TABLE 1-continued

Experimental Receptor Binding Data - Ki (nM). Data is the average of at least two experiments.

|  |  |  |  |  |  |  |  |  |  |  |
|---|---|---|---|---|---|---|---|---|---|---|
| 17r | — | — | — | — | — | 788 | — | — | — | — |
| 18s | — | — | — | — | — | 6416 | — | — | — | — |
| 19s | 0.6 | — | 590 | — | 817 | 1445 | 6736 | — | — | — |
| 20r | — | — | — | — | 2663 | 8808 | — | — | — | — |
| 20s | — | — | — | — | — | 7641 | — | — | — | — |
| 21r | — | — | — | — | 3584 | — | — | — | — | — |
| 21s | 10000 | — | — | — | — | 3545 | — | — | — | — |
| 22r | 384 | — | — | — | 2066 | 2358 | — | — | — | — |
| 22s | 1388 | 7765 | — | — | 2718 | 1096 | — | — | — | — |
| 23r | 1848 | — | — | — | 2671 | 1846 | — | — | — | — |
| 23s | 545 | — | 1121 | — | 1275 | 551 | 3386 | — | — | — |
| 24s | 371 | 4827 | — | — | 1945 | 1654 | — | — | — | — |
| 25r | 1469 | — | — | — | 3779 | 2692 | — | — | — | — |
| 25s | 174 | — | 1976 | — | 1399 | 658 | 3763 | — | — | — |
| 26r | — | — | — | — | — | 3169 | — | — | — | — |
| 26s | — | — | — | — | — | — | — | — | — | — |
| 27r | — | — | — | — | — | 2561 | — | — | — | — |
| 27s | — | — | — | — | — | — | — | — | — | — |
| 28r | — | — | — | — | 1482 | — | — | — | — | — |
| 28s | — | — | — | — | — | — | — | — | — | — |
| 29r | — | — | — | — | >10000 | 1326 | — | — | — | — |
| 32s | — | — | — | — | — | 374 | — | 1108 | — | — |
| 60 | 592 | — | — | — | — | 4607 | — | — | — | — |
| 61 | 540 | — | — | — | — | — | — | — | — | — |
| 62 | 6591 | — | — | — | — | 5179 | — | — | — | — |
| 63 | 5024 | — | — | — | — | — | — | — | — | — |
| 64 | 644 | — | — | — | 4537 | 441 | — | — | — | — |
| 65 | >10000 | — | — | — | 1815 | 333 | — | — | — | — |
| 66 | 7535 | — | — | — | — | 770 | — | — | — | — |
| 67 | >10000 | — | — | — | — | — | — | — | — | — |
| 68 | >10000 | — | — | — | — | — | — | — | — | — |
| 69 | >10000 | — | — | — | — | — | — | — | — | — |
| 70 | 6374 | — | — | — | — | 3463 | 6374 | — | — | — |

| Compound | 5HT6 | 5HT7 | Alpha1A | Alpha1B | Alpha1D | D1 | D2 | D3 | D4 | D5 |
|---|---|---|---|---|---|---|---|---|---|---|
| 14r | — | — | — | — | — | — | — | — | — | — |
| 15r | — | — | — | — | — | — | — | >10000 | 814 | — |
| 16r | — | — | — | — | — | >10000 | — | — | — | — |
| 17r | — | — | — | — | — | >10000 | — | — | 1931 | — |
| 18s | — | — | — | — | — | — | — | — | 5526 | — |
| 19s | — | 468 | 2720 | 7211 | 2307 | 1353 | 342 | 2827 | 132 | — |
| 20r | — | — | — | — | — | — | — | — | — | — |
| 20s | — | — | — | — | — | — | — | — | — | — |
| 21r | — | — | — | — | — | >10000 | — | — | 2406 | — |
| 21s | — | — | — | — | — | >10000 | >10000 | 8359 | 182 | >10000 |
| 22r | — | — | — | — | — | — | — | — | 536 | — |
| 22s | — | — | — | — | — | — | — | — | 2858 | — |
| 23r | — | — | — | — | — | — | >10000 | — | 1666 | — |
| 23s | — | — | 9037 | 6637 | 4181 | 2041 | 1892 | 6645 | 146 | — |
| 24s | — | — | — | — | — | — | — | — | — | — |
| 25r | — | — | — | — | — | — | — | — | 2486 | — |
| 25s | — | — | 8350 | — | 6448 | 8366 | 10000.0 | 8286 | 3362 | 8526 |
| 26r | — | >10000 | — | — | — | — | — | >10000 | — | — |
| 26s | — | — | — | — | — | — | — | — | 435 | — |
| 27r | — | — | — | — | — | — | — | — | 3618 | — |
| 27s | — | — | — | — | — | 5852 | >10000 | — | 90 | — |
| 28r | — | — | — | — | — | — | — | — | — | — |
| 28s | — | — | — | — | — | — | — | — | 503 | — |
| 29r | — | — | — | — | — | — | — | — | 4947 | — |
| 32s | — | — | — | — | — | — | — | — | 3926 | — |
| 60 | — | — | — | — | — | >10000 | — | — | — | — |
| 61 | — | — | — | — | >10000 | >10000 | — | — | — | — |
| 62 | — | — | — | — | — | — | — | — | — | — |
| 63 | — | — | — | — | — | — | — | — | — | — |
| 64 | — | — | — | — | >10000 | — | — | — | 2394 | — |
| 65 | — | — | — | — | >10000 | — | — | — | — | — |
| 66 | — | — | — | — | >10000 | — | — | — | — | — |
| 67 | — | — | — | — | — | — | — | — | — | — |
| 68 | — | — | — | — | — | — | — | — | — | — |
| 69 | — | — | — | — | — | — | — | — | — | — |
| 70 | — | — | — | — | — | >10000 | — | — | — | — |

"—" indicates that a binding interaction was not detected.

In general, the assay results confirmed that the morpholino compounds of the invention can be highly selective for dopamine D4 over all the other receptors tested. 17 of the compounds tested had affinities for the dopamine D4 receptor that ranged from a $K_i$ of 5526 nM (compound 18s) to only 90 nM (compound 27s). Eight of the compounds exhibited affinity for the D4 receptor with a K, or less than 1000 nM (compounds 15r, 19s, 21s, 22r, 23s, 26s, 27s and 28s).

Some of the compounds also (or alternatively) exhibited potent binding activity against other receptors. For example, compound 19s was a strong binder of 5HT1a and of dopamine D4 (5HT1a, $K_i$=0.6 nM; dopamine D4, $K_i$, =132 nM).

The compounds could be generally sub-divided into those that contained an ethyl linker between the morpholine and isoindole groups, and those that contained an ethanone linker; and between those that contained an 2-methyl-isoindole moiety and those that did not. Compounds containing the ethyl linker group are generally although not exclusively found to have even stronger activity against the dopamine D4 receptor. Compounds containing the 2-methyl-isoindole moiety are generally although not exclusively found to have even stronger binding activity against the serotonin 5HT1a receptor.

For compounds with the ethyl linker in particular, the data suggests that the S enantiomer may be more potent than the R entantiomer.

Further functional assays against the dopamine D2 and dopamine D4 receptors were also carried out on the selected compounds (e.g. compounds 21s and 22r), data not shown, and these indicated that the morpholino compounds may act as inverse agonists of the dopamine D2 and D4 receptors. These data also served to further confirm that the morpholino analogues of the invention are effective D4 antagonists.

Any "off-target" trends for the analysed compounds can be observed in the profiling data (Table 1). As shown, 10 of the morpholino compounds show some off-target activity at 5HT1a; although only two of the dopamine D4 active compounds have higher affinity for 5HT1a than dopamine D4. Thus, the data demonstrates that generally the compounds of the invention have improved selectivity for their target GPCRs compared with some prior art compounds.

Compounds 22r, 24s, 19s and 25s, in particular, demonstrate promising utility as agonists or antagonists of the 5HT1a receptor, or as lead compounds for the development of improved agonists or antagonists of 5HT1a or related receptors. Compounds 19s (5HT1a $K_i$=0.6 nM) and 25s (5HT1a $K_i$=174 nM) show particularly high activity in this regard, since both of them bind to the 5HT1a receptor with higher affinity than any of the other 19 receptors used in the tests.

In addition, the 2-methylindoline derivatives appear to have utility are agonists or antagonists of the 5HT1a receptor. In particular, compounds 60, 61 and 64 all bind the 5HT1a receptor with Ki<1000 nM. Furthermore, compounds 60 and 61 show excellent selectivity for the 5HT1a receptor over the other GPCRs tested.

Compounds 21s, 19s, 23s, 25s, 26s and 27s may have particular utility as antagonists or reverse agonists of the dopamine D4 receptor, or as lead compounds for the development of improved antagonists of dopamine D4 or related receptors. Of those tested, compound 26s appears to be the most selective, with no measured affinities for any of the other related receptors screened (dopamine D4 $K_i$=434.7 nM). Four compounds possess both relatively high affinity for dopamine D4 (i.e. $K_i$<1 μM), and two or fewer off-target activities out of the 20 GPCRs profiled (i.e. compounds 21s, 26s, 27r, 28s). Compounds 27s (dopamine D4 $\underline{K}_i$=90 nM; dopamine D1 $K_i$=5852 nM) and 21s (D4 $K_i$=182 nM; $5HT_{2A}$ $K_i$=3545 nM) may be particularly useful as therapeutic molecules or a lead compounds, in view of their high affinity and selectivity for the dopamine D4 receptor, with relatively low affinity for each of the other 19 receptors used in the assays.

Compound 32s is a particularly promising candidate as an agonists or antagonists of the 5HT2a receptor, or as lead compounds for the development of improved agonists or antagonists of 5HT2a or related receptors.

Compounds 23s and 25s show the highest affinity for the receptor 5HT2b, and therefore, these compounds may be useful in the treatment of, or as intermediates in the preparation of therapeutic agents for the treatment of 5HT2b-related disorders, such as cardiovascular diseases (Roth (2007), "Drugs and valvular heart disease" *N. Engl. J. Med.,* 356, pp 6-9). In a functional 5HT2b assay, data not shown, compound 23s was demonstrated to function as an agonist of the receptor (Emax: 69.6% of 5HT2b activity, pEC50 of 6.21).

In summary, the morpholino derivatives of the invention show excellent selectivity for dopamine D4 over other key related GPCR targets. For example, on average the morpholino compounds bind to 3.4 targets (of which one is dopamine D4) with $K_i$<10 μM); which compares favourably to an average of 15.8 targets per compound for the isoindole and benzolactam compounds designed to target the dopamine D4 receptor, as described in our co-pending patent application PCT/GB2010/051940 (see Examples 1 and 2 described therein). Advantageously, 7 of the active morpholino derivatives of the invention have off-target activities for only 1 of the 20 receptors tested.

In optimising a lead compound, such as 27s, to a pre-clinical drug derivative of the lead compound it is sometimes necessary to decrease hERG affinity and possibly also increase metabolic stability by blocking metabolically labile sites, whilst maintaining the beneficial pharmacological profile. Therefore, hERG and metabolic stability assays were conducted to further assess the utility of the compounds of the invention as potential therapeutic agents or lead compounds. Thus, a PatchXpress assay was carried out (see hERG assay described below), and the results showed that some weak hERG inhibition was present for compound 27s (pEC50=5.51+/−0.13) and 21s (pEC50=5.82+/−0.25). The results of the metabolic stability assay for compound 27s (mouse hepatic microsomal Cli, =25 mL/min/g for 27s) suggest that morpholino derivatives of the invention may further benefit from the blocking of some metabolically labile sites, in order to increase the metabolic stability.

In a brain penetration assay, compound 27s was demonstrated to penetrate into the CNS with an in vivo brain/blood ratio of 2.0.

The morpholino-isoindole analogues of the invention represent a new chemotype for dopamine D4 ligands and, thus, may have utility as new therapeutic compounds. In particular, the dopamine D4 selective morpholino compounds and their derivatives of the invention have great potential for the treatment of cognitive dysfunction in diseases such as schizophrenia, amyotrophic lateral sclerosis and other indications in mental health, such as bipolar disorder, addictive behaviours, and eating disorders as described elsewhere. They may also have utility in the treatment of diseases such as Parkinson's disease and/or Alzheimer's diseases.

Furthermore, the serotonin 5HT1a antagonists and their derivatives of the invention may be useful in the treatment neurological disorders, anxiety, depression, and/or in sexual dysfunction. The 5HT1a antagonists of the invention may be particularly useful when used in combination with other therapeutic agents, such as fluoxetine-based medicaments.

Also, the serotonin 5HT2b binding compounds and their derivatives of the invention may be useful in the treatment of cardiovascular diseases.

Assay Methods

1. Secondary Radioligand Binding Assays

The detailed experimental protocols for the radioligand and functional receptor assays are available on the NIMH PDSP website at http://pdsp.med.unc.edu/UNC-CH%20Protocol%20Book.pdf.

A. Serotonin receptors: 5-HT1A, 5-HT1B, 5-HT1D, 5-HT1E, 5-HT2A, 5-HT2B, 5-HT2C, 5-HT3, 5-HT5A, 5-HT6 and 5-HT7

Assay Buffer: Standard Binding Buffer (50 mM Tris-HCl, 10 mM $MgCl_2$, 1 mM EDTA, pH 7.4)

Membrane Fraction Source: Transiently or stably transfected cell lines (e.g., HEK293, COS, CHO, NIH3T3)

Protocol adapted from Roth et al. (1986), *J. Pharmacol. Exp. Ther.*, 238(2): 480-485; and Roth et al. (1994), *J. Pharmacol. Exp. Ther.*, 268(3): 1403-1410.

Experimental Procedure and Data Analysis

A solution of the compound to be tested is prepared as a 1 mg/ml stock in Standard Binding Buffer or DMSO according to its solubility. A similar stock of a reference compound (positive control) is also prepared. Eleven dilutions (5× assay concentration) of the test and reference (see Table 19) compounds are prepared in Standard Binding Buffer by serial dilution: 0.05 nM, 0.5 nM, 1.5 nM, 5 nM, 15 nM, 50 nM, 150 nM, 500 nM, 1.5 µM, 5 µM, 50 µM (thus, the corresponding assay concentrations span from 10 pM to 10 µM and includes semilog points in the range where high-to-moderate affinity ligands compete with radioligand for binding sites).

Radioligand is diluted to five times the assay concentration (see Table 18) in Standard Binding Buffer. Typically, the assay concentration of radioligand is a value between one half the KD and the KD of a particular radioligand at its target. 50 µl aliquots of radioligand are dispensed into the wells of a 96-well plate containing 100 µl of Standard Binding Buffer. Then, duplicate 50 µl aliquots of the test and reference compound dilutions are added.

Finally, crude membrane fractions of cells expressing recombinant target (prepared from 10 cm plates by harvesting PBS-rinsed monolayers, resuspending and lysing in chilled, hypotonic 50 mM Tris-HCl, pH 7.4, centrifuging at 20,000× g, decanting the supernatant and storing at −80° C.; typically, one 10 cm plate provides sufficient material for 24 wells), are resuspended in 3 ml of chilled Standard Binding Buffer and homogenized by several passages through a 26 gauge needle, then 50 µl are dispensed into each well.

The 250 µl reactions are incubated at room temperature and shielded from light (to prevent photolysis of light-sensitive ligands) for 1.5 hours, then harvested by rapid filtration onto Whatman GF/B glass fiber filters pre-soaked with 0.3% polyethyleneimine using a 96-well Brandel harverster. Four rapid 500 µl washes are performed with chilled Standard Binding Buffer to reduce non-specific binding. Filters are placed in 6 ml scintillation tubes and allowed to dry overnight. The next day, 4 ml of EcoScint scintillation cocktail (National Diagnostics) are added to each tube. The tubes are capped, labeled, and counted by liquid scintillation counting. For higher throughput assays, bound radioactivity is harvested onto 0.3% polyethyleneimine-treated, 96-well filter mats using a 96-well Filtermate harvester. The filter mats are dried, then scintillant is melted onto the filters and the radioactivity retained on the filters is counted in a Microbeta scintillation counter.

Raw data (dpm) representing total radioligand binding (i.e. specific+non-specific binding) are plotted as a function of the logarithm of the molar concentration of the competitor (i.e. test or reference compound). Non-linear regression of the normalised (i.e. percent radioligand binding compared to that observed in the absence of test or reference compound) raw data is performed in Prism 4.0 (GraphPad Software) using the built-in three parameter logistic model describing ligand competition binding to radioligand-labeled sites:

$$y=\text{bottom}+[(\text{top}-\text{bottom})/(1+10x-\log IC50)]$$

where bottom equals the residual radioligand binding measured in the presence of 10 µM reference compound (I.e. non-specific binding) and top equals the total radioligand binding observed in the absence of competitor. The log IC50 (i.e. the log of the ligand concentration that reduces radioligand binding by 50%) is thus estimated from the data and used to obtain the Ki by applying the Cheng-Prusoff approximation:

$$Ki=IC50/(1+[\text{ligand}]/KD)$$

where [ligand] equals the assay radioligand concentration and KD equals the affinity constant of the radioligand for the target receptor.

TABLE 19

Serotonin (5-HT) receptor radioligands, radioligand assay concentrations, and reference compounds

| Receptor | Radioligand (Assay Conc.) | Reference Compound |
|---|---|---|
| 5-HT1A | [3H]8-OH-DPAT (0.5 nM) | Methysergide |
| 5-HT1B | [3H]GR125743 (0.3 nM) | Ergotamine |
| 5-HT1D | [3H]GR125743 (0.3 nM) | Ergotamine |
| 5-HT1E | [3H]5-HT (3 nM) | 5-HT |
| 5-HT2A | [3H]Ketanserin (0.5 nM) | Chlorpromazine |
| 5-HT2B | [3H]LSD (1 nM) | 5-HT |
| 5-HT2C | [3H]Mesulergine (0.5 nM) | Chlorpromazine |
| 5-HT3 | [3H]LY278584 (0.3 nM) | LY278584 |
| 5-HT5A | [3H]LSD (1 nM) | Ergotamine |
| 5-HT6 | [3H]LSD (1 nM) | Chlorpromazine |
| 5-HT7 | [3H]LSD (1 nM) | Chlorpromazine |

B. Dopamine Receptors: D1, D2, D3, D4, D5

Assay Buffers: Dopamine Binding Buffer (50 mM NaCl, 50 mM HEPES-HCl, 5 mM $MgCl_2$, 0.5 mM EDTA, pH 7.4)

Membrane Fraction Source: Transiently or stably transfected cell lines (e.g. HEK293, COS, CHO, NIH3T3)

Protocol adapted from Roth et al. (1995), *Psychopharmacology* 120(3): 365-368.

Experimental Procedure and Data Analysis

The method is carried out in the manner described for the serotonin receptor assay above. Eleven dilutions (5× assay concentration) of the test and reference (see Table 19) compounds are prepared in Dopamine Binding Buffer by serial dilution, as previously described. Radioligand is diluted to five times the assay concentration (see Table 20) in Dopamine Binding Buffer.

TABLE 20

Dopamine receptor radioligands, radioligand assay concentrations, and reference compounds

| Receptor | Radioligand (Assay Conc.) | Reference Compound |
|---|---|---|
| D1 | [3H]SCH23390 (0.2 nM) | SKF38393 |
| D2 | [3H]N-methylspiperone (0.2 nM) | Haloperidol |
| D3 | [3H]N-methylspiperone (0.2 nM) | Chlorpromazine |
| D4 | [3H]N-methylspiperone (0.3 nM) | Chlorpromazine |
| D5 | [3H]SCH23390 (0.2 nM) | SKF38393 |

C. Adrenergic Receptors: α1A, α1B, α2A, α2B, α2C, β1, β2, β3

Assay Buffers: For α1 receptors, α1 Binding Buffer (20 mM Tris-HCl, 145 mM NaCl, pH 7.4); for α2 receptors, α2 Binding Buffer (50 mM Tris-HCl, 5 mM $MgCl_2$, pH 7.7); for β receptors, β Binding Buffer (50 mM Tris-HCl, 3 mM $MnCl_2$, pH 7.7)

Membrane Fraction Source: Transiently or stably transfected cell lines (e.g. HEK293, COS, CHO, NIH3T3)

Protocol adapted from Arango et al. (1993), *Brain Res.,* 630(1-2): 271-282; and Arango et al. (1990), *Gen. Psychiatry,* 47: 1038-1047.

Experimental Procedure and Data Analysis

The method is carried out in the manner described for the serotonin receptor assay above, except where described below. Eleven dilutions (5× assay concentration) of the test and reference (see Table 20) compounds are prepared in the appropriate buffer by serial dilution, as previously described. Radioligand is diluted to five times the assay concentration (see Table 21) in the appropriate buffer.

The 250 µl reactions are incubated at room temperature and shielded from light (to prevent photolysis of light-sensitive ligands) for 1 hour (for α1 receptors, 40 min for α2 receptors, and 1.5 hours for β receptors), then harvested by rapid filtration onto Whatman GF/B glass fiber filters pre-soaked with 0.3% polyethyleneimine using a 96-well Brandel harvester. Four rapid 500-µl washes are performed with chilled distilled water (for α1 and β receptors) or 0.1% polyethyleneimine (for α2 receptors) to reduce non-specific binding. Filters are placed in 6 ml scintillation tubes and allowed to dry overnight and the samples are treated to obtain data as described above.

TABLE 21

Adrenergic receptor radioligands, radioligand assay concentrations, and reference compounds

| Receptor | Radioligand (Assay Conc.) | Reference Compound |
|---|---|---|
| α1A | [125I]HEAT (0.1 nM) | Urapidil |
| α1B | [125I]HEAT (0.1 nM) | Corynanthine |
| α2A | [125I]Iodoclonidine (0.1 nM) | Oxymetazoline |
| α2B | [125I]Iodoclonidine (1 nM) | Prazosin |
| α2C | [125I]Iodoclonidine (1 nM) | Prazosin |
| β1 | [125I]Iodopindolol (0.1 nM) | Alprenolol |
| β2 | [125I]Iodopindolol (0.1 nM) | Alprenolol |
| B3 | [125I]Iodopindolol (0.1 nM) | Alprenolol |

2. hERG Assay hERG activity was assayed by the patch clamp method on a PatchXpress platform and by FluxOR T1+ assays. Assays were performed as previously described (Huang, et al. (2010), "Identification of human Ether-à-go-go related gene modulators by three screening platforms in an academic drug-discovery setting", *Assay Drug Dev. Technol.* 8, pp 727-742).

3. Metabolic Stability Assay (In Vitro)

Metabolic stability was assessed, generating the in vitro intrinsic clearance (Cli) following incubation of test compound with mouse hepatic microsomes. The assay was performed as previously described (Ruda et al. (2010), "Aryl Phosphoramidates of 5-phosho erythronohydroxamic acid, a new class of potent trypanocidal agents", *J. Med. Chem.* 53, pp 6071-6078).

Briefly, each test compound (0.5 µM) was incubated with pooled female mouse liver microsomes (Tebu-Bio, UK; 0.5 mg/ml 50 mM potassium phosphate buffer, pH7.4) and the reaction started with addition of excess NADPH (8 mg/ml 50 mM potassium phosphate buffer, pH7.4) Immediately, at time zero, then at 3, 6, 9, 15 and 30 minutes an aliquot (50 µl) of the incubation mixture was removed and mixed with acetonitrile (100 µl) to stop the reaction. Internal standard was added to all samples. The samples were centrifuged to sediment precipitated protein and the plates then sealed prior to UPLCMSMS analysis using a Quattro Premier XE (Waters, USA).

XLfit (IDBS, UK) was used to calculate the exponential decay and consequently the rate constant (k) from the ratio of peak area of test compound to internal standard at each time-point. The rate of intrinsic clearance (CLi) of each compound was then calculated using the following equation (1):

$$CLi(\text{ml/min/g liver}) = k \times V \times \text{Microsomal protein yield} \quad (1)$$

where V (ml/mg protein) is the incubation volume/mg protein added and microsomal protein yield is taken as 52.5 mg protein/g liver.

Verapamil was used as a positive control to confirm acceptable assay performance.

4. Assessment of Brain Penetration

Brain penetration was assessed, determining the ratio of tested compound between brain and blood at a set time point following intravenous administration to mice.

Test compound was dosed intravenously at 1 mg free base/kg to female NMRI mice (n=3 mice/compound). Dose formulation was 10% DMSO:90% saline and dose volume was 5 ml/kg. Each mouse was placed under terminal anaesthesia with isofluorane at 5 minutes post-dose. Blood was taken by cardiac puncture into two volumes distilled water and the brain removed. After suitable sample preparation, the concentration of test compound in blood and brain was determined by UPLCMSMS using a Quattro Premier XE (Waters, USA) and the brain:blood ratio determined Example 2

(S)-(4-benzylmorpholin-2-yl)methanol (Compound 53)

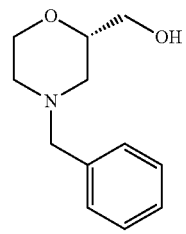 [SMILES: OC[C@@H]1CN(Cc2ccccc2)CCO1]

(R)-epichlorohydrin (1.7 ml, 21.6 mmol) was added to a solution of N-benzylethanolamine (3.73 ml, 25.7 mmol) in 1:1 water/isopropanol (7 ml), keeping the temperature between 20 and 25° C. After 6 hours the milky suspension was stored at −20° C. overnight. The solution was warmed to room temperature and 40% tetraethylammonium hydroxide (TEAOH) in water (12.3 ml) was added. The mixture was stirred at 20° C. for 1 hour and then quenched with 1M HCl (4 ml), keeping the pH around 10. The suspension was diluted with water (7 ml) and extracted with dichloromethane (DCM; 3×13 ml). The combined organic portions were dried and concentrated. The residue (yellowish oil) was purified by flash chromatography eluting the silica with DCM/MeOH 1:0 to 92:8. The product was isolated from the low Rf (slow-eluting) fraction as a colourless oil (2.3 g; 52% yield).

$^1$H-NMR (500 MHz, $CDCl_3$) δ: 2.03 (dd+bs, 2H, J=11.5, 9.9 Hz, O$\underline{H}$+C$\underline{H}$HN), 2.22 (dt, 1H, J=11.5, 3.3 Hz, C$\underline{H}$HN), 2.68-2.73 (m, 2H, CH$_2$N), 3.53 (AB syst., 2H, CH$_2$-Ph), 3.56-3.71 (m, 3H, CH$_2$OCHCH$_2$), 3.73 (dt, 1H, J=11.2, 2.5 Hz, CHHOH), 3.91-3.94 (m, 1H, CHHOH), 7.27-7.30 (m, 1H, ArH), 7.33-7.35 (m, 4H, ArH).

$^{13}$C-NMR (125 MHz, CDCl$_3$) δ: 53.1, 54.6, 63.4, 64.3, 66.7, 76.0, 127.2, 128.3, 129.2, 137.6.

LCMS: m/z 208.14 ([M+H]$^+$, 100%); Rt 3.6 min, purity >99% DAD (180-450 nm).

Example 3

(S)-morpholin-2-ylmethanol (Compound 54)

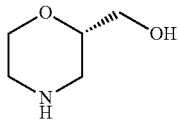

Compound 53 (960 mg, 4.61 mmol) was stirred for 4 hours under the pressure of 50 psi of hydrogen in the presence of 10% Pd/C (200 mg) in methanol (10 ml). After filtration through a celite pad and evaporation of the solvents, compound 54 was isolated as a colourless oil (478 mg; 88%).

$^1$H-NMR (500 MHz, CDCl$_3$) δ: 2.57 (bs, 2H, NH+OH), 2.69-2.72 (m, 1H, CHHN), 2.85-2.90 (m, 3H, CH$_2$N+CHHN), 3.48-3.63 (m, 3H, CH$_2$OCHCH$_2$), 3.66 (dt, 1H, J=11.5, 3.3 Hz, CHHOH), 3.90-3.93 (m, 1H, CHHOH).

$^{13}$C-NMR (125 MHz, CDCl$_3$) δ: 45.66, 47.33, 64.00, 67.66, 76.78.

LCMS: m/z 117.09 ([M+H]$^+$, 100%); Rt 0.5 min, purity >99% DAD (180-450 nm).

Example 4

(R)-(4-benzylmorpholin-2-yl)methanol (Compound 55)

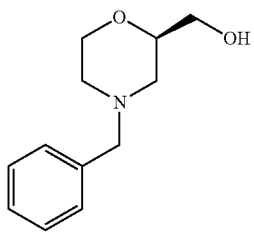 [SMILES: OC[C@H]1CN(Cc2ccccc2)CCO1]

Compound 55 was synthesised using essentially the same procedure as compound 53 (Example 2). (S)-epichlorohydrin (2.5 g, 2.70 mmol), N-benzylethanolamine (3.73 ml, 2.60 mmol), TEAOH (12.3 ml). The product was obtained as a colourless oil (2.7 g; 50%).

For $^1$H and $^{13}$C NMR data see compound 53

LCMS: m/z 208.1 ([M+H]$^+$, 100%); Rt 3.8 min, purity >99% DAD (180-450 nm).

Example 5

(R)-morpholin-2-ylmethanol (Compound 56)

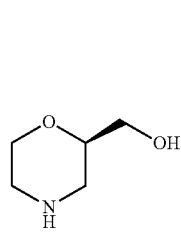

Compound 56 was synthesised using essentially the same procedure as compound 54 (Example 3), starting from compound 55 (1.4 g), 10% Pd/C (350 mg), MeOH (15 ml). After filtration through a celite pad and evaporation of the solvents, compound 56 was obtained as a colourless oil (712 mg, yield 88%).

For $^1$H and $^{13}$C NMR data see compound 54

Example 6

2-Chloro-1-(indolin-1-yl)ethanone (Compound 47)

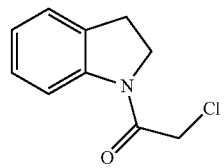 [SMILES: O=C(CCl)N1CCc2ccccc21]

Chloroacetyl chloride (0.37 ml, 4.6 mmol) was added to a solution of indoline (0.47 ml, 4.19 mmol) and triethylamine (TEA; 0.70 ml, 5.03 mmol) in dichloromethane (DCM; 15 ml). The mixture was stirred for 3 hrs at room temperature (RT) and then quenched with water (5 ml). The phases were separated and the aqueous layer was extracted with DCM (3×5 ml). The combined organic layers were dried over MgSO$_4$ and concentrated to a dark brown residue, 1 g (quantitative), which was used for the next step without further purification.

$^1$H-NMR (500 MHz, CDCl$_3$) δ: 3.27 (t, 2H, J=8.3 Hz, CH$_2$), 4.17-4.21 (m, 4H, CH$_2$Cl+CH$_2$N), 7.09 (dt, 1H, J=7.5, 1.0 Hz, ArH), 7.22-7.27 (m, 2H, ArH), 8.24 (d, 1H, J=8.1 Hz, ArH).

$^{13}$C-NMR (125 MHz, CDCl$_3$) δ: 28.2, 43.1, 47.9, 117.4, 124.5, 124.6, 127.7, 131.1, 142.5, 163.9.

LCMS: m/z 196.06 ([M+H]$^+$, 100%); Rt 4.8 min, purity >99% DAD (180-450 nm).

Example 7

(S)-2-(2-(Hydroxymethyl)morpholino)-1-(indolin-1-yl)ethanone (Compound 48)

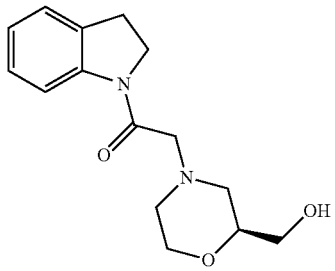 [SMILES: O=C(CN1CCO[C@H](CO)C1)N1CCc2ccccc21]

A microwave vial was charged with 1-(chloroacetyl)-indoline (compound 47; 390 mg, 2.00 mmol), hydroxymethylmorpholine (compound 54; 280 mg, 2.39 mmol), triethylamine (0.55 ml, 4.00 mmol) and acetonitrile (2 ml). The vial was sealed and irradiated for 30 min at 100° C. The crude mixture was purified by flash column chromatography (silica, DCM/MeOH 1:0 to 92:8). The product was obtained as a white solid (435 mg; yield 79%).

$^1$H-NMR (500 MHz, CDCl$_3$) δ: 1.97 (bs, 1H, OH), 2.23 (t, 1H, J=10.5 Hz, 1 of 1 of (CH$_2$)$_2$N), 2.40 (dt, 1H, J=11.0, 3.0 Hz, 1 of (CH$_2$)$_2$N), 2.88 (t, 2H, J=13.0 Hz, 1 of (CH$_2$)$_2$N), 3.23 (t, 2H, J=8.3 Hz, 1 of CH$_2$N), 3.29 (AB syst, 2H, ArCH$_2$), 3.56-3.69 (m, 2H, CH$_2$OH), 3.74-3.82 (m, 2H, COCH$_2$N), 3.94-3.97 (m, 1H, CHCH$_2$), 4.18 (t, 2H, J=8.5 Hz, CONCH$_2$), 7.06 (dt, 1H, J=7.4, 1.0 Hz, ArH), 7.21-7.24 (m, 2H, ArH), 8.25 (d, 1H, J=8.1 Hz, ArH).

$^{13}$C-NMR (125 MHz, CDCl$_3$) δ: 28.3, 47.4, 53.3, 54.8, 62.7, 64.1, 66.5, 75.9, 117.1, 123.9, 124.5, 127.6, 167.2.

LCMS: m/z 277.1 ([M+H]$^+$, 100%); Rt 4.2 min, purity >99% DAD (180-450 nm).

Example 8

(R)-2-(2-(hydroxymethyl)morpholino)-1-(indolin-1-yl)ethanone (Compound 49)

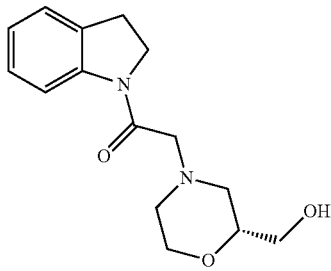 [SMILES: O=C(CN1CCO[C@@H](CO)C1)N1CCc2ccccc21]

Essentially the same procedure was used as for compound 48 with 1-(chloroacetyl)-indoline (compound 47; 471 mg, 2.41 mmol), compound 56 (341 mg, 2.90 mmol), triethylamine (0.67 ml, 4.83 mmol) and acetonitrile (5 ml). The residue was purified by flash chromatography eluting from silica with DCM/MeOH 1:0 to 92:8. The product was obtained as a white solid (376 mg; 56%).

$^1$H-NMR (500 MHz, CDCl$_3$) δ: 1.97 (bs, 1H, OH), 2.23 (t, 1H, J=10.5 Hz, 1 of 1 of (CH$_2$)$_2$N), 2.40 (dt, 1H, J=11.2, 3.2 Hz, 1 of (CH$_2$)$_2$N), 2.88 (t, 2H, J=12.8 Hz, 1 of (CH$_2$)$_2$N), 3.23 (t, 2H, J=8.4 Hz, 1 of CH$_2$N), 3.26-3.33 (m, 2H, ArCH$_2$), 3.58-3.83 (m, 4H, CH$_2$OH+COCH$_2$N), 3.91-3.97 (m, 1H, CHCH$_2$), 4.18 (t, 2H, J=8.2 Hz, CONCH$_2$), 7.05 (dt, 1H, J=7.4, 1.0 Hz, ArH), 7.21-7.24 (m, 2H, ArH), 8.25 (d, 1H, J=13.0 Hz, ArH).

LCMS: m/z 277.1 ([M+H]$^+$, 100%); Rt 4.3 min, purity >94% DAD (180-450 nm).

Example 9

1-(2-chloroethyl)indoline (Compound 50)

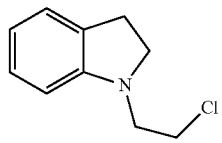 [SMILES: ClCCN1CCc2ccccc21]

A microwave vial was charged with indoline (0.5 g, 4.19 mmol), 2-chloro-1-bromoethane (0.502 ml, 6.25 mmol), TEA (0.7 ml, 6.25 mmol) and acetonitrile (10 ml). The vial was irradiated with microwaves for 1 hour at 80° C. The mixture was diluted with DCM and washed with water (1×10 ml). The organic layer was dried and concentrated and the residue was purified by flash column chromatography (silica, Hexane/EtOAc 95:5 to 0:1). The product was isolated as a violet solid (400 mg; 52%).

$^1$H-NMR (500 MHz, CDCl$_3$) δ: 2.93 (t, 2H, J=8.4 Hz, CH$_2$), 3.35-3.43 (m, 4H, CH$_2$CH$_2$), 3.60 (t, 2H, J=6.8 HZ, CH$_2$), 6.40 (d, 1H, J=7.7 Hz, ArH), 6.59 (dt, 1H, J=7.4, 0.9 Hz, ArH), 6.89-7.01 (m, 2H, ArH).

$^{13}$C-NMR (125 MHz, CDCl$_3$) δ: 28.6, 41.5, 51.4, 53.5, 106.5, 117.9, 124.6, 127.4, 129.6, 151.6.

LCMS: m/z 182.1 ([M+H]$^+$, 100%); Rt 5.3 min, purity >96% DAD (180-450 nm).

Example 10

(S)-(4-(2-(Indolin-1-yl)ethyl)morpholin-2-yl)methanol (Compound 51)

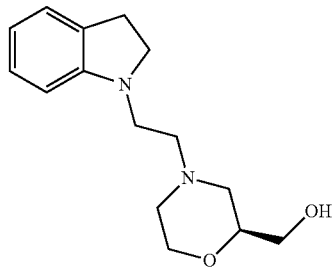 [SMILES: OC[C@@H]1CN(CCN2CCc3ccccc32)CCO1]

A microwave vial was charged with 1-(chloroethyl)-indoline (compound 50; 724 mg, 4.00 mmol), hydroxymethylmorpholine (compound 54; 562 mg, 4.80 mmol), triethylamine (2.2 ml, 16.00 mmol) and acetonitrile (4 ml). The vial was irradiated with microwaves for 2 hrs at 100° C., 40 min at 120° C. and 1 hr at 110° C. The residue was purified by flash column chromatography (silica, DCM/MeOH 1:0 to 8:2); and the product was isolated as an off-white solid (347 mg; 33%).

¹H-NMR (500 MHz, CDCl₃) δ: 2.01 (bs, 1H, OH), 2.12 (t, 1H, J=10.8 Hz, 1 of 1 of (CH₂)₂N), 2.28 (dt, 1H, J=11.4, 3.3 Hz, 1 of (CH₂)₂N), 2.64 (dt, 2H, J=7.5, 2.7 Hz, CH₂N), 2.81 (t, 2H, J=11.5 Hz, 2 of (CH₂)₂N), 2.99 (t, 2H, J=8.3 Hz, CH₂N), 3.26 (t, 2H, J=8.3 Hz, 1 of CH₂N), 3.43 (t, 2H, J J=8.3 Hz, ArCH₂), 3.56-3.78 (m, 4H, CH₂, COCH₂N), 3.94-3.97 (m, 1H, CHCH₂), 6.50 (d, 1H, J=7.7 Hz, ArH), 6.67 (dt, 1H, J=7.3, 0.8 Hz, ArH), 7.07-7.10 (m, 2H, ArH).

¹³C-NMR (125 MHz, CDCl₃) δ: 28.7, 46.9, 53.3, 53.7, 55.2, 56.32, 64.3, 66.7, 75.8, 106.7, 117.2, 124.5, 127.3, 129.8, 152.3.

LCMS: m/z 263.1356 ([M+H]⁺, 100%); Rt 4.3 min, purity >96% DAD (180-450 nm).

Example 11

(R)-(4-(2-(Indolin-1-yl)ethyl)morpholin-2-yl)methanol (Compound 52)

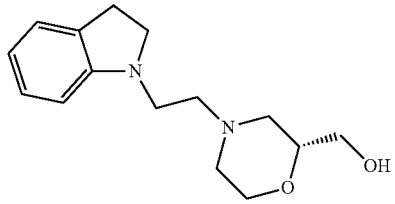 [SMILES: OC[C@H]1CN(CCN2CCc3ccccc32)CCO1]

Essentially the same procedure was followed as for compound 51 with 1-(chloroethyl)-indoline (compound 50; 1.93 g, 10.67 mmol), hydroxymethylmorpholine (compound 56; 1.50 g, 12.8 mmol), triethylamine (5.87 ml, 42.7 mmol) and acetonitrile (10 ml). The product was purified as an off-white solid (882 mg; 32%).

For ¹H and ¹³C NMR data see compound 51.

Example 12

(R)-1-(Indolin-1-yl)-2-(2-((pyridin-2-yloxy)methyl)morpholino)ethanone (Compound 14r)

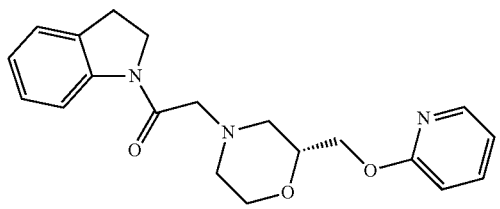 [SMILES: O=C(CN1CCO[C@@H](COc2ccccn2)C1)N1CCc2ccccc21]

Compound 49 (76 mg, 0.28 mmol) and NaH (13 mg, 0.55 mmol) were placed in a microwave vial. Dry THF (2 ml) was added and the mixture was stirred at room temperature (RT) for 5 min before 2-bromopyridine (52 μl, 0.55 mmol) was added. The vial was sealed and irradiated with microwaves for 1.5 hours at 170° C. After this time the solvent was removed and the crude mixture purified by flash column chromatography (Silica, Hex/EtOAc 7:3 to 0:1) to afford compound 14r (22 mg, 23%). Analyses were performed on free base, which was converted to the HCl salt for testing.

¹H-NMR (500 MHz, CDCl₃) δ: 2.28 (apparent t, 1H, J=10.7 Hz, 1 of (CH₂)₂N), 2.42 (td, 1H, J=11.3, 2.9 Hz, 1 of (CH₂)₂N), 2.85 (d, 1H, J=11.3 Hz, 1 of (CH₂)₂N), 3.00 (d, 1H, J=10.7 Hz, 1 of (CH₂)₂N), 3.19 (t, 2H, J=8.4 Hz, ArCH₂CH₂N), 3.24-3.32 (2H, COCH₂), 3.80 (td, 1H, J=11.3, 2.3 Hz, 1 of OCH₂CH₂), 3.92-3.98 (m, 1H, 1 of OCH₂CH₂), 3.98-4.06 (m, 1H, OCH), 4.08-4.21 (m, 2H, ArCH₂CH₂N), 4.31-4.38 (m, 2H, OCH₂CH), 6.76-6.81 (m, 1H, ArH), 6.85 (ddd, 1H, J=7.1, 5.1, 0.9 Hz, ArH), 6.99-7.05 (m, 1H, ArH), 7.16-7.22 (m, 2H, ArH), 7.54 (ddd, 1H, J=8.4, 7.1, 2.0 Hz, ArH), 8.11 (ddd, 1H, J=5.1, 2.0, 0.7 Hz, ArH), 8.23 (d, 1H, J=8.0 Hz, ArH).

¹³C-NMR (125 MHz, CDCl₃) δ: 28.2, 47.5, 53.1, 55.4, 62.8, 66.6, 66.7, 74.1, 111.3, 116.9, 117.1, 123.9, 124.5, 127.6, 131.0, 138.6, 143.0, 146.7, 163.4, 167.2.

LCMS: m/z 354.1803 ([M+H]⁺, 100%); Rt 4.8 min DAD (180-450 nm).

HRMS: Found 354.1802 C₂₀H₂₃N₃O₃ [M+H]⁺ requires 354.1812.

Example 13

(R)-4-(2-(Indolin-1-yl)ethyl)-2-((pyridin-2-yloxy)methyl)morpholine (Compound 15r)

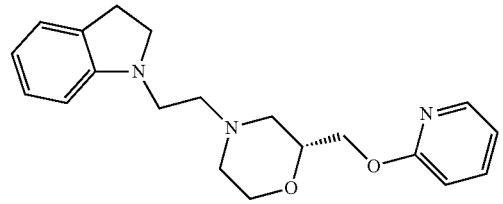 [SMILES: c1ccc(OC[C@H]2CN(CCN3CCc4ccccc43)CCO2)nc1]

Compound 52 (76 mg, 0.29 mmol) and NaH (13.9 mg, 0.58 mmol) were place in a microwave vial. Dry THF (2 ml) was added and the mixture was stirred at RT for 5 min before 2-bromopyridine (55 μl, 0.58 mmol) was added. The vial was sealed and irradiated with microwaves for 1.5 hours at 170° C. After this time the solvent was removed and the crude mixture purified by flash column chromatography (Silica, Hex/EtOAc 1:0 to 0:1) to afford compound 15r as a slightly yellow oil (71 mg, 72%). Analyses were performed on the free base, and it was re-purified (39.4 mg, purity >99%). and converted to the HCl salt for testing.

¹H-NMR (500 MHz, CDCl₃) δ: 2.11-2.21 (m, 1H, 1 of (CH₂)₂N), 2.30 (td, 1H, J=11.3, 3.2 Hz, 1 of (CH₂)₂N), 2.64 (t, 2H, J=7.1 Hz, N(CH₂)₂N), 2.81 (m, 1H, 1 of (CH₂)₂N), 2.92-3.00 (m, 3H, ArCH₂CH₂N+1 of (CH₂)₂N), 3.25 (t, 2H, J=7.1 Hz, N(CH₂)₂N), 3.37-3.45 (m, 2H, ArCH₂CH₂N), 3.76 (td, 1H, J=11.3, 2.1 Hz, 1 of OCH₂CH₂), 3.93-4.02 (m, 2H, OCH+1 of OCH₂CH₂), 4.33-4.38 (m, 2H, OCH₂CH), 6.48 (d, 1H, J=7.7 Hz, ArH), 6.65 (t, 1H, J=7.3 Hz, ArH), 6.81 (dd, 1H, J=8.3, 0.7 Hz, ArH), 6.84-6.89 (1H, m, ArH), 7.03-7.11 (m, 2H, ArH), 7.53-7.61 (m, 1H, ArH), 8.09-8.19 (m, 1H, ArH).

¹³C-NMR (125 MHz, CDCl₃) δ: 28.7, 46.9, 53.4, 53.7, 55.7, 56.3, 66.8, 66.9, 74.1, 106.8, 111.4, 117.0, 117.6, 124.5, 127.3, 129.9, 138.6, 146.7, 152.3, 163.5.

LCMS: m/z 340.2004 ([M+H]⁺, 100%); Rt 5.3 min, purity >93% DAD (180-450 nm).

HRMS: Found 340.2004 $C_{20}H_{25}N_3O_2$ $[M+H]^+$ requires 340.2020.

Example 14

(R)-1-(Indolin-1-yl)-2-(2-4(4-methylpyridin-2-yl)oxy)methyl)morpholino)ethanone (Compound 16r)

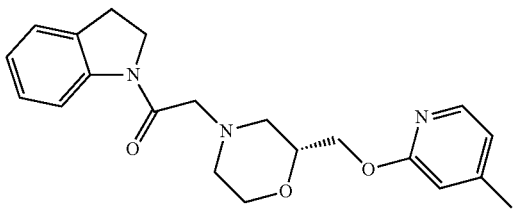 [SMILES: Cc1ccnc(OC[C@H]2CN(CC(=O)N3CCc4ccccc43)CCO2)c1]

Essentially the same procedure was followed for the synthesis of compound 16r as for compound 14r (Example 12), using 2-bromo-4-methylpyridine (92 µl, 0.83 mmol). The crude mixture was purified by column chromatography (silica, Hex/EtOAc 7:3 to 0:1) to afford compound 16r (29 mg, 29%). Analyses were performed on the free base, and it was converted to the HCl salt for testing.

$^1$H-NMR (500 MHz, CDCl$_3$)*: 2.23-2.30 (m, 4H, 1 of (CH2)2N+Me), 2.40 (td, 1H, J=11.1, 2.8 Hz, 1 of (CH2)2N), 2.85 (d, 1H, J=11.1 Hz, 1 of (CH2)2N), 2.99 (d, 1H, J=11.0 Hz, 1 of (CH2)2N), 3.18 (t, 2H, J=8.4 Hz, ArCH2CH2N), 3.23-3.31 (m, 2H, COCH2), 3.78 (td, 1H, J=11.3, 2.2 Hz, 1 of OCH2CH2), 3.91-3.97 (m, 1H, 1 of OCH2CH2), 3.97-4.04 (m, 1H, OCH), 4.08-4.20 (m, 2H, ArCH2CH2N), 4.28-4.36 (m, 2H, OCH2CH), 6.60 (s, 1H, ArH), 6.65-6.69 (m, 1H, ArH), 6.98-7.04 (m, 1H, ArH), 7.15-7.22 (m, 2H, ArH), 7.96 (d, 1H, J=5.2 Hz, ArH), 8.22 (d, 1H, J=8.0 Hz, ArH).

$^{13}$C-NMR (125 MHz, CDCl$_3$)*: 20.9, 28.2, 47.4, 53.1, 55.4, 62.7, 66.5, 66.7, 74.1, 111.3, 117.1, 118.5, 123.9, 124.5, 127.5, 131.0, 143.0, 146.2, 149.9, 163.8, 167.2.

LCMS: m/z 368.1964 ($[M+H]^+$, 100%); Rt 4.9 min DAD (180-450 nm).

HRMS: Found 368.1964 C21H25N3O3 $[M+H]^+$ requires 368.1969.

Example 15

(R)-4-(2-(Indolin-1-yl)ethyl)-2-(((4-methylpyridin-2-yl)oxy)methyl)morpholine (Compound 17r)

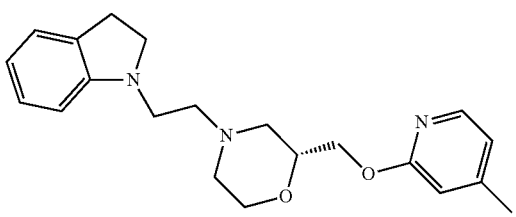 [SMILES: Cc1ccnc(OC[C@H]2CN(CCN3CCc4ccccc43)CCO2)c1]

Essentially the same procedure was followed for the synthesis of compound 17r as for compound 15r (Example 13), with 2-bromo-4-methylpyridine (96 µl, 0.86 mmol) instead of 2-bromopyridine. The crude mixture was purified by column chromatography (silica, Hex/EtOAc 1:0 to 0:1) to afford compound 17r (82 mg, 80%). Analyses were performed on the free base, and it was converted to the HCl salt for testing.

$^1$H-NMR (500 MHz, CDCl$_3$) δ: 2.10-2.18 (m, 1H, 1 of (CH$_2$)$_2$N), 2.35-2.33 (m, 4H, Me+1 of (CH$_2$)$_2$N), 2.63 (t, 2H, J=7.1 Hz, N(CH$_2$)$_2$N), 2.77-2.83 (m, 1H, 1 of (CH$_2$)$_2$N), 2.92-2.99 (m, 3H, ArCH$_2$CH$_2$N+1 of (CH$_2$)$_2$N), 3.22-3.28 (m, 2H, N(CH$_2$)$_2$N), 3.35-3.45 (m, 2H, ArCH$_2$CH$_2$N), 3.75 (td, 1H, J=11.4, 2.4 Hz, 1 of OCH$_2$CH$_2$), 3.93-4.00 (m, 2H, OCH+1 of OCH$_2$CH$_2$), 4.29-4.37 (m, 2H, OCH$_2$CH), 6.48 (d, 1H, J=7.7 Hz, ArH), 6.62-6.67 (m, 2H, ArH), 6.68-6.71 (m, 1H, ArH), 7.03-7.09 (m, 2H, ArH), 7.99 (d, 1H, J=5.2 Hz, ArH).

$^{13}$C-NMR (125 MHz, CDCl$_3$) δ: 20.9, 28.6, 46.9, 53.4, 53.7, 55.7, 56.3, 66.7, 68.8, 74.1, 106.8, 111.4, 117.6, 118.6, 124.4, 127.3, 129.9, 146.2, 150.0, 152.3, 163.8.

LCMS: m/z 354.2173 ($[M+H]^+$, 100%); Rt 4.3 min, purity >96% DAD (180-450 nm).

HRMS: Found 354.2173 $C_{21}H_{27}N_3O_2$ $[M+H]^+$ requires 354.2176.

Example 16

(S)-1-(Indolin-1-yl)-2-(2-(phenoxymethyl)morpholino)ethanone (Compound 18s)

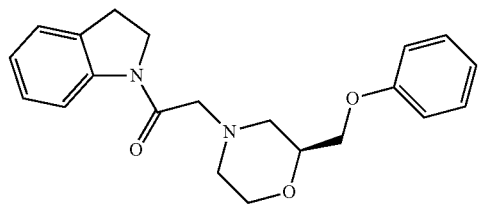 [SMILES: O=C(CN1CCO[C@H](COc2ccccc2)C1)N1CCc2ccccc21]

Compound 18s was prepared following the procedure described in Lin et al. (1997), "Structure-Activity Studies on 2-Methyl-3-(2(S)-pyrrolidinylmethoxy)pyridine (ABT-089): An Orally Bioavailable 3-Pyridyl Ether Nicotinic Acetylcholine Receptor Ligand with Cognition-Enhancing Properties", *J. Med. Chem.*, 40, pp 385-390. Compound 48 (Example 9; 55 mg, 0.2 mmol) and triphenylphosphine (78 mg, 0.3 mmol) were dissolved in dry THF (1 ml). Next diethyl azodicarboxylate (DEAD; 0.05 ml, 0.3 mmol) and phenol (28 mg, 0.3 mmol) were added. The reaction mixture was stirred at RT for approximately 48 hours. The crude residue was purified twice by flash chromatography to afford the title compound as a colourless oil (44 mg; 62%). Analyses were performed on the free base, and it was converted to the HCl salt for testing.

$^1$H-NMR (500 MHz, CD$_3$OD) δ: 3.29 (t, 2H, J=8.2 Hz. ArCH$_2$), 3.37-3.42 (m, 2H, CH$_2$N), 3.70 (bs, 1H, 1 of (CH$_2$)$_2$N), 3.85 (bs, 1H, 1 of (CH$_2$)$_2$N), 4.05-4.24 (m, 6H, ArCH$_2$CH$_2$+CH$_2$N+CH$_2$O), 4.30-4.44 (m, 3H, CHCH$_2$+CH$_2$O), 6.97-6.99 (m, 3H, ArH), 7.12 (dt, 1H, J=7.4, 0.7 Hz, ArH), 7.22 (d, 1H, J=7.5 Hz, ArH), 7.28-7.32 (m, 3H, ArH), 8.17 (d, 1H, J=8.2 Hz, ArH).

$^{13}$C-NMR (125 MHz, CDCl$_3$) δ: 28.7, 46.9, 53.4, 53.7, 56.0, 56.3, 66.9, 69.1, 74.1, 76.8, 106.8, 114.6, 117.6, 121.0, 124.5, 127.3, 129.5, 129.9, 152.3, 158.7.

Example 17

(S)-4-(2-(Indolin-1-yl)ethyl)-2-(phenoxymethyl)morpholine (Compound 19s)

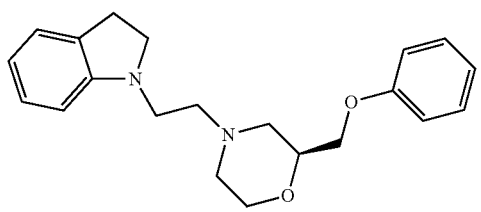 [SMILES: c1ccc(OC[C@@H]2CN(CCN3CCc4ccccc43)CCO2)cc1]

Compound 19s was synthesised by essentially the same procedure as compound 18s (Example 16), using compound 51 (Example 12; 52 mg, 0.2 mmol), phenol (28 mg, 0.3 mmol), triphenylphosphine (78 mg, 0.3 mmol), DEAD (0.05 ml, 0.3 mmol), THF (1 ml). The crude residue was purified twice by flash chromatography to afford the title compound as a colourless oil (28 mg; 41%). Analyses were performed on the free base, and it was converted to the HCl salt for testing.

$^1$H-NMR (500 MHz, CDCl$_3$) δ: 2.06-2.10 (m, 1H, 1 of (CH$_2$)$_2$N), 2.34 (dt, 1H, J=11.3, 3.3 Hz, 1 of (CH$_2$)$_2$N), 2.68 (t, 2H, J=6.9 Hz, 2 of N(CH$_2$)$_2$N), 2.83 (dd, 1H, J=13.1, 1.9 Hz, 1 of (CH$_2$)$_2$N), 2.98-3.03 (m, 3H, ArCH$_2$+1 of (CH$_2$)$_2$N), 3.28 (t, 2H, J=7.4 Hz, 2 of N(CH$_2$)$_2$N), 3.43 (dt, 2H, J=8.3, 1.8 Hz, ArCH$_2$CH$_2$N), 3.79 (dt, 1H, J=11.3, 2.5 Hz, 1 of OCH$_2$CH$_2$), 3.95-4.01 (m, 3H, OCH+1 of OCH$_2$CH$_2$), 4.05-4.09 (m, 1H, 1 of OCH$_2$CH), 6.52 (d, 1H, J=7.6 Hz, ArH), 6.67 (dt, 1H, J=7.4, 0.9 Hz, ArH), 6.94-7.00 (m, 3H, ArH), 7.07-7.10 (m, 2H, ArH), 7.28-7.32 (m, 2H, ArH).

$^{13}$C-NMR (125 MHz, CDCl$_3$) δ: 28.7, 46.9, 53.4, 53.7, 55.9, 56.0, 56.3, 66.9, 69.4, 73.9, 76.8, 106.8, 113.1, 115.1, 117.6, 121.2, 124.5, 127.4, 129.9, 130.2, 134.9, 152.3, 159.4.

HRMS: Found 339.2072 C$_{21}$H$_{27}$N$_2$O$_2$ [M+H]$^+$ requires 339.2067.

Example 18

(R)-1-(Indolin-1-yl)-2-(2-((pyridin-3-yloxy)methyl)morpholino)ethanone (Compound 20r)

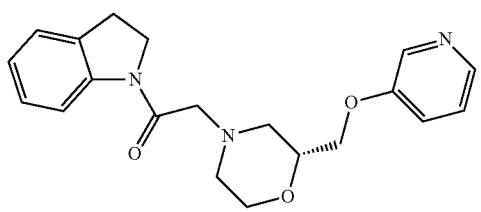 [SMILES: O=C(CN1CCO[C@@H](COc2cccnc2)C1)N1CCc2ccccc21]

Compound 20r was produced using essentially the same procedure as compound 18s (Example 18), with DIAD substituted for DEAD. Compound 49 (Example 10; 90 mg, 0.326 mmol) and triphenylphosphine (128 mg, 0.49 mmol) were dissolved in dry THF (1 ml). Next di-isopropyl azodicarboxylate (DIAD; 0.10 ml, 0.49 mmol) and 3-hydroxypyridine (46 mg, 0.49 mmol) were added. The reaction mixture was stirred at RT for approximately 48 hours. The crude residue was purified twice by flash chromatography (silica, DCM/MeOH 1:0 to 8:2) to afford the title compound as a colourless oil (6 mg; 5%). Analyses were performed on the free base, and it was converted to the HCl salt for testing.

$^1$H-NMR (500 MHz, CDCl$_3$) δ: 2.35 (t, 1H, J=10.5 Hz, 1 of 1 of (CH$_2$)$_2$N), 2.48 (dt, 1H, J=12, 3.8 Hz, 1 of (CH$_2$)$_2$N), 2.89 (d, 1H, J=12 Hz, 1 of (CH$_2$)$_2$N), 3.08 (d, 1H, J=11 Hz, 1 of (CH$_2$)$_2$N), 3.24 (t, 2H, J=8.5 Hz, 1 of ArCH$_2$), 3.31-3.33 (m, 2H, COCH$_2$N), 3.85 (dt, 1H, J=11.2, 2.4 Hz, 1 of CHCH$_2$OAr), 3.97-4.14 (m, 4H, CH$_2$OCHCH$_2$+1 of CH$_2$OAr), 4.18-4.21 (m, 2H, ArCH$_2$CH$_2$), 7.06 (dt, 1H, J=7.4, 1.0 Hz, ArH), 7.21-7.24 (m, 4H, ArH), 8.26 (d, 1H, J=7.9 Hz, ArH), 8.36 (bs, 1H, ArH).

$^{13}$C-NMR (125 MHz, CDCl$_3$) δ: 28.3, 47.5, 53.1, 55.3, 62.6, 66.8, 69.4, 73.9, 117.1, 121.3, 123.9, 124.6, 127.6, 138.1, 142.5, 167.1.

LCMS: m/z 556.2 ([M+H]$^+$, 100%); Rt 5.0 min, purity >99% DAD (180-450 nm).

Example 19

(R)-4-(2-(Indolin-1-yl)ethyl)-2-((pyridin-3-yloxy)methyl)morpholine (Compound 21r)

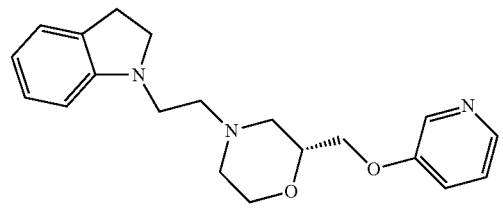 [SMILES: c1cncc(OC[C@H]2CN(CCN3CCc4ccccc43)CCO2)c1]

Using essentially the same procedure as for compound 20r, compound 52 (Example 13; 80 mg, 0.30 mmol) and PPh$_3$ (120 mg, 0.46 mmol) were dissolved in dry THF (1.5 ml). Next DIAD (90 µl, 0.46 mmol, 1.5 eq.) and 3-hydroxypyridine (44 mg, 0.46 mmol, 1.5 eq.) were added. The reaction mixture was stirred at RT for approximately 48 hours. After this time, the solvent was removed and the crude mixture purified by flash column chromatography (Silica, DCM/MeOH 1:0 to 94:6) to afford KA159 as a colourless oil (61 mg, 59%). Analyses were performed on the free base, which was converted to the HCl salt for testing.

$^1$H-NMR (500 MHz, CDCl$_3$) δ: 2.14-2.21 (m, 1H, 1 of (CH$_2$)$_2$N), 2.31 (td, 1H, J=11.3, 3.3 Hz, 1 of (CH$_2$)$_2$N), 2.66 (t, 2H, J=7.1 Hz, N(CH$_2$)$_2$N), 2.79-2.83 (m, 1H, 1 of (CH$_2$)$_2$N), 2.93-3.01 (m, 3H, ArCH$_2$CH$_2$N+1 of (CH$_2$)$_2$N), 3.26 (t, 2H, J=7.1 Hz, N(CH$_2$)$_2$N), 3.37-3.45 (m, 2H, ArCH$_2$CH$_2$N), 3.77 (td, 1H, J=11.3, 2.5 Hz, 1 of OCH$_2$CH$_2$), 3.93-4.02 (m, 3H, OCH+1 of OCH$_2$CH$_2$+1 of OCH$_2$CH), 4.04-4.10 (m, 1H, 1 of OCH$_2$CH), 6.48 (d, 1H, J=7.7 Hz, ArH), 6.65 (td, 1H, J=7.5, 0.9 Hz, ArH), 7.01-7.12 (m, 2H, ArH), 7.20-7.23 (m, 2H, ArH), 8.21-8.24 (m, 1H, ArH), 8.32-8.35 (m, 1H, ArH).

$^{13}$C-NMR (125 MHz, CDCl$_3$) δ: 28.7, 47.0, 53.4, 53.7, 55.7, 56.3, 66.9, 69.4, 73.9, 106.7, 117.6, 121.3, 123.8, 124.5, 127.3, 129.9, 138.0, 142.5, 152.3, 154.9.

LCMS: m/z 340.2017 ([M+H]$^+$, 100%); Rt 4.9 min, purity >99% DAD (180-450 nm).

Example 20

(S)-1-(Indolin-1-yl)-2-(2-((pyridin-3-yloxy)methyl)morpholino)ethanone (Compound 20s)

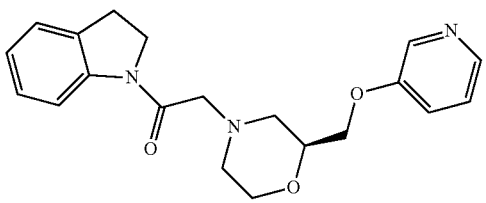 [SMILES: O=C(CN1CCO[C@H](COc2cccnc2)C1)N1CCc2ccccc21]

Compound 20s was synthesised using essentially the same procedure as compound 18s (Example 16), from compound 48 (Example 9; 55 mg, 0.2 mmol), 3-hydroxypyridine (28 mg, 0.3 mmol), triphenylphosphine (78 mg, 0.3 mmol), DEAD (0.05 ml, 0.3 mmol), and THF (1 ml). The crude residue was purified twice by flash chromatography (silica, DCM/MeOH 1:0 to 8:2) to afford the title compound as a colourless oil (53 mg; 74%). Analyses were performed on the free base, which was converted to the HCl salt for testing.

$^1$H-NMR (500 MHz, CD3OD) δ: 3.31 (m, 2H, 1 of ArCH$_2$), 3.47-3.41 (m, 2H, NCH$_2$), 3.71 (bs, 1H, 1 of CH$_2$N), 3.90 (bs, 1H, 1 of CH$_2$N), 4.07-4.25 (m, 4H, ArCH$_2$CH$_2$+CH$_2$N), 4.40-4.50 (m, 5H, CH$_2$OCHCH$_2$), 7.12 (t, 1H, J=7.5 Hz, ArH), 7.22 (t, 1H, J=8.3 Hz, ArH), 7.31 (d, 1H, 7.6 Hz, ArH), 7.99-8.01 (m, 1H, ArH), 8.17 (d, 1H, J=8.3 Hz, ArH), 8.25 (d, 1H, J=7.90 Hz, ArH), 8.49 (d, 1H, J=5.5 Hz, ArH), 8.67 (s, 1H, ArH).

Example 21

(S)-4-(2-(Indolin-1-yl)ethyl)-2-((pyridin-3-yloxy)methyl)morpholine (Compound 21s)

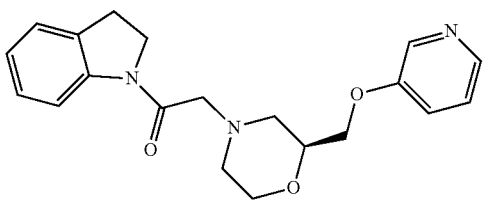 [SMILES: O=C(CN1CCO[C@H](COc2cccnc2)C1)N1CCc2ccccc21]

Essentially the same procedure was used as for compound 18s (Example 16), using compound 52 (Example 10; 52 mg, 0.2 mmol), 3-hydroxypyridine (28 mg, 0.3 mmol), triphenylphosphine (78 mg, 0.3 mmol), DEAD (0.05 ml, 0.3 mmol), and THF (1 ml). The crude residue was purified twice by flash chromatography (silica, DCM/MeOH 1:0 to 8:2) to afford the title compounds as a colourless oil (28 mg; 41%). Analyses were performed on the free base, which was converted to the HCl salt for testing.

$^1$H-NMR (500 MHz, CDCl$_3$) δ: 2.18-2.22 (m, 1H, 1 of (CH$_2$)$_2$N), 2.34 (dt, 1H, J=11.3, 3.3 Hz, 1 of (CH$_2$)$_2$N), 2.68 (t, 2H, J=6.9 Hz, N(CH$_2$)$_2$N), 2.83 (dd, 1H, J=11.4, 1.9 Hz, 1 of (CH$_2$)$_2$N), 2.99-3.00 (m, 3H, ArCH$_2$+1 of (CH$_2$)$_2$N), 3.28 (t, 2H, J=7.2 Hz, N(CH$_2$)$_2$N), 3.43 (dt, 2H, J=8.3, 1.3 Hz, ArCH$_2$CH$_2$N), 3.78 (dt, 1H, J=11.3, 2.5 Hz, 1 of OCH$_2$CH$_2$), 3.96-4.02 (m, 3H, OCH+1 of OCH$_2$CH$_2$+1 of OCHCH$_2$), 4.08-4.11 (m, 1H, 1 of OCH$_2$CH), 6.51 (d, 1H, J=7.7 Hz, ArH), 6.67 (dt, 1H, J=7.4, 0.9 Hz, ArH), 7.07-x7.10 (m, 2H, ArH), 7.23-7.24 (m, 2H, ArH), 8.25-8.26 (m, 1H, ArH), 8.37 (bs, 1H, ArH).

$^{13}$C-NMR (125 MHz, CDCl$_3$) δ: 28.7, 46.9, 53.4, 53.7, 55.7, 56.3, 66.9, 69.5, 73.9, 76.81, 106.7, 117.6, 121.3, 123.8, 124.5, 127.3, 129.8, 138.1, 142.5, 152.3, 154.9.

HRMS: Found 340.2019 C$_{20}$H$_{26}$N$_3$O$_2$ [M+H]$^+$ requires 340.2020.

Example 22

(R)-2-(2-((3-chlorophenoxy)methyl)morpholino)-1-(indolin-1-yl)ethanone (Compound 22r)

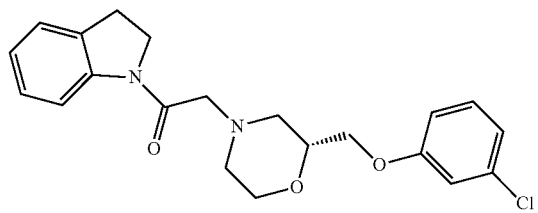 [SMILES: O=C(CN1CCO[C@@H](COc2cccc(Cl)c2)C1)N1CCc2ccccc21]

Essentially the same procedure was used as for compound 18s (Example 16), using compound 49 (Example 8; 90 mg, 0.326 mmol), 3-chlorophenol (63 mg, 0.49 mmol), triphenylphosphine (128 mg, 0.49 mmol), DIAD (0.10 ml, 0.49 mmol), and THF (1 ml). The crude residue was purified twice by flash chromatography (silica, DCM/MeOH 1:0 to 8:2) to afford the title compounds as colourless oil, 42 mg (33%). Analyses were performed on the free base, which was converted to the HCl salt for testing.

$^1$H-NMR (500 MHz, CDCl$_3$) δ: 2.22 (t, 1H, J=11.2 Hz, 1 of 1 of (CH$_2$)$_2$N), 2.37 (dt, 1H, J=11.2, 3.7 Hz, 1 of (CH$_2$)$_2$N), 2.78 (d, 1H, J=14 Hz, 1 of (CH$_2$)$_2$N), 2.95 (d, 1H, J=14 Hz, 1 of (CH$_2$)$_2$N), 3.13 (t, 2H, J=9.7 Hz, 1 of ArCH$_2$), 3.23 (s, 2H, COCH$_2$N), 3.73 (dt, 1H, J=11.6, 2.0 Hz, 1 of CHCH$_2$OAr), 3.83-3.95 (m, 4H, CH$_2$OCHCH$_2$+1 of CH$_2$OAr), 4.10 (t, 2H, J=8.7 Hz, ArCH$_2$CH$_2$), 6.71-6.73 (m, 1H, ArH), 6.84-6.87 (m, 2H, ArH), 6.95 (t, J=7.3 Hz, ArH), 7.09-7.15 (m, 3H, ArH), 8.16 (d, 1H, J=9.8 Hz, ArH).

LCMS: m/z 387.14 ([M+H]$^+$, 100%); Rt 5.5 min, purity >99% DAD (180-450 nm).

Example 23

(R)-2-((3-Chlorophenoxy)methyl)-4-(2-(indolin-1-yl)ethyl)morpholine (Compound 23r)

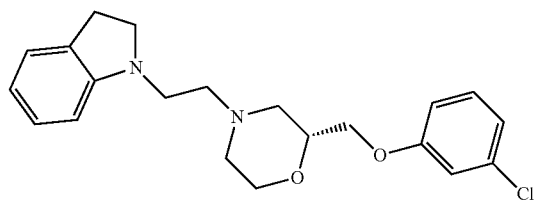 [SMILES: Clc1cccc(OC[C@H]2CN(CCN3CCc4ccccc43)CCO2)c1]

Essentially the same procedure was used to make compound 23r as was used to make compound 18s (Example 16), but with compound 52 (80 mg, 0.30 mmol), 3-chlorophenol (59 mg, 0.46 mmol), triphenylphosphine (120 mg, 0.46 mmol), DIAD (90 μl, 0.46 mmol) and THF (1.5 ml). The crude mixture was purified twice by column chromatography (silica, DCM/MeOH 1:0 to 96:4 then Hex/EtOAc 1:0 to 0:1) to afford compound 23r (5 mg, 4%). Analyses were performed on the free base, and the free base was converted to the HCl salt for testing.

$^1$H-NMR (500 MHz, CDCl$_3$) δ: 2.12-2.20 (m, 1H, 1 of (CH$_2$)$_2$N), 2.31 (td, 1H, J=11.3, 3.3 Hz, 1 of (CH$_2$)$_2$N), 2.65 (t, 2H, J=7.1 Hz, N(CH$_2$)$_2$N), 2.79-2.85 (m, 1H, 1 of (CH$_2$)$_2$N), 2.94-3.01 (m, 3H, ArCH$_2$CH$_2$N+1 of (CH$_2$)$_2$N), 3.26 (t, 2H, J=7.1 Hz, N(CH$_2$)$_2$N), 3.37-3.46 (m, 2H, ArCH$_2$CH$_2$N), 3.76 (td, 1H, J=11.3, 2.4 Hz, 1 of OCH$_2$CH$_2$), 3.88-4.05 (m, 4H, OCH+OCH$_2$CH+1 of OCH$_2$CH$_2$), 6.49 (d, 1H, J=7.7 Hz, ArH), 6.63-6.68 (m, 1H, ArH), 6.79-6.83 (m, 1H, ArH), 6.90-6.96 (m, 2H, ArH), 7.04-7.10 (m, 2H, ArH), 7.19 (t, 1H, J=8.1 Hz, ArH).

$^{13}$C-NMR (125 MHz, CDCl$_3$) δ: 28.7, 46.9, 53.4, 53.7, 55.8, 56.3, 66.9, 69.4, 73.9, 106.8, 113.1, 115.0, 117.6, 121.2, 124.5, 127.3, 129.9, 130.2, 134.8, 152.3, 159.4.

LCMS: m/z 373.17 ([M+H]$^+$, 100%); Rt 5.8 min, purity >95% DAD (180-450 nm).

HRMS: Found 373.1665 C$_{21}$C$_{25}$ClN$_2$O$_2$ requires 373.1677.

Example 24

(S)-2-(2-((3-Chlorophenoxy)methyl)morpholino)-1-(indolin-1-yl)ethanone (Compound 22s)

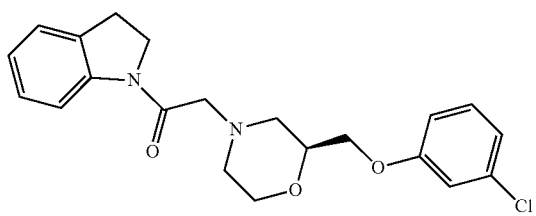 [SMILES: O=C(CN1CCO[C@H](COc2cccc(Cl)c2)C1)N1CCc2ccccc21]

Compound 22s was synthesised by essentially the same procedure as compound 18s (Example 16), using compound 48 (Example 7; 55 mg, 0.2 mmol), 3-chlorophenol (39 mg, 0.3 mmol), triphenylphosphine (78 mg, 0.3 mmol), DEAD (0.05 ml, 0.3 mmol), and THF (1 ml). The crude residue was purified twice by flash column chromatography (silica, DCM/MeOH 1:0 to 8:2) to afford the title compound as a colourless oil (51 mg; 65%). Analyses were performed on the free base, and the free base was converted to the HCl salt for testing.

$^1$H-NMR (500 MHz, CD$_3$OD) δ: 3.30 (t, 2H, J=8.3 Hz, ArCH$_2$), 3.36-3.38 (m, 2H, CH$_2$N), 3.69 (bs, 1H, 1 of CH$_2$N), 3.82 (bs, 1H, 1 of CH$_2$N), 4.04-4.23 (m, 6H, ArCH$_2$CH$_2$+CH$_2$N, +CH$_2$O), 4.30 (bs, 1H, 1 of CH$_2$O), 4.44 (s, 2H, 1 of CH$_2$O+OCH), 6.93 (d, 1H, J=8.1 Hz, ArH), 6.99-7.02 (m, 2H, ArH), 7.12 (t, 1H, J=7.4 Hz, ArH), 7.22 (t, 1H, J=7. Hz, ArH), 7.27-7.30 (m, 2H, ArH), 8.17 (d, 1H, J=8.2 Hz, ArH).

Example 25

(S)-2-((3-chlorophenoxy)methyl)-4-(2-(indolin-1-yl)ethyl)morpholine (Compound 23s)

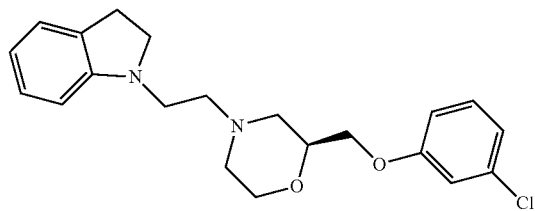 [SMILES: Clc1cccc(OC[C@@H]2CN(CCN3CCc4ccccc43)CCO2)c1]

Compound 23s was synthesised with essentially the same procedure as compound 18s (Example 16), from compound 51 (Example 10; 52 mg, 0.2 mmol), 3-chlorophenol (39 mg, 0.3 mmol), triphenylphosphine (78 mg, 0.3 mmol), DEAD (0.05 ml, 0.3 mmol), and THF (1 ml). The crude residue was purified twice by flash column chromatography (silica, DCM/MeOH 1:0 to 8:2) to afford the title compound as a colourless oil (30 mg; 40%). Analyses were performed on the free base, and the free base was converted to the HCl salt for testing.

$^1$H NMR (500 MHz, CDCl$_3$) ä 2.19 (dd, 1H, J=10.8, 10.1 Hz, 1 of (CH$_2$)$_2$N), 2.34 (td, 1H, J=11.3, 3.3 Hz, 1 of (CH$_2$)$_2$N), 2.65 (t, 2H, J=6.9 Hz, N(CH$_2$)$_2$N), 2.83 (dt, 1H, J=11.0, 5.5 Hz, 1 of (CH$_2$)$_2$N), 2.98-3.07 (m, 3H, ArCH$_2$+1 of (CH$_2$)$_2$N), 3.28 (t, 2H, J=7.4 Hz, N(CH$_2$)$_2$N), 3.45 (dt, 2H, J=8.3, 1.5 Hz, ArCH$_2$CH$_2$), 3.79 (td, 1H, J=11.3, 2.5 Hz, 1 of OCH$_2$CH$_2$), 4.08-3.91 (m, 4H, OCHCH$_2$+1 of CH$_2$O), 6.52 (d, 1H, J=7.7 Hz, ArH), 6.68 (dt, 1H, J=7.4, 9 Hz, ArH), 6.84 (ddd, 1H, J=8.4, 2.4, 0.9 Hz, ArH), 6.93-7.00 (m, 2H, ArH), 7.10 (t, 2H, J=7.6 Hz, ArH), 7.22 (dt, 1H, J=8.2, 0.3 Hz, ArH).

$^{13}$C NMR (125 MHz, CDCl$_3$) δ 26.7, 46.9, 53.4, 53.7, 55.6, 56.3, 66.9, 69.4, 73.9, 106.7, 113.3, 115.1, 117.6, 121.2, 124.5, 127.3, 129.8, 130.2, 134.9, 152.3, 159.4.

HRMS: Found 373.1673 C$_{21}$H$_{26}$ClN$_2$O$_2$ [M+H]$^+$ requires 373.1677.

Example 26

(S)-1-(Indolin-1-yl)-2-(2-((3-methoxyphenoxy)methyl)morpholino)ethanone (Compound 24s)

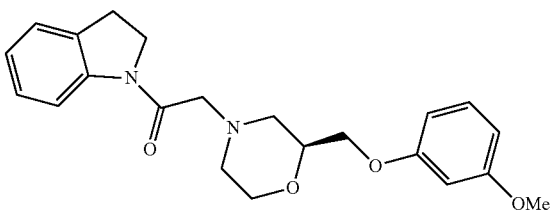 [SMILES: COc1cccc(OC[C@@H]2CN(CC(=O)N3CCc4ccccc43)CCO2)c1]

Essentially the same procedure was used to make compound 24s as was used for compound 18s (Example 16), with compound 48 (Example 7; 55 mg, 0.2 mmol), 3-methoxyphenol (0.032 ml, 0.3 mmol), triphenylphosphine (78 mg, 0.3 mmol), DEAD (0.05 ml, 0.3 mmol), and THF (1 ml). The crude residue was purified twice by flash column chromatography (silica, DCM/MeOH 1:0 to 8:2) to afford the title compound as a colourless oil (60 mg; 78%). Analyses were performed on the free base, and the free base was converted to the HCl salt for testing.

$^1$H-NMR (500 MHz, CD$_3$OD) δ: 3.31 (t, 2H, J=8.1 Hz, ArCH$_2$), 3.36-3.38 (bs, 2H, CH$_2$N), 3.73 (bs, 1H, 1 of (CH$_2$)$_2$N), 3.78 (s, 3H, OCH$_3$), 3.86 (bs, 1H, 1 of (CH$_2$)$_2$N), 4.04-4.25 (m, 6H, ArCH$_2$CH$_2$+CH$_2$N+CH$_2$O), 4.29 (bs, 1H, 1 of OCH$_2$), 4.45 (s, 2H, OCH+1 of OCH$_2$), 6.54-6.58 (m, 3H, ArH), 7.12 (t, 1H, J=7.6 Hz, ArH), 7.18-7.24 (m, 2H, ArH), 7.30 (d, 1H, J=7.9 Hz, ArH), 8.17 (d, 1H, J=8.0 Hz, ArH).

Example 27

(S)-4-(2-(Indolin-1-yl)ethyl)-2-((3-methoxyphenoxy)methyl)morpholine (Compound 25s)

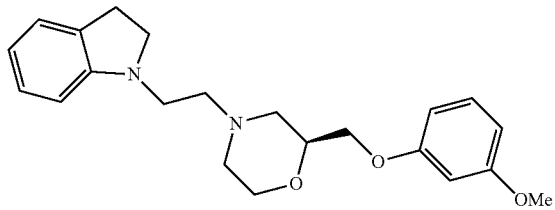 [SMILES: COc1cccc(OC[C@@H]2CN(CCN3CCc4ccccc43)CCO2)c1]

Essentially the same procedure was used to make compound 25s as was used for compound 18s (Example 16), with compound 51 (Example 10; 52 mg, 0.2 mmol), 3-methoxyphenol (0.032 ml, 0.3 mmol), triphenylphosphine (78 mg, 0.3 mmol), DEAD (0.05 ml, 0.3 mmol), and THF (1 ml). The crude residue was purified twice by flash column chromatography (silica, DCM/MeOH 1:0 to 8:2) to afford the title compound as a colourless oil (46 mg; 62%). Analyses were performed on the free base, and the free base was converted to the HCl salt for testing.

$^1$H NMR (500 MHz, CDCl$_3$) ä 2.24-2.13 (m, 1H, 1 of (CH$_2$)$_2$N), 2.34 (td, 1H, J=11.3, 3.3 Hz, 1 of (CH$_2$)$_2$N), 2.67 (t, 2H, J=7.1 Hz, N(CH$_2$)$_2$N), 2.84 (dd, 1H, J=11.4, 1.6 Hz, 1 of (CH$_2$)$_2$N), 2.98-3.02 (m, 3H, ArCH$_2$+1 of (CH$_2$)$_2$N), 3.28 (t, 2H, J=7.2 Hz, N(CH$_2$)$_2$N), 3.44 (dt, 2H, J=8.2 2.0, ArCH$_2$CH$_2$), 3.78 (dt, 1H, J=11.3, 2.5 Hz, 1 of OCH$_2$CH$_2$), 3.81 (s, 3H, OCH$_3$), 4.08-3.93 (m, 4H, OCHCH$_2$+1 of CH$_2$O), 6.57-6.49 (m, 4H, ArH), 6.68 (t, 1H, J=7.1 Hz, ArH), 7.07-7.11 (m, 2H, ArH), 7.20 (dt, 1H J=8.1 0.5 Hz, ArH).

$^{13}$C NMR (125 MHz, CDCl$_3$) ä 28.67, 46.9, 53.4, 53.7, 55.3, 56.0, 56.3, 66.9, 69.2, 74.0, 101.1, 106.6, 106.7, 106.8, 117.6, 124.5, 127.3, 129.9, 152.3, 159.9, 160.8.

HRMS: Found 369.2162 C$_{22}$H$_{29}$N$_2$O$_3$ [M+H]$^+$ requires 369.2173.

Example 28

(R)-4-(2-(Indolin-1-yl)ethyl)-2-((3-methoxyphenoxy)methyl)morpholine (Compound 25r)

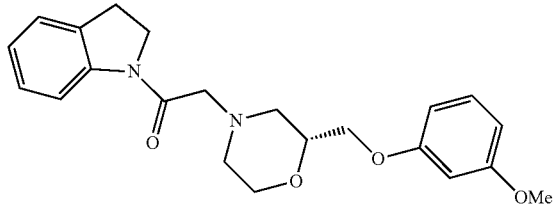 [SMILES: COc1cccc(OC[C@H]2CN(CC(=O)N3CCc4ccccc43)CCO2)c1]

Compound 25r was synthesised by essentially the same procedure as compound 18s (Example 16), starting from compound 52 (80 mg, 0.30 mmol), which was reacted with 3-methoxyphenol (50 µl, 0.46 mmol), PPh$_3$ (120 mg, 0.46 mmol), DIAD (90 µl, 0.46 mmol), and THF (1.5 ml). The crude mixture was purified twice by flash column chromatography (silica, DCM/MeOH 1:0 to 94:6 then Hex/EtOAc 1:0 to 0:1) to afford the title compound (18 mg, 16%). Analyses were performed on the free base, which was converted to the HCl salt for testing.

For $^1$H and $^{13}$C NMR data see compound 25s.

LCMS: m/z 369.22 ([M+H]$^+$, 100%); Rt 5.5 min, purity >98% DAD (180-450 nm).

Example 29

(R)-4-(2-(Indolin-1-yl)ethyl)-2-(((2-methylpyridin-3-yl)oxy)methyl)morpholine (Compound 26r)

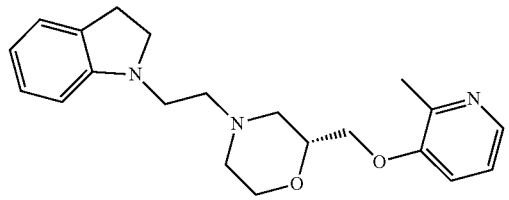 [SMILES: Cc1ncccc1OC[C@H]1CN(CCN2CCc3ccccc32)CCO1]

Essentially the same procedure was followed as for compound 18s (Example 16) by reacting compound 52 (Example 11; 80 mg, 0.30 mmol) with 2-methyl-3-hydroxypyridine (50 mg, 0.46 mmol), PPh$_3$ (120 mg, 0.46 mmol), DIAD (90 µl, 0.46 mmol), and THF (1.5 ml). The crude mixture was purified by flash column chromatography (silica, DCM/MeOH 1:0 to 94:6) to afford compound 26r (49 mg, 46%). Analyses performed on the free base. Converted into the HCl salt for testing.

$^1$H-NMR (500 MHz, CDCl$_3$) δ: 2.15-2.22 (m, 1H, 1 of (CH$_2$)$_2$N), 2.30 (td, 1H, J=11.3, 3.3 Hz, 1 of (CH$_2$)$_2$N), 2.47 (s, 3H, Me), 2.66 (t, 2H, J=7.0 Hz, N(CH$_2$)$_2$N), 2.80-2.85 (m, 1H, 1 of (CH$_2$)$_2$N), 2.97 (t, 2H, J=8.3 Hz, ArCH$_2$CH$_2$N), 3.01-3.06 (m, 1H, 1 of (CH$_2$)$_2$N), 3.21-3.31 (m, 2H, N(CH$_2$)$_2$N), 3.36-3.46 (m, 2H, ArCH$_2$CH$_2$N), 3.77 (td, 1H, J=11.3, 2.5 Hz, 1 of OCH$_2$CH$_2$), 3.88-4.01 (m, 3H, OCH+1 of OCH$_2$CH$_2$+1 of OCH$_2$CH), 4.01-4.06 (m, 1H, 1 of OCH$_2$CH), 6.49 (d, 1H, J=7.7 Hz, ArH), 6.65 (td, 1H, J=7.5, 0.9 Hz, ArH), 7.03-7.10 (m, 4H, ArH), 8.07-8.10 (m, 1H, ArH).

$^{13}$C-NMR (125 MHz, CDCl$_3$) δ: 19.4, 28.7, 47.0, 53.4, 53.7, 55.7, 56.2, 66.9, 69.3, 73.9, 106.7, 117.6, 117.7, 121.7, 124.5, 127.3, 129.9, 140.8, 149.1, 152.3, 153.0.

LCMS: m/z 354.22 ([M+H]$^+$, 100%); Rt 5.1 min, purity >97% DAD (180-450 nm).

HRMS: Found 354.2185 C$_{21}$H$_{27}$N$_3$O$_2$ [M+H]$^+$ requires 354.2176.

Example 30

(S)-4-(2-(Indolin-1-yl)ethyl)-2-(((2-methylpyridin-3-yl)oxy)methyl)morpholine (Compound 26s)

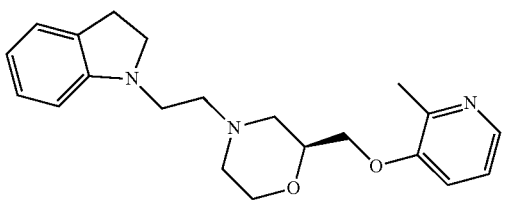 [SMILES: Cc1ncccc1OC[C@@H]1CN(CCN2CCc3ccccc32)CCO1]

The title compound was synthesised in essentially the same way as compound 18s. Compound 51 (Example 10; 80 mg, 0.30 mmol) and PPh₃ (120 mg, 0.46 mmol) were dissolved in dry THF (1.5 ml). Then DIAD (90 µl, 0.46 mmol) and 2-methyl-3-hydroxypyridine (50 mg, 0.46 mmol) were added. The reaction mixture was stirred at RT for 48 hrs. After this time, the solvent was removed and the crude mixture purified by flash column chromatography (silica, DCM/MeOH 1:0 to 94:6) to afford compound 26s (75 mg, 71%). Analyses were performed on the free base. The compound was converted to the HCl salt for testing.

For $^1$H and $^{13}$C NMR data see compound 26r.

Example 31

(R)-2-(((5-Chloropyridin-3-yl)oxy)methyl)-4-(2-(indolin-1-yl)ethyl)morpholine (Compound 27r)

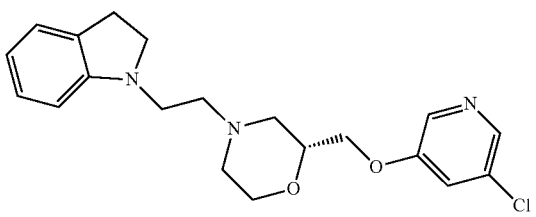 [SMILES: Clc1cncc(OC[C@H]2CN(CCN3CCc4ccccc43)CCO2)c1]

Essentially the same procedure was employed as for compound 18s (Example 16): starting from compound 52 (Example 11; 80 mg, 0.30 mmol), 5-chloro-3-hydroxypyridine (59 mg, 0.46 mmol), PPh₃ (120 mg, 0.46 mmol), DIAD (90 µl, 0.46 mmol) and THF (1.5 ml). The crude mixture was purified by flash column chromatography (silica, DCM/MeOH 1:0 to 94:6) to afford compound 27r (100 mg). Analyses performed on the free base. Converted into the HCl salt for testing. A sample of compound 27r was re-purified to assay (purity >97%).

For $^1$H and $^{13}$C NMR data see compound 27s.

LCMS: m/z 374.16 ([M+H]⁺, 100%); Rt 5.3 min, purity=90% DAD (180-450 nm).

Example 32

(S)-2-(((5-Chloropyridin-3-yl)oxy)methyl)-4-(2-(indolin-1-yl)ethyl)morpholine (Compound 27s)

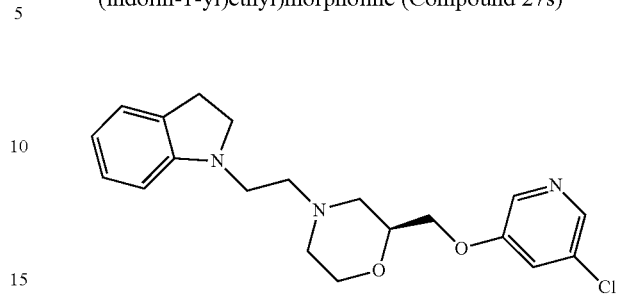

Compound 27s was synthesised by essentially the same procedure as compound 18s (Example 16). Compound 51 (Example 10; 80 mg, 0.30 mmol), was reacted with 5-chloro-3-hydroxypyridine (59 mg, 0.46 mmol), PPh₃ (120 mg, 0.46 mmol), DIAD (90 µl, 0.46 mmol) and THF (1.5 ml). The reaction mixture was stirred at RT for 48 hrs. After this time, the solvent was removed and the crude mixture purified twice by flash column chromatography (silica, DCM/MeOH 1:0 to 94:6, then Hex/EtOAc 1:0 to 0:1) to afford compound 27s (71 mg, 91%). Analyses were performed on the free base. The compound was re-purified (36.7 mg, purity 100%), and converted to the HCl salt for assaying.

$^1$H-NMR (500 MHz, CDCl₃) δ: 2.13-2.20 (m, 1H, 1 of (CH₂)₂N), 2.31 (td, 1H, J=11.3, 3.3 Hz, 1 of (CH₂)₂N), 2.65 (t, 2H, J=7.1 Hz, N(CH₂)₂N), 2.79-2.85 (m, 1H, 1 of (CH₂)₂N), 2.92-3.00 (m, 3H, ArCH₂CH₂N+1 of (CH₂)₂N), 3.25 (t, 2H, J=7.1 Hz, N(CH₂)₂N), 3.36-3.45 (m, 2H, ArCH₂CH₂N), 3.76 (td, 1H, J=11.3, 2.4 Hz, 1 of OCH₂CH₂), 3.92-4.01 (m, 3H, OCH+1 of OCH₂CH₂+1 of OCH₂CH), 4.02-4.09 (m, 1H, 1 of OCH₂CH), 6.49 (d, 1H, J=7.7 Hz, ArH), 6.63-6.68 (m, 1H, ArH), 7.04-7.10 (m, 2H, ArH), 7.22-7.25 (m, 1H, ArH), 8.20 (d, 1H, J=2.0 Hz, ArH), 8.22 (d, 1H, J=2.6 Hz, ArH).

$^{13}$C-NMR (125 MHz, CDCl₃) δ: 28.6, 47.0, 53.4, 53.7, 55.7, 56.3, 66.9, 69.5, 73.9, 106.7, 117.6, 121.3, 123.8, 124.5, 127.3, 129.9, 138.0, 139.7, 142.5, 152.3, 154.9.

LCMS: m/z 374.16 ([M+H]⁺, 100%); Rt 5.3 min, purity=91% DAD (180-450 nm).

HRMS: Found 374.1619 C₂₀H₂₄N₃O₂Cl [M+H]₊ requires 374.1630.

Example 33

(R)-4-(2-(Indolin-1-yl)ethyl)-2-(((6-methylpyridin-3-yl)oxy)methyl)morpholine (Compound 28r)

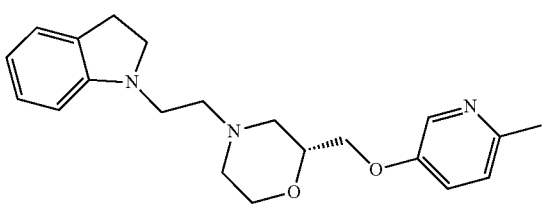 [SMILES: Cc1ccc(OC[C@H]2CN(CCN3CCc4ccccc43)CCO2)cn1]

Essentially the same procedure was used to make compound 28r as for compound 18s (Example 16). Compound 52

(Example 11; 80 mg, 0.30 mmol) was reacted with 6-methyl-3-hydroxypyridine (50 mg, 0.46 mmol), PPh₃ (120 mg, 0.46 mmol), DIAD (90 µl, 0.46 mmol) and THF (1.5 ml). The crude mixture was purified by flash column chromatography (silica, DCM/MeOH 1:0 to 94:6) to afford compound 28r (57 mg, 54%). Analyses performed on the free base. Converted into the HCl salt for testing.

$^1$H-NMR (500 MHz, CDCl₃) δ: 2.13-2.21 (m, 1H, 1 of (CH₂)₂N), 2.31 (td, 1H, J=11.4, 3.3 Hz, 1 of (CH₂)₂N), 2.48 (s, 3H, Me), 2.65 (t, 2H, J=7.1 Hz, N(CH₂)₂N), 2.79-2.85 (m, 1H, 1 of (CH₂)₂N), 2.92-2.99 (m, 3H, ArCH₂CH₂N+1 of (CH₂)₂N), 3.22-3.27 (m, 2H, N(CH₂)₂N), 3.35-3.44 (m, 2H, ArCH₂CH₂N), 3.76 (td, 1H, J=11.4, 2.4 Hz, 1 of OCH₂CH₂), 3.88-3.99 (m, 3H, OCH+1 of OCH₂CH₂+1 of OCH₂CH), 3.99-4.06 (m, 1H, 1 of OCH₂CH), 6.48 (d, 1H, J=7.7 Hz, ArH), 6.64 (td, 1H, J=7.5, 0.8 Hz, ArH), 7.02-7.09 (m, 3H, ArH), 7.13 (dd, 1H, J=8.5, 3.0 Hz, ArH), 8.20 (d, 1H, J=2.9 Hz, ArH).

$^{13}$C-NMR (125 MHz, CDCl₃) δ: 23.4, 28.6, 46.9, 53.3, 53.7, 55.7, 56.2, 66.8, 69.7, 73.9, 106.8, 117.7, 122.6, 123.6, 124.3, 127.3, 129.9, 136.3, 150.6, 152.3, 153.0.

LCMS: m/z 354.22 ([M+H]⁺, 100%); Rt 5.1 min, purity >96% DAD (180-450 nm).

HRMS: Found 354.2190 C₂₁H₂₈N₃O₂ [M+H]⁺ requires 354.2176.

Example 34

(S)-4-(2-(Indolin-1-yl)ethyl)-2-(((6-methylpyridin-3-yl)oxy)methyl)morpholine (Compound 28s)

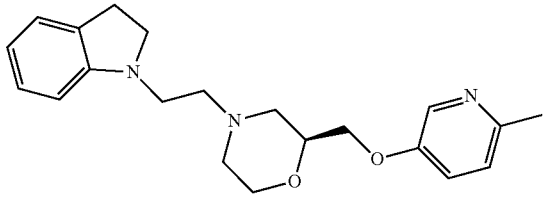 [SMILES: Cc1ccc(OC[C@@H]2CN(CCN3CCc4ccccc43)CCO2)cn1]

The same basic procedure used to synthesised compound 18s (Example 16) was used, from compound 51 (Example 10; 80 mg, 0.30 mmol) with 6-methyl-3-hydroxypyridine (50 mg, 0.46 mmol) in place of 2-methyl-3-hydroxypyridine, PPh₃ (120 mg, 0.46 mmol), DIAD (90 µl, 0.46 mmol) and tetrahydrofuran (1.5 ml). The crude mixture was purified by flash column chromatography (silica, DCM/MeOH 1:0 to 94:6) to afford compound 28s (58 mg, 55%). Analyses performed on the free base. Converted into the HCl salt for testing.

For $^1$H and $^{13}$C NMR data see compound 28r.

LCMS: m/z 354.22 ([M+H]⁺, 100%); Rt 5.1 min, purity >94% DAD (180-450 nm).

Example 35

(R)-2-(((2,4-Dimethylpyridin-3-yl)oxy)methyl)-4-(2-(indolin-1-yl)ethyl)morpholine (Compound 29r)

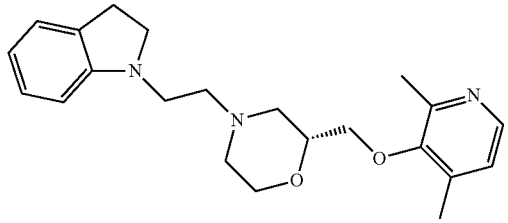 [SMILES: Cc1ccnc(C)c1OC[C@H]1CN(CCN2CCc3ccccc32)CCO1]

Essentially the same procedure was used to make compound 29r as was used for compound 21r (Example 19), except that compound 52 (Example 11) was reacted with 2,4-dimethyl-3-hydroxypyridine (57 mg, 0.46 mmol) instead of 3-hydroxypyridine, in the presence of PPh₃ (120 mg, 0.46 mmol), DIAD (90 µl, 0.46 mmol) and THF (1.5 ml). The crude mixture was purified by flash column chromatography (silica, DCM/MeOH 1:0 to 94:6) to afford compound 29r (48 mg, 44%). Analyses were performed on the free base and it was converted into the HCl salt for testing.

$^1$H-NMR (500 MHz, CDCl₃) δ: 2.17-2.24 (m, 1H, 1 of (CH₂)₂N), 2.29-2.38 (m, 4H, 1 of (CH₂)₂N+Me), 2.53 (s, 3H, Me), 2.68 (t, 2H, J=7.1 Hz, N(CH₂)₂N), 2.83-2.88 (m, 1H, 1 of (CH₂)₂N), 2.96-3.05 (m, 3H, ArCH₂CH₂N+1 of (CH₂)₂N), 3.26-3.32 (m, 2H, N(CH₂)₂N), 3.39-3.48 (m, 2H, ArCH₂CH₂N), 3.76-3.89 (m, 3H, OCH+OCH₂CH₂), 3.96-4.03 (m, 2H, OCH₂CH), 6.51 (d, 1H, J=7.7 Hz, ArH), 6.65-6.70 (m, 1H, ArH), 6.97 (d, 1H, J=4.9 Hz, ArH), 7.05-7.12 (m, 2H, ArH), 8.14 (d, 1H, J=4.9 Hz, ArH).

$^{13}$C-NMR (125 MHz, CDCl₃) δ: 15.7, 19.4, 28.6, 46.9, 53.3, 53.7, 55.7, 56.3, 66.8, 73.5, 74.6, 106.7, 117.6, 124.2, 124.5, 127.3, 129.9, 139.7, 144.4, 152.2, 152.3.

LCMS: m/z 368.23 ([M+H]⁺, 100%); Rt 5.1 min, purity >99% DAD (180-450 nm).

HRMS: Found 368.2333 C₂₂H₃₀N₃O₂ [M+H]⁺ requires 368.2333.

Example 36

Compound 304

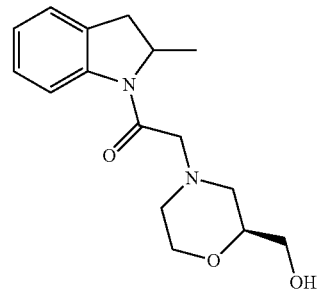 [SMILES: CC1Cc2ccccc2N1C(=O)CN1CCO[C@H](CO)C1]

Essentially the same procedure was used to make compound 304 as was used for compound 48 (Example 7). A microwave vial was charged with 1-(chloroacetyl)-2-methylindoline (100 mg, 0.48 mmol), hydroxymethylmorpholine (compound 54; 71 mg, 0.60 mmol), triethylamine (0.13 ml, 0.96 mmol) and ACN (2 ml). The vial was sealed and irradiated for 30 min at 100° C.; the solvent was removed under reduced pressure; and the crude residue was purified by flash chromatography using a 0→40% gradient of (20% MeOH/DCM)/DCM. The product was obtained as a yellowish solid (131 mg; 95%).

$^1$H-NMR (500 MHz, CDCl₃) δ: 1.32 (bs, 3H, CH₃), 1.90 (bs, 1H, OH), 2.43 (t, 1H, J=10.4 Hz, 1 of (CH₂)₂N), 2.48 (dt, 1H, J₁=11.3, J₂=3.3 Hz, 1 of (CH₂)₂N), 2.67-2.69 (m, 1H, Ar—CHH), 2.86-2.95 (m, 2H, 2 of (CH₂)₂N), 3.25-3.49 (m, 3H, Ar—CHH+COCH₂N), 3.58-3.71 (m, 2H, CH₂OCHCH₂OH), 3.72-3.86 (m, 2H, OCHHOH), 3.86-3.93 (m, 1H, OCHCHHOH), 4.73 (bs, 1H, CHCH₃), 7.07 (t, 1H, J=8.2 Hz, ArH), 7.25-7.28 (m, 2H, ArH), 8.19 (bs, 1H, ArH).

Example 37

Compound 305

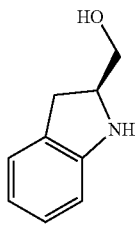 [SMILES: OC[C@@H]1Cc2ccccc2N1]

Borane THF complex (1M; 15 ml) was added to a cooled (0° C.) solution of (S)-indoline carboxylic acid (979 mg, 5.95 mmol) in dry THF (12 ml). The clear solution was stirred overnight at room temperature, quenched with water (gas evolution occurs). The mixture was extracted with diethyl ether (3×10 ml). The organic layer was washed with saturated NaHCO₃ (2×5 ml) and brine (10 ml). The solvent was removed under reduced pressure. The residue could be used for the next step without further purification (724 mg).

$^1$H-NMR (500 MHz, CDCl₃) δ: 1.24-1.45 (m, 1H, 1 of Ar—C$\underline{H}_2$), 2.62-2.76 (m, 1H, 1 of Ar—C$\underline{H}_2$), 3.01-3.06 (m, 1H, C$\underline{H}$CH₂OH), 3.56-3.75 (m, 3H, C$\underline{H}_2$O$\underline{H}$), 3.99 (bs, 1H, N$\underline{H}$), 6.53-6.71 (m, 2H, Ar$\underline{H}$), 6.93-7.04 (m, 2H, Ar$\underline{H}$).

LCMS: m/z 150.10 ([M+H]⁺, 100%); Rt 3.2 min, purity >95% DAD (180-450).

Example 38

Compound 306

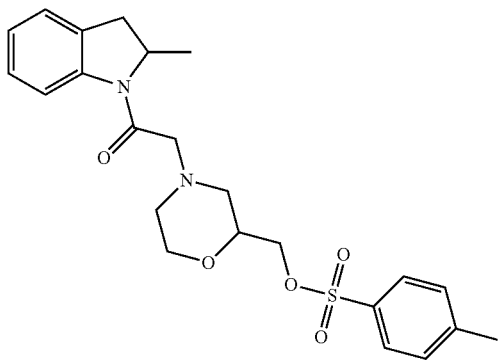 [SMILES: Cc1ccc(S(=O)(=O)OCC2CN(CC(=O)N3c4ccccc4CC3C)CCO2)cc1]

Compound 306 was prepared by tosylating compound 304 using a standard procedure for tosylation of alcohols. Compound 304 (Example 36; 24 mg, 0.083 mmol), tosyl chloride (19 mg, 0.1 mmol), dimethylaminopyridine (DMAP; 2 mg) and TEA (0.015 ml, 0.1 mmol) were reacted in DCM. The product could be used without further purification (18 mg; 46%).

$^1$H-NMR (500 MHz, CDCl₃) δ:

Example 39

Compound 307

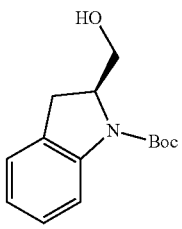 [SMILES: CC(C)(C)OC(=O)N1c2ccccc2C[C@H]1CO]

Boc anhydride (1.1 g) was added to a solution of compound 305 (700 mg, 4.69 mmol) in DCM (7 ml) at 0° C. The reaction was stirred overnight at room temperature, diluted with DCM and washed with saturated NaHCO₃ (1×10 ml). The organic phase was dried and concentrated under reduced pressure to produce an oil, which was purified by flash chromatography to obtain the product (760 mg; 65%).

$^1$H-NMR (500 MHz, CDCl₃) δ: 1.62 (s, 9H, C(C$\underline{H}_3$)₃), 2.83 (bs, 1H, 1 of Ar—C$\underline{H}_2$), 3.37 (dd, 1H, J₁=10.2, J₂=1.64 Hz, 1 of Ar—C$\underline{H}_2$), 3.71-3.81 (m, 2H, C$\underline{H}_2$OH), 4.63 (bs, 1H, C$\underline{H}$CH₂OH), 6.98 (t, 1H, J=7.4 Hz, Ar$\underline{H}$), 7.16-7.20 (m, 2H, Ar$\underline{H}$), 7.58 (bs, 1H, Ar$\underline{H}$).

LCMS: m/z 521.26 ([2M+Na]⁺, 100%); Rt 4.6 min, purity >95% DAD (180-450).

Example 40

Compound 308

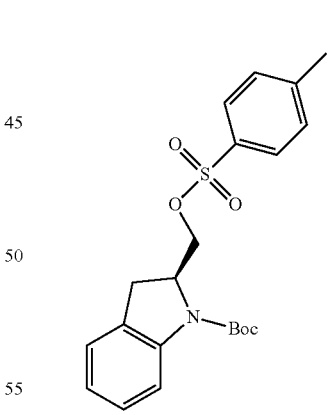

Compound 308 was prepared by tosylating compound 307 using a standard procedure for tosylation of alcohols. Compound 307 (Example 39; 760 mg, 3.05 mmol), tosyl chloride (1.16 mg, 6.10 mmol) and pyridine (7 ml) were reacted in DCM (3 ml). The product was obtained as a yellowish oil, which could be used without further purification (1.07 g).

$^1$H-NMR (500 MHz, CDCl₃) δ: 1.52 (s, 9H, C(C$\underline{H}_3$)₃), 2.46 (s, 3H, C$\underline{H}_3$), 2.97 (dd, 1H, J₁=2.4, J₂=16.4 Hz, 1 of Ar—C$\underline{H}_2$), 3.32 (dd, J₁=10.0, J₂=16.4 Hz, 1 of Ar—C$\underline{H}_2$), 4.60 (bs, 1H, 1 of C$\underline{H}_2$OH), 4.23 (dd, 1H, J₁=3.7, J₂=9.7 Hz, CH₂OH), 4.63 (bs, 1H, CHCH₂OH), 6.96 (dt, J₁=7.4, J₂=1.0 Hz, ArH), 7.12-7.18 (m, 2H, ArH), 7.33 (d, 2H, J=9.0 Hz, Ar H), 7.71 (d, 2H, J=10.3 Hz, ArH).

LCMS: m/z 421.18 ([M+Na]⁺, 100%); Rt 5.3 min, purity >95% DAD (180-450).

Example 41

Compound 309

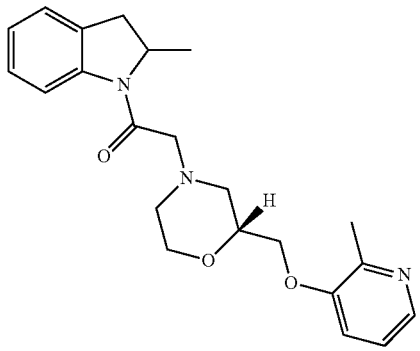 [SMILES: Cc1ncccc1OC[C@H]1CN(CC(=O)N2c3ccccc3CC2C)CCO1]

A microwave vial was charged with compound 306 (Example 38; 18 mg, 0.04 mmol), 2-methyl-3-hydroxypyridine (5 mg, 0.04 mmol), TEA (0.06 ml, 0.044 mmol) and ACN (1 ml). The vial was sealed and irradiated for 30 min at 100° C.; the solvent was removed under reduced pressure; and the crude residue was purified by flash chromatography using a 040% gradient of (20% MeOH/DCM)/DCM. The product was obtained as a colourless oil (4 mg; 26%).

¹H-NMR (500 MHz, CDCl₃) δ: 1.34 (bs, 3H, CH₃), 2.39 (t, 1H, J=11.0 Hz, 1 of (CH₂)₂N), 2.48-2.51 (m, 4H, Ar—CH₃+1 of (CH₂)₂N), 2.67-2.69 (m, 1H, Ar—CHH), 2.86-2.95 (m, 1H, 1 of (CH₂)₂N), 3.09-3.16 (m, 1H, 1 of (CH₂)₂N), 3.31-3.52 (m, 3H, Ar—CHH+COCH₂N), 3.82-90 (m, 1H, CH₂OCHCH₂OH), 3.95-4.01 (m, 2H, OCHCH₂OAr), 4.04-4.10 (m, 2H, CH₂OCHCH₂OAr), 4.73 (bs, 1H, CHCH₃), 7.07 (t, 1H, J=8.2 Hz, ArH), 7.25-7.28 (m, 2H, ArH), 8.10-8.12 (m, 1H, ArH), 8.20 (bs, 1H, ArH).

LCMS: m/z 382.2 ([M+H]⁺, 100%); Rt 4.4 min, purity >95% DAD (180-450).

Example 42

Compound 310

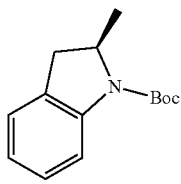 [SMILES: C[C@@H]1Cc2ccccc2N1C(=O)OC(C)(C)C]

Compound 310 was prepared following the procedure described in *J. Org. Chem.*, (1997), 62(22), pp 7679-7689. Compound 308 (Example 40; 1 g, 2.5 mmol), NaBH₄ (243 mg) and DMSO (13 ml) were used. The title compound was obtained as a colourless oil (499 mg; 83%).

¹H-NMR (500 MHz, CDCl₃) δ: 1.32 (d, 3H, J=6.3 Hz, CHCH₃), 1.60 (s, 9H, C(CH₃)₃), 2.63 (d, 1H, J=15.8 Hz, 1 of Ar—CH₂), 3.37 (dd, 1H, J₁=15.8, J2=9.6 Hz, 1 of Ar—CH₂), 4.57 (bs, 1H, CHCH₃), 6.96 (t, 1H, J=7.4 Hz, ArH), 7.15-7.20 (m, 2H, ArH), 7.37 (bs, 1H, ArH).

¹³C-NMR (125 MHz, CDCl₃) δ: 21.1 (CH₃), 28.5 (CH₃), 35.7 (Ar—CH₂), 55.3 (CHCH₃), 84.7 (C(CH₃)₃), 115.3 (Ar CH), 122.25 (ArCH), 124.9 (ArC), 127.4 (ArCH), 152.3 (Ar C), 167.9 (COOtBu).

LCMS: m/z 178.08 ([M-tBuOH+NH₄]⁺, 100%); Rt 5.2 min, purity >95% DAD (180-450).

Example 43

Compound 60

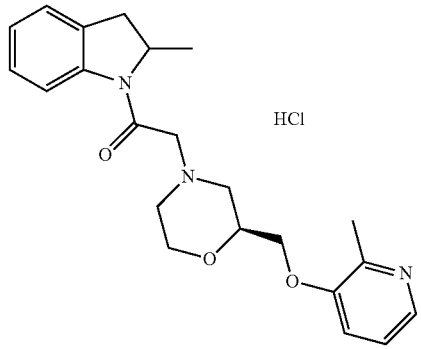 [SMILES: Cc1ncccc1OC[C@@H]1CN(CC(=O)N2c3ccccc3CC2C)CCO1 ; Cl]

Compound 60 was prepared following the procedure described in Lin et al. (1997), *J. Med. Chem.*, 40, pp 385-390. Compound 304 (Example 36; 50 mg, 0.175 mmol) and triphenylphosphine (70 mg, 0.26 mmol) were dissolved in dry THF (1 ml). Next DIAD; 0.052 ml, 0.26 mmol) and 2-methyl-3-hydroxypyridine (29 mg, 0.26 mmol) were added. The reaction mixture was stirred at RT for approximately 48 hours. The crude residue was purified twice by flash chromatography to afford the title compound as a colourless oil (36 mg; 52%). Analyses were performed on the free base, and it was converted to the HCl salt for testing.

¹H-NMR (500 MHz, CDCl₃) δ: 1.34 (bs, 3H, CH₃), 2.39 (t, 1H, J=11.0 Hz, 1 of (CH₂)₂N), 2.48-2.50 (m, 4H, Ar—CH₃+1 of (CH₂)₂N), 2.66-2.70 (m, 1H, Ar—CHH), 2.89-2.96 (m, 1H, 1 of (CH₂)₂N), 3.09-3.15 (m, 1H, 1 of (CH₂)₂N), 3.32-3.57 (m, 3H, Ar—CHH+COCH₂N), 3.82-3.89 (m, 1H, CH₂OCHCH₂OH), 3.99-4.05 (m, 2H, OCHCH₂OAr), 4.04-4.09 (m, 2H, CH₂OCHCH₂OAr), 4.73 (bs, 1H, CHCH₃), 7.07-7.10 (m, 1H, ArH), 7.24 (bs, 2H, ArH), 8.09-8.11 (m, 1H, ArH), 8.20 (bs, 1H, ArH).

¹³C-NMR (125 MHz, CDCl₃) δ: 19.4 (CH₃), 21.8 (CH₃), 36.6 (Ar—CH₂), 53.5 (CH₂)₂N), 55.5 (CH₂)₂N), 55.9 (CHCH₃), 61.6 (COCH₂N), 66.8 (CH₂O), 69.3 (CH₂O), 74.0 (CHCH₂O), 117.7, 121.6, 127.5 (ArCH), 140.8, 149.2, 153.0 (ArC), 166.8 (CON).

LCMS: m/z 382.2 ([M+H]⁺, 100%); Rt 4.4 min, purity >97.7% DAD (180-450).

Example 44

Compound 312

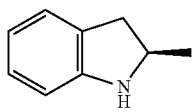

Compound 312 was prepared following the procedure described in *J. Org. Chem.*, (1978), pp 2285-2287. Compound 310 (490 mg, 2.10 mmol) was dissolved in a mix of MeOH/DCM and 0.5 ml of conc. HCl. The mixture was stirred at room temperature for approximately 24 hours. The solvents were then removed under reduced pressure. The residue was taken in $H_2O$ (15 ml) and the pH was adjusted to 8 with NaOH (5 ml). The clear solution became a milky suspension. The aqueous phase was extracted with DCM (4×15 ml). The organic portion was dried and concentrated to dryness to afford the product as a slightly pink oil (250 mg; 89%).

$^1$H-NMR (500 MHz, $CDCl_3$) δ: 1.21 (d, 3H, J=11.4 Hz, C$\underline{H}_3$), 2.56 (dd, 1H, $J_1$=15.4, $J_2$=7.7 Hz, Ar—CH$\underline{H}$), 3.06 (dd, 1H, $J_1$=15.4, $J_2$=8.5 Hz, Ar—C$\underline{H}$H), 3.69 (bs, 1H, N$\underline{H}$), 3.88-3.95 (m, 1H, C$\underline{H}$CH$_3$), 6.52 (dq, 1H, $J_1$=7.7, $J_2$=0.95 Hz, Ar$\underline{H}$), 6.6 (dt, 1H, $J_1$=7.4, $J_2$=1 Hz, Ar$\underline{H}$), 6.91-6.94 (m, 1H, Ar$\underline{H}$), 6.98-7.00 (m, 1H, Ar$\underline{H}$).

LCMS: m/z 134.1 ([M+H]$^+$, 100%); Rt 4.3 min, purity >94% DAD (180-450).

Example 45

Compound 313

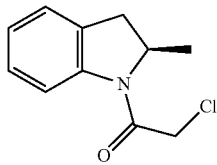

Compound 312 was prepared following the procedure described in *Biororg. Med. Chem. Lett.*, (2002), 12, pp 3111-3115. Chloroacetyl chloride (0.165 ml, 2.07 mmol) was added to a solution of compound 312 (250 mg, 1.88 mmol) and TEA (0.314 ml, 2.26 mmol) in DCM (6 ml). The mixture was stirred for approximately 3 hours at room temperature, and then quenched with water (5 ml). The phases were separated and the aqueous layer was extracted with DCM (3×5 ml). The combined organic portions were dried over $MgSO_4$ and concentrated to a dark brown residue, which was used for the next step without further purification (420 mg; quant.).

$^1$H-NMR (500 MHz, $CDCl_3$) δ: 1.27 (s, 3H, C$\underline{H}_3$), 2.50-2.65 (m, 1H, Ar—CH$\underline{H}$), 3.39 (bs, 1H, Ar—C$\underline{H}$H), 4.09-4.35 (m, 2H, C$\underline{H}_2$), 4.53 (bs, 1H, C$\underline{H}$CH$_3$), 7.02 (t, 1H, J=7.6 Hz, Ar$\underline{H}$), 7.16-7.19 (m, 2H, Ar$\underline{H}$), 8.10 (bs, 1H, Ar$\underline{H}$).

LCMS: m/z 210.0 ([M+H]$^+$, 100%); Rt 4.5 min, purity >95% DAD (180-450).

Example 46

Compound 314

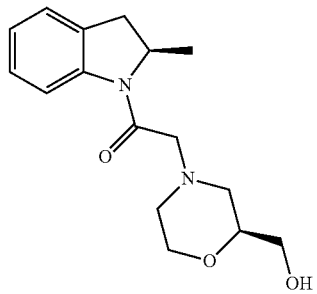 [SMILES: C[C@@H]1Cc2ccccc2N1C(=O)CN1CCO[C@H](CO)C1]

Essentially the same procedure was used to make compound 314 as was used for compound 404 (Example 36). A microwave vial was charged with 1-(chloroacetyl)-2-methylindoline (209 mg, 1.00 mmol), hydroxymethylmorpholine (compound 54; 220 mg, 1.88 mmol), triethylamine (0.28 ml, 2.00 mmol) and ACN (4 ml). The vial was sealed and irradiated for 30 min at 100° C.; the solvent was removed under reduced pressure; and the crude residue was purified by flash chromatography using a 040% gradient of (20% MeOH/DCM)/DCM. The product was obtained as a colourless oil, which solidified upon standing (234 mg; 80%).

$^1$H-NMR (500 MHz, $CDCl_3$) δ: 1.32 (bs, 3H, C$\underline{H}_3$), 1.99 (bs, 1H, 1 of (C$\underline{H}_2$)$_2$N), 2.26 (bs, 1H, 1 of (C$\underline{H}_2$)$_2$N), 2.40 (dt, 1H, $J_1$=11.2, $J_2$=3.3 Hz, Ar—CH$\underline{H}$), 2.68 (m, 1H, 1 of (C$\underline{H}_2$)$_2$N), 2.87 (m, 1H, 1 of (C$\underline{H}_2$)$_2$N), 2.93 (d, 1H, J=10.9 Hz, 1 of (C$\underline{H}_2$)$_2$N), 3.28-3.42 (m, 2H, Ar—CH$\underline{H}$+1 of COC$\underline{H}_2$N), 3.60-3.71 (m, 2H, OC$\underline{H}$CH$_2$OH), 3.79 (m, 2H, $J_1$=11.3, $J_2$=2.5 Hz, CH$_2$C$\underline{H}_2$O), 3.93-3.96 (m, 1H, 1 of OC$\underline{H}$CH$_2$OH), 4.73 (bs, 1H, C$\underline{H}$CH$_3$), 7.07 (t, 1H, J=8.0 Hz, Ar$\underline{H}$), 7.22-7.25 (m, 2H, Ar$\underline{H}$), 8.20 (bs, 1H, Ar$\underline{H}$).

$^{13}$C-NMR (125 MHz, $CDCl_3$) δ: 21.8 ($\underline{C}H_3$), 36.7 (Ar—$\underline{C}H_2$), 53.5 (($\underline{C}H_2$)$_2$N), 54.9 (($\underline{C}H_2$)$_2$N), 55.0 ($\underline{C}HCH_3$), 61.4 (CO$\underline{C}H_2$N), 64.0 ($\underline{C}H_2$OH), 66.2 ($\underline{C}H_2$O), 75.9 ($\underline{C}HCH_2$), 118.7, 124.0, 124.9, 127.5 (Ar$\underline{C}$H), 166.8 ($\underline{C}$ON).

LCMS: m/z 291.1 ([M+H]$^+$, 100%); Rt 4.2 min, purity >99% DAD (180-450).

Example 47

Compound 61

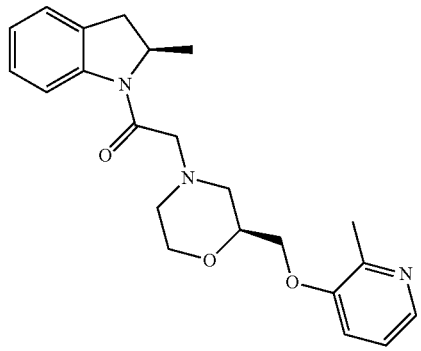 [SMILES: Cc1ncccc1OC[C@@H]1CN(CC(=O)N2c3ccccc3C[C@H]2C)CCO1]

Essentially the same procedure was used to make compound 61 as was used for compound 60 (Example 43), using compound 314 (39 mg, 0.134 mmol), 2-methyl-3-hydroxypyridine (22 mg, 0.20 mmol), triphenylphosphine (53 mg, 0.20 mmol), DIAD (0.04 ml, 0.201 mmol) and THF (1 ml). The product was obtained as a colourless oil (30 mg; 58%).

¹H-NMR (500 MHz, CDCl₃) δ: 1.34 (bs, 3H, C_H_₃), 2.39 (t, 1H, J=9.9 Hz, 1 of (C_H_₂)₂N), 2.46-2.51 (m, 4H, Ar—C_H_₃+1 of (C_H_₂)₂N), 2.49 (bd, 1H, J=14 Hz, Ar—C_H_H), 2.91 (bd, 1H, J=11.3 Hz, 1 of (C_H_₂)₂N), 3.15 (bd, 1H, J=12 Hz, 1 of (C_H_₂)₂N), 3.33-3.52 (m, 3H, Ar—CH_H_+COC_H_₂N), 3.85 (dt, 1H, J₁=11.3, J₂=2.4 Hz, CH₂OC_H_CH₂OH), 3.95-4.01 (m, 2H, OCHC_H_₂OAr), 4.07-4.09 (m, 2H, C_H_₂OCHCH₂OAr), 4.74 (bs, 1H, C_H_CH₃), 7.06-7.11 (m, 1H, Ar_H_), 7.23-7.26 (m, 2H, Ar_H_), 8.11 (dd, 1H, J₁=3.8, J₂=2.3 Hz, Ar_H_), 8.20 (bs, 1H, Ar_H_).

¹³C-NMR (125 MHz, CDCl₃) δ: 19.4 (_C_H₃), 21.9 (_C_H₃), 36.7 (Ar—_C_H₂), 53.0 (_C_H₂)₂N), 54.9 (_C_H₂)₂N), 55.9 (_C_HCH₃), 61.6 (CO_C_H₂), 66.8 (_C_H₂O), 69.3 (_C_H₂O), 73.9 (_C_HCH₂O), 117.7, 118.1, 121.6, 124.9, 127.5 (Ar_C_H), 140.8, 149.2, 153.0 (Ar_C_), 166.8 (_C_ON).

LCMS: m/z 382.2 ([M+H]⁺, 100%); Rt 4.5 min, purity >97.7% DAD (180-450).

Example 48

Compound 318

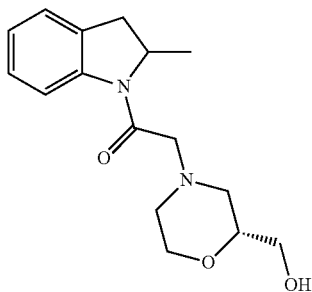 [SMILES: CC1Cc2ccccc2N1C(=O)CN1CCO[C@@H](CO)C1]

Essentially the same procedure was used to make compound 318 as was used for compound 309 (Example 41). A microwave vial was charged with compound 56 (Example 7; 167 mg, 1.43 mmol), 1-(chloroacetyl)-2-methylindoline (200 mg, 0.95 mmol), TEA (0.06 ml, 0.044 mmol) and ACN (1 ml). The vial was sealed and irradiated for 30 min at 100° C.; the solvent was removed under reduced pressure; and the crude residue was purified by flash chromatography using a 0→40% gradient of (20% MeOH/DCM)/DCM. The product was obtained as a colourless oil (282 mg; 99%).

¹H-NMR (500 MHz, CDCl₃) δ: 1.32 (bs, 3H, C_H_₃), 1.94 (bs, 1H, 1 of (C_H_₂)₂N), 2.22-2.27 (m, 1H, 1 of (C_H_₂)₂N), 2.43 (dt, 1H, J₁=11.2, J₂=3.3 Hz, Ar—C_H_H), 2.66-2.72 (m, 1H, 1 of (C_H_₂)₂N), 2.86-2.95 (m, 2H, 1 of (C_H_₂)₂N), 3.26-3.90 (m, 7H, Ar—CH_H_+COC_H_₂N+C_H_₂OCHC_H_₂OH), 3.91-3.98 (m, 1H, OC_H_CH₂OH), 4.73 (bs, 1H, C_H_CH₃), 7.07 (t, 1H, J=8.0 Hz, Ar_H_), 7.23-7.25 (m, 2H, Ar_H_), 8.20 (bs, 1H, Ar_H_).

LCMS: m/z 291.17 ([M+H]⁺, 100%); Rt 4.6 min, purity >99% DAD (180-450).

Example 49

Compound 319

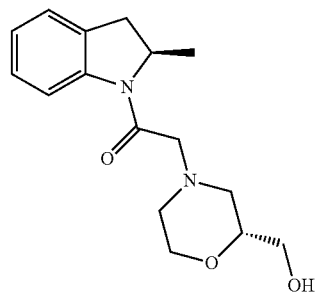 [SMILES: C[C@@H]1Cc2ccccc2N1C(=O)CN1CCO[C@@H](CO)C1]

Compound 319 was prepared using essentially the same procedure as for compound 318 (Example 48), from 1-(chloroacetyl)-2-methylindoline compound 313 (205 mg, 0.97 mmol), (R)-morpholin-2-ylmethanol (compound 56; 172 mg, 1.46 mmol), triethylamine (0.27 ml, 1.95 mmol) and ACN (1.5 ml). The crude residue was purified by flash chromatography using a 0→40% gradient of (20% MeOH/DCM)/DCM. The product was obtained as a colourless oil, which solidified on standing (217 mg; 77%).

¹H-NMR (500 MHz, CDCl₃) δ: 1.32 (bs, 3H, C_H_₃), 1.97 (bs, 1H, 1 of (C_H_₂)₂N), 2.25 (t, 1H, J=11.2 Hz, 1 of (C_H_₂)₂N), 2.43 (bs, 1H, Ar—C_H_H), 2.67-2.73 (m, 1H, 1 of (C_H_₂)₂N), 2.90 (d, 2H, J=11.7 HZ, 1 of (C_H_₂)₂N), 3.28-3.78 (7H, Ar—C_H_H+COC_H_₂N+C_H_₂OCHC_H_₂OH), 3.84 (t, 1H, J=12 Hz, 1 of CH₂C_H_₂O), 3.91-3.96 (m, 1H, OC_H_CH₂OH), 4.73 (bs, 1H, C_H_CH₃), 7.08 (t, 1H, J=8.0 Hz, Ar_H_), 7.23-7.25 (m, 2H, Ar_H_), 8.19 (bs, 1H, Ar_H_).

LCMS: m/z 291.1 ([M+H]⁺, 100%); Rt 4.6 min, purity >99% DAD (180-450).

Example 50

Compound 62

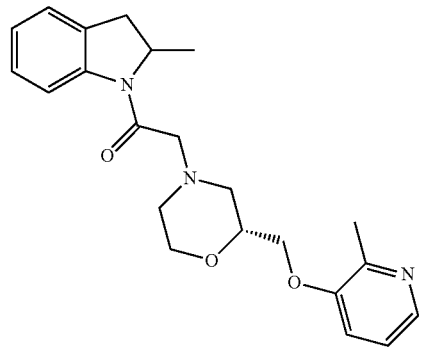 [SMILES: Cc1ncccc1OC[C@H]1CN(CC(=O)N2c3ccccc3CC2C)CCO1]

Essentially the same procedure was used to make compound 62 as was used for compound 60 (Example 43) and compound 61 (Example 47), except using compound 318 (50 mg, 0.172 mmol), 2-methyl-3-hydroxypyridine (28 mg, 0.26 mmol), triphenylphosphine (68 mg, 0.26 mmol), DIAD (0.05 ml, 0.26 mmol) and THF (1 ml). The product was obtained as a colourless oil (24 mg; 36%).

¹H-NMR (500 MHz, CDCl₃) δ: 1.33 (bs, 3H, CH₃), 2.39 (t, 1H, J=9.8 Hz, 1 of (CH₂)₂N), 2.49-2.51 (m, 4H, Ar—CH₃+1 of (CH₂)₂N), 2.67-2.71 (m, 1H, Ar—CHH), 2.90-2.96 (m, 1H, 1 of (CH₂)₂N), 3.09-3.16 (m, 1H, 1 of (CH₂)₂N), 3.33-3.53 (m, 3H, Ar—CHH+COCH₂N), 3.82-3.90 (m, 1H, CH₂OCHCH₂OH), 3.96-4.01 (m, 2H, OCHCH₂OAr), 4.07-4.10 (m, 2H, CH₂OCHCH₂OAr), 4.74 (bs, 1H, CHCH₃), 7.08-7.10 (m, 1H, ArH), 7.24 (bs, 2H, ArH), 8.10-8.12 (m, 1H, ArH), 8.20 (bs, 1H, ArH).

¹³C-NMR (125 MHz, CDCl₃) δ: 19.4 (CH₃), 21.8 (CH₃), 36.6 (Ar—CH₂), 53.0, 53.4 (CH₂)₂N), 54.9 (CH₂)₂N), 55.5, 55.9 (CHCH₃), 61.6 (COCH₂N), 66.8 (CH₂O), 69.3 (CH₂O), 73.9 (CHCH₂O), 117.7, 118.1, 121.6, 124.9, 127.5 (ArCH), 140.8, 149.2, 153.0 (ArC), 166.8 (CON).

LCMS: m/z 382.2 ([M+H]⁺, 100%); Rt 4.9 min, purity >99% DAD (180-450).

Example 51

Compound 63

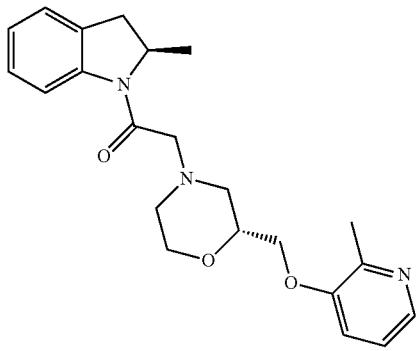 [SMILES: Cc1ncccc1OC[C@H]1CN(CC(=O)N2c3ccccc3C[C@H]2C)CCO1]

Essentially the same procedure was used to make compound 63 as was used for compounds 60 to 62, except using compound 319 (50 mg, 0.172 mmol), 2-methyl-3-hydroxypyridine (28 mg, 0.26 mmol), triphenylphosphine (68 mg, 0.26 mmol), DIAD (0.05 ml, 0.26 mmol) and THF (1 ml). The product was obtained as a colourless oil (27 mg; 41%).

¹H-NMR (500 MHz, CDCl₃) δ: 1.32 (bs, 3H, CH₃), 2.39 (t, 1H, J=11 Hz, 1 of (CH₂)₂N), 2.49 (s, 3H, Ar—CH₃), 2.67-2.71 (m, 1H, Ar—CHH), 2.95 (d, 1H, J=12.4 Hz, 1 of (CH₂)₂N), 3.09-3.12 (m, 1H, 1 of (CH₂)₂N), 3.23-3.53 (m, 3H, Ar—CHH+COCH₂N), 3.88 (t, 1H, J=12.0 Hz, CH₂OCHCH₂OH), 3.96-3.99 (m, 2H, OCHCH₂OAr), 4.04-4.07 (m, 2H, CH₂OCHCH₂OAr), 4.73 (bs, 1H, CHCH₃), 7.06-7.09 (m, 2H, ArH), 7.23-7.25 (m, 2H, ArH), 8.11 (t, 1H, J=3.1 Hz, ArH), 8.20 (bs, 1H, ArH).

¹³C-NMR (125 MHz, CDCl₃) δ: 19.4 (CH₃), 21.8 (CH₃), 36.6 (Ar—CH₂), 53.4 (CH₂)₂N), 54.9 (CH₂)₂N), 55.5 (CHCH₃), 61.6 (COCH₂N), 66.7 (CH₂O), 69.3 (CH₂O), 74.0 (CHCH₂O), 117.7, 118.1, 121.6, 124.9, 127.5 (ArCH), 140.8, 149.2, 152.9 (ArC), 166.8 (CON).

LCMS: m/z 382.2 ([M+H]⁺, 100%); Rt 4.7 min, purity >99% DAD (180-450).

Example 52

Compound 64

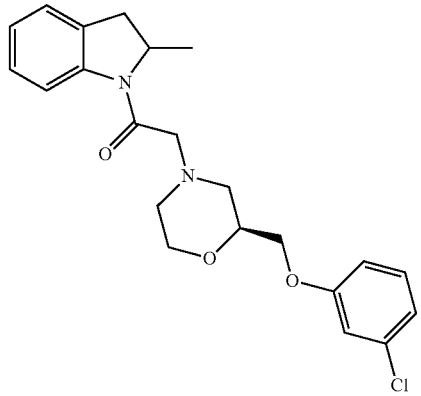 [SMILES: CC1Cc2ccccc2N1C(=O)CN1CCO[C@H](COc2cccc(Cl)c2)C1]

Essentially the same procedure was used to make compound 64 as was used for compounds 60 to 63, except using compound 304 (50 mg, 0.17 mmol), 3-chlorophenol (37 mg, 0.29 mmol), triphenylphosphine (76 mg, 0.29 mmol), DEAD (0.05 ml, 0.3 mmol) and THF (1 ml). The crude residue was purified twice by flash chromatography to afford the title compound as colourless oil (15 mg; 22%). The product was converted into the HCl salt for assaying.

Example 53

Compound 65

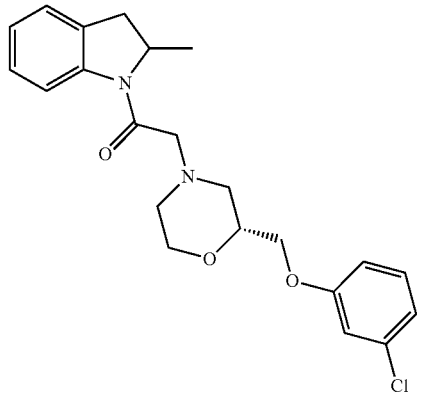 [SMILES: CC1Cc2ccccc2N1C(=O)CN1CCO[C@@H](COc2cccc(Cl)c2)C1]

Essentially the same procedure was used to make compound 65 as was used for compounds 60 to 64, except using compound 304 (50 mg, 0.17 mmol), 3-chlorophenol (33 mg, 0.26 mmol), triphenylphosphine (70 mg, 0.26 mmol), DEAD (0.05 ml, 0.3 mmol) and THF (1 ml). The crude residue was purified twice by flash chromatography to afford the title compound as colourless oil (33 mg; 48%). The product was converted into the HCl salt for assaying.

Example 54

Compound 66

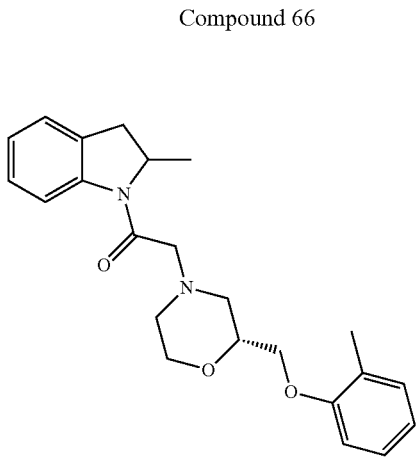

Essentially the same procedure was used to make compound 66 as was used for compounds 60 to 65, except using compound 304 (50 mg, 0.17 mmol), 2-methylphenol (0.027 ml, 0.26 mmol), triphenylphosphine (70 mg, 0.26 mmol), DEAD (0.05 ml, 0.3 mmol) and THF (1 ml). The crude residue was purified twice by flash chromatography to afford the title compound as colourless oil (23 mg; 35%). The product was converted into the HCl salt for assaying.

Example 55

Compound 67

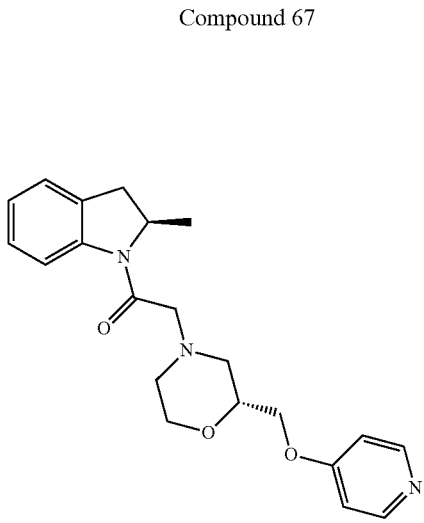

Compound 319 (Example 49; 98 mg, 0.34 mmol, 1 eq.) and PPh$_3$ (138 mg, 0.53 mmol, 1.5 eq.) were dissolved in dry THF (2 ml). Next DIAD (104 μl, 0.53 mmol, 1.5 eq.) and 4-hydroxypyridine (50 mg, 0.53 mmol, 1.5 eq.) were added. The reaction mixture was stirred at RT for approximately 16 hrs. After this time, the solvent was removed and the crude mixture purified by flash column chromatography (silica, DCM/MeOH 1:0 to 8:2) to afford the title compound.

Example 56

Compound 68

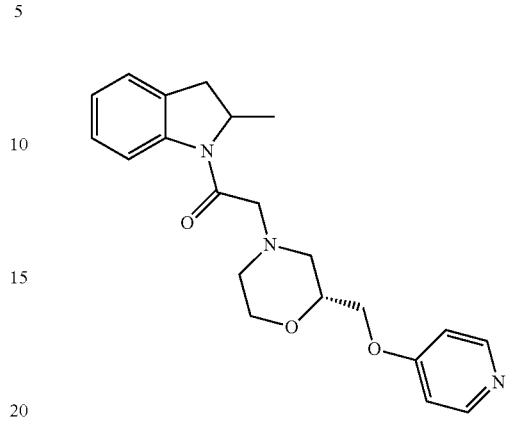

Compound 318 (Example 48; 98 mg, 0.34 mmol, 1 eq.) and PPh$_3$ (138 mg, 0.53 mmol, 1.5 eq.) were dissolved in dry THF (2 ml). Next DIAD (104 μl, 0.53 mmol, 1.5 eq.) and 4-hydroxypyridine (50 mg, 0.53 mmol, 1.5 eq.) were added. The reaction mixture was stirred at RT for approximately 16 hrs, after which the solvent was removed and the crude mixture purified by flash column chromatography (silica, DCM/MeOH 1:0 to 8:2) to afford compound 68 as a white foam (73 mg; 59%).

Example 57

Compound 69

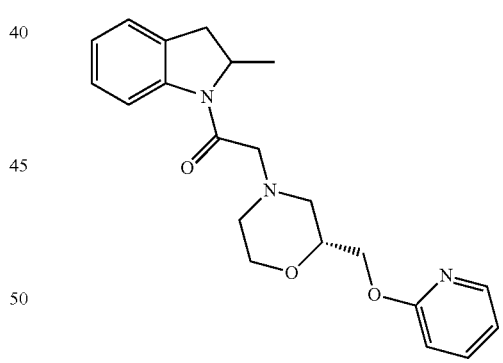

Compound 318 (Example 48; 80 mg, 0.28 mmol, 1 eq.) and NaH (13 mg, 0.55 mmol, 2 eq.) were placed in a microwave vial. Dry THF (2 ml) was added and the mixture was stirred at RT for 5 min before 2-bromopyridine (52 μl, 0.55 mmol, 2 eq.) was added. The vial was sealed and irradiated with microwaves for 1.5 hours at 170° C. After this time the solvent was removed and the crude mixture purified by flash column chromatography (silica, DCM/MeOH 1:0 to 92:8) to afford the title compound as a white foam (47 mg, 46%).

$^1$H-NMR (500 MHz, CDCl$_3$) δ: 1.30 (bs, 3H, Me), 2.30 (t, 1H, J=10.6 Hz, 1 of a), 2.43 (td, 1H, J=11.3, 3.2 Hz, 1 of d), 2.66 (d, 1H, J=15.6 Hz, 1 of f), 2.82-2.95 (2 d, 1H, J=10.5 Hz, 1 of a (2 rotamers)), 2.97-3.10 (m, 1H, 1 of d), 3.22-3.52 (m, 3H, 1 of f+i), 3.77-3.90 (m, 1H, 1 of e), 3.93-4.11 (m, 2H, b+1 of e), 4.32-4.38 (m, 2H, c), 4.66-5.00 (2 bs, 1H, g (2 rotamers)), 6.77-6.83 (m, 1H, ArH), 6.83-6.88 (m, 1H, ArH), 7.05 (t, 1H, J=7.5 Hz, ArH), 7.18-7.25 (m, 2H, ArH), 7.52-7.59 (m, 1H, ArH), 8.09-8.15 (m, 1H, ArH), 8.17 (d, 1H, J=6.3 Hz, ArH).

$^{13}$C-NMR (125 MHz, CDCl$_3$) δ: 21.8 (CH$_3$), 36.6 (f), 53.0 (d*), 53.5 (d), 54.9 (g), 55.3 (a*), 55.7 (a), 61.7 (i*), 61.8 (i), 66.6 (c), 66.7 (e*), 66.8 (e), 74.07 (b), 74.11 (b*), 111.3, 116.9, 118.1, 124.1, 125.0, 127.5 (ArCH), 130.2 (ArC), 138.51 (ArCH), 138.56 (ArCH*), 141.6 (ArC), 146.70 (ArCH*), 146.72 (ArCH), 163.4 (ArC*), 163.5 (ArC), 166.8 (h).

LCMS: m/z 368.1975 ([M+H]$^+$, 100%) (calc. 368.1969); Rt 5.1 min DAD (180-450).

Example 58

Compound 70

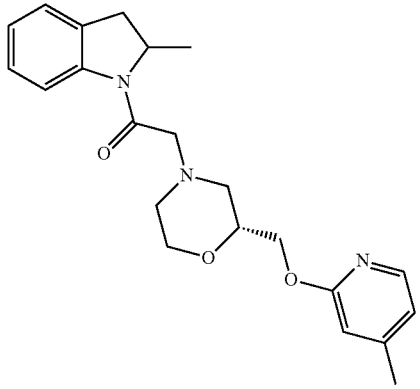

GFR-VII-318 (80 mg, 0.28 mmol, 1 eq.) and NaH (13 mg, 0.55 mmol, 2 eq.) were placed in a microwave vial. Dry THF (2 ml) was added and the mixture was stirred at RT for 5 min before 2-bromo-4-methylpyridine (92 μl, 0.83 mmol, 3 eq.) was added. The vial was sealed and irradiated with microwaves for 1.5 hours at 170° C. After this time the solvent was removed and the crude mixture purified by flash column chromatography (silica, DCM/MeOH 1:0 to 92:8) to afford compound 70 as white foam (31 mg; 29%).

$^1$H-NMR (500 MHz, CDCl$_3$) δ: 1.28 (bs, 3H, Me), 2.22-2.32 (m, 4H, 1 of a+Ar—CH$_3$), 2.41 (td, 1H, J=11.2, 3.2 Hz, 1 of d), 2.63 (d, 1H, J=14.6 Hz, 1 of f), 2.80-2.94 (2 d, 1H, J=10.9 Hz, 1 of a (2 rotamers)), 3.01 (t, 1H, J=11.2 Hz, 1 of d), 3.18-3.60 (m, 3H, 1 of f+i), 3.73-3.86 (m, 1H, 1 of e), 3.90-4.07 (m, 2H, b+1 of e), 4.28-4.37 (m, 2H, c), 4.62-5.02 (2 bs, 1H, g (2 rotamers)), 6.57-6.62 (m, 1H, ArH), 6.66 (t, 1H, J=5.8 Hz, ArH), 7.03 (t, 1H, J=7.4 Hz, ArH), 7.15-7.23 (m, 2H, ArH), 7.95 (dd, 1H, J=8.0, 5.3 Hz, ArH), 8.16 (apparent bs, 1H, ArH).

$^{13}$C-NMR (125 MHz, CDCl$_3$) δ: 20.9 (ArCH$_3$), 21.8 (CH$_3$), 36.6 (f), 53.0 (d*), 53.5 (d), 54.9 (g), 55.3 (a*), 55.7 (a), 61.8 (i*), 61.9 (i), 66.6 (c), 66.70 (e*), 66.74 (e), 74.10 (b), 74.14 (b*), 111.3, 118.1, 118.5, 124.1, 125.0, 127.5 (ArCH), 130.3 (ArC), 141.6 (ArC), 146.21 (ArCH*), 146.22 (ArCH), 149.8 (ArCH*), 149.9 (ArCH), 163.77 (ArC*), 163.78 (ArC), 166.9 (h).

LCMS: m/z 382.2125 ([M+H]$^+$, 100%) (calc. 382.2124); Rt 5.3 min DAD (180-450).

Example 59

(S)-2-((4-fluorophenoxy)methyl)-4-(2-(indolin-1-yl)ethyl)morpholine hydrochloride (Compound 32s)

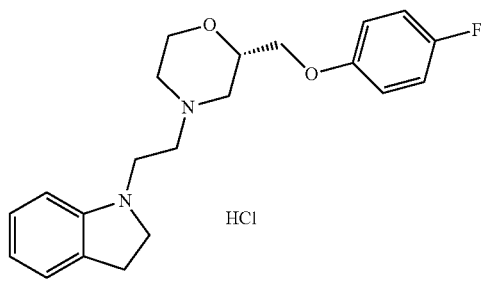

Compound 32s was synthesised with essentially the same procedure as compound 18s (Example 16), from compound 51 (Example 10; 200 mg, 0.70 mmol), 4-fluorophenol (128 mg, 1.14 mmol), triphenylphosphine (304 mg, 1.14 mmol), DIAD (0.2 ml, 1.14 mmol), and THF (1.5 ml). The crude residue was purified twice by flash column chromatography (silica, DCM/MeOH 1:0 to 94:6, followed by Hex/EtOAc 1:0 to 0:1) to afford the title compound as an oil (235 mg; 86%). Analyses were performed on the free base, and the free base was converted to the HCl salt for testing.

$^1$H-NMR (500 MHz, DMSO-d6) δ: 2.76-2.83 (m, 2H, J=8.24 Hz, 2 of (CH$_2$)$_2$N), 3.25-3.30 (t, 3H, J=8.46 Hz, 2 of N(CH$_2$)$_2$N+1 of (CH$_2$)$_2$N), 3.35-3.44 (m, 2H, ArCH$_2$CH$_2$N, 3.47-3.57 (m, 4H, +1 of (CH$_2$)$_2$N), 1 of N(CH$_2$)$_2$N), 2 of ArCH$_2$CH$_2$N), 3.77 (td, 1H, 1 of OCH$_2$CH$_2$), 3.91-4.01 (m, 3H, OCH+2 of OCH$_2$CH$_2$+1 of OCH$_2$CH), 4.06-4.09 (m, 1H, 1 of OCH$_2$CH), 4.26-4.27 (m, 1H, 1 of OCH$_2$CH), 6.54-6.57 (dt, 1H, J=7.20 Hz, ArH), 6.61-6.63 (m, 1H, ArH), 6.88-6.93 (m, 1H, ArH), 6.97-7.03 (m, 3H, J=8.64 Hz, ArH), 7.07-7.11 (d, 2H, J=8.64 Hz, ArH).

LCMS: m/z 357.1998 ([M+H]$^+$, 100%); Rt 5.8 min, purity=91% DAD (180-450 nm).

The compound was re-purified to assay (235 mg, purity 100%), and converted to the HCl salt (white solid) for testing.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the scope of the invention, which is defined by the claims.

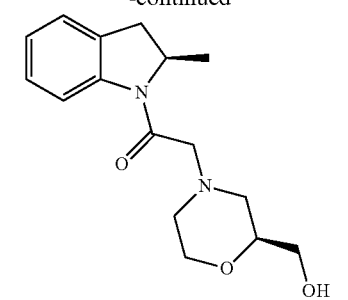

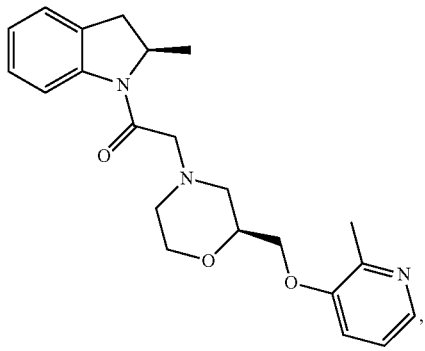

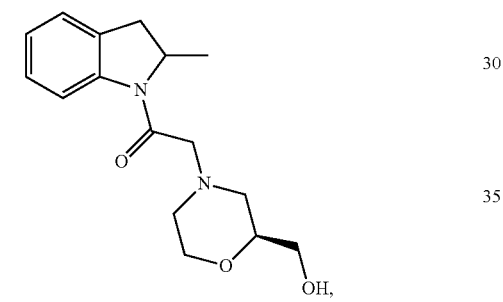

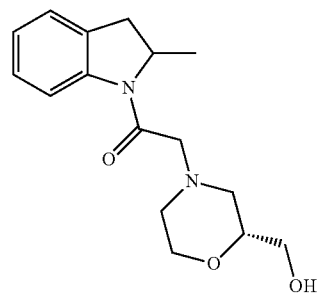

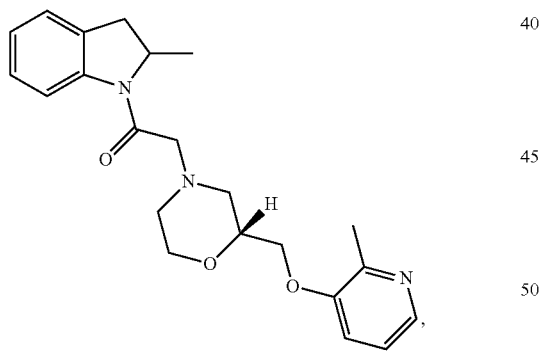

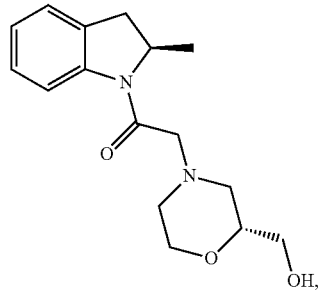

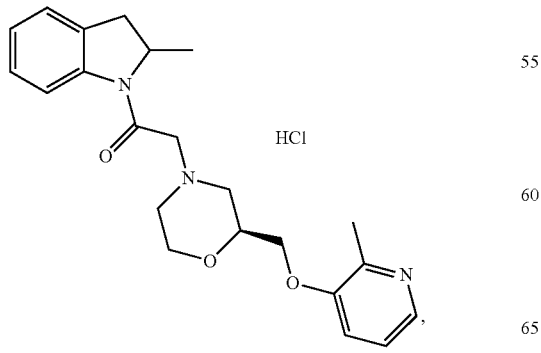

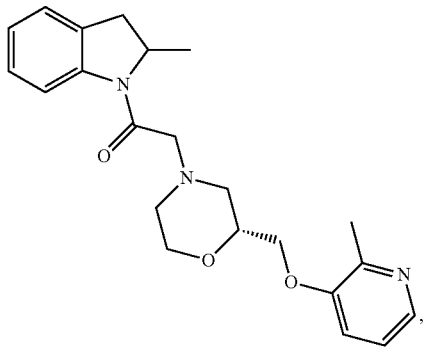

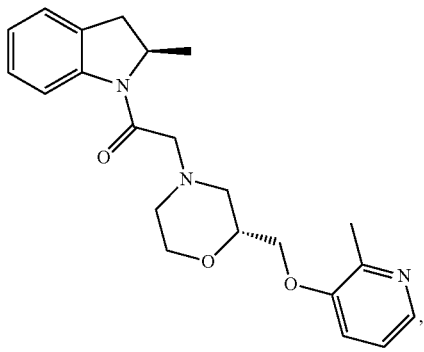 [SMILES: C[C@@H]1Cc2ccccc2N1C(=O)CN1CCO[C@@H](COc2ccncc2)C1]
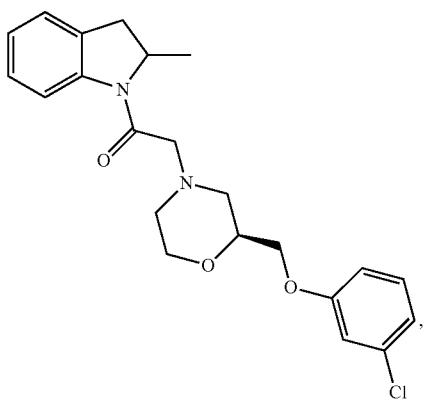
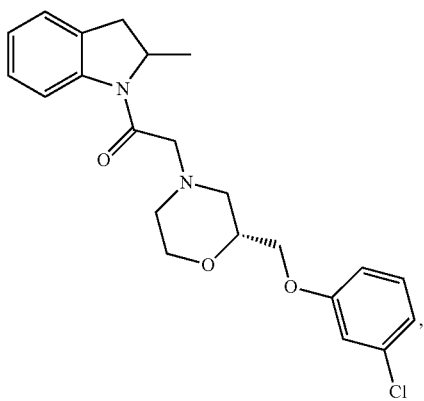
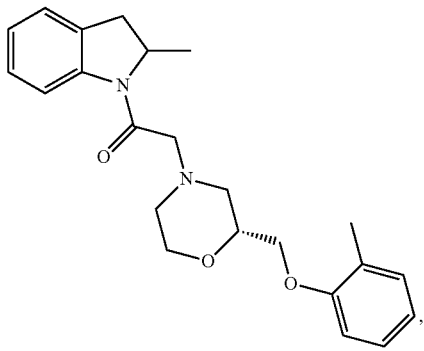
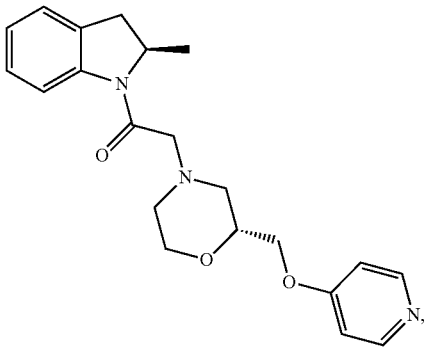
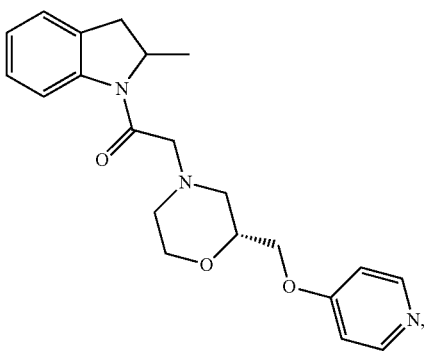
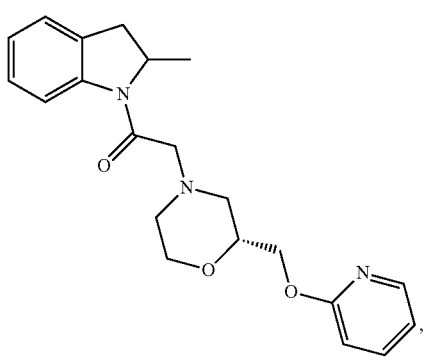 [SMILES: CC1Cc2ccccc2N1C(=O)CN1CCO[C@@H](COc2ccncc2)C1]
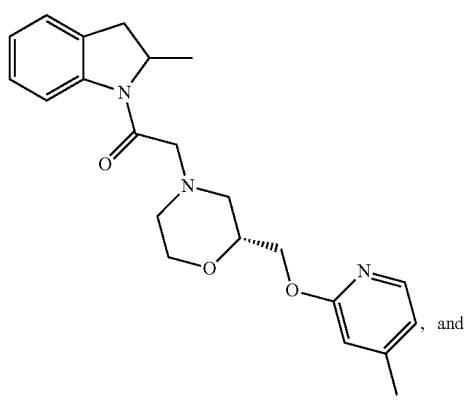

-continued
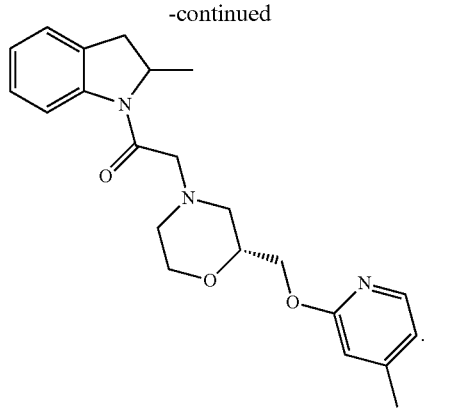

The invention claimed is:
1. A compound of Formula I:

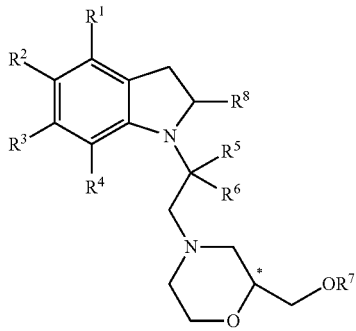

Formula I or a stereoisomer or a pharmaceutically acceptable salt or solvate thereof, wherein:

$R^1$, $R^2$, $R^3$ and $R^4$ are each independently selected from the group consisting of: hydrogen, halogen, hydroxy, optionally substituted alkyl, and optionally substituted alkoxy;

$R^5$ and $R^6$ are each hydrogen, or $R^5$ and $R^6$ together are =O;

$R^7$ is hydrogen, optionally substituted alkyl, optionally substituted alkenyl, optionally substituted alkynyl, optionally substituted alkoxy, optionally substituted aryl, optionally substituted arylalkyl, optionally substituted heteroaryl, optionally substituted cycloalkyl, optionally substituted heterocycloalkyl, alkylcarbonyl, or —C(O)—$R^a$;

$R^a$ is selected from the group consisting of: H, $(C_1$-$C_6)$ alkyl, $(C_1$-$C_6)$alkoxy, halo$(C_1$-$C_6)$alkyl, hydroxy$(C_1$-$C_6)$alkyl, $(C_5$-$C_6)$aryl, halo$(C_5$-$C_6)$aryl, hydroxy$(C_5$-$C_6)$aryl, alkoxy$(C_5$-$C_6)$aryl, $(C_5$-$C_6)$aryloxy, a 5 or 6 membered heteroaryl optionally substituted with halogen, hydroxy or alkoxy; and a 4 to 6 membered heterocycloalkyl optionally substituted with halogen, hydroxy or alkoxy;

$R^8$ is hydrogen or optionally substituted alkyl;

and the configuration at * is (R), (S) or a racemic mixture.

2. The compound of claim 1, wherein:
$R^1$, $R^2$, $R^3$ and $R^4$ are each independently hydrogen, chloro, fluoro, bromo, hydroxy, methyl, ethyl, methoxy, ethoxy, chloro$(C_1$-$C_2)$alkyl, or hydroxy$(C_1$-$C_2)$alkyl.

3. The compound of claim 1, wherein:
$R^7$ is hydrogen, optionally substituted $(C_1$-$C_6)$alkyl, optionally substituted $(C_5$-$C_{15})$aryl, optionally substituted $(C_5$-$C_{15})$aryl$(C_1$-$C_6)$alkyl, an optionally substituted 5 to 15 membered heteroaryl, or an optionally substituted 4 to 15 membered heterocycloalkyl.

4. The compound of claim 1, wherein $R^7$ is:

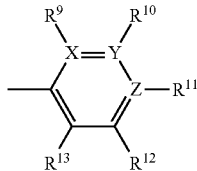

wherein:
X, Y and Z are independently C or N; and
where present, $R^9$, $R^{10}$, $R^{11}$, $R^{12}$ and $R^{13}$ are each independently selected from the group consisting of hydrogen, $(C_1$-$C_6)$alkyl, $(C_1$-$C_6)$alkoxy, halo$(C_1$-$C_6)$alkyl, hydroxy$(C_1$-$C_6)$alkyl, $(C_5$-$C_6)$aryl, halo$(C_5$-$C_6)$aryl, hydroxy$(C_5$-$C_6)$aryl, alkoxy$(C_5$-$C_6)$aryl, $(C_5$-$C_6)$aryloxy, a 5 or 6 membered heteroaryl optionally substituted with halogen, hydroxy or alkoxy; and a 4 to 6 membered heterocycloalkyl optionally substituted with halogen, hydroxy or alkoxy; and
optionally, wherein two adjacent $R^9$, $R^{10}$, $R^{11}$, $R^{12}$ and $R^{13}$ groups are joined together with the ring atoms to which they are attached to form a ring selected from the group consisting of: an optionally substituted 4- to 6-membered cycloalkyl or heterocycloalkyl and an optionally substituted 5- or 6-membered aryl or heteroaryl group, the optional are one or more of hydroxyl, fluoro, chloro, bromo, methoxy, ethoxy, chloro$(C_1$-$C_2)$alkyl, and hydroxy$(C_1$-$C_2)$alkyl, —CN, —$CF_3$, —$NO_2$, —$NH_2$, or —NH$(C_1$-$C_4)$alkyl.

5. The compound of claim 4, wherein at least one of $R^9$, $R^{10}$, $R^{11}$, $R^{12}$ and $R^{13}$ is independently chloro, fluoro, methyl, ethyl, methoxy, or ethoxy; and the rest, where present, are hydrogen.

6. The compound of claim 1, wherein $R^7$ is selected from the group consisting of: phenyl; 2-, 3- or 4-methylphenyl; 2-, 3- or 4-chlorophenyl; 2-, 3- or 4-fluorophenyl, 2-, 3- or 4-methoxyphenyl; 2-, 3- or 4-pyridyl; 3-, 4-, 5- or 6-methylpyridin-2-yl; 3-, 4-, 5- or 6-chloropyridin-2-yl; 3-, 4-, 5- or 6-fluoropyridin-2-yl; 3-, 4-, 5- or 6-methoxypyridin-2-yl; 2-, 4-, 5- or 6-methylpyridin-3-yl; 2-, 4-, 5- or 6-chloropyridin-3-yl; 2-, 4-, 5- or 6-fluoropyridin-3-yl; 2-, 4-, 5- or 6-methoxypyridin-3-yl; 2- or 3-methylpyridin-4-yl; and 2- or 3-chloropyridin-4-yl; 2- or 3-fluoropyridin-4-yl; 2- or 3-methoxypyridin-4-yl.

7. The compound of claim 1, wherein $R^8$ is hydrogen, methyl, ethyl, chloro$(C_1$-$C_2)$alkyl, or hydroxy$(C_1$-$C_2)$alkyl.

8. The compound of claim 1, wherein unless otherwise defined, the optional substituent is selected from the group consisting of: halogen, hydroxy, amino, thiol, cyano, $(C_1$-$C_6)$ alkyl, $(C_1$-$C_6)$alkoxy, $(C_1$-$C_6)$alkenyl, $(C_1$-$C_6)$alkynyl, aryl, aryl$(C_1$-$C_6)$alkyl, aryl$(C_1$-$C_6)$alkoxy, heteroaryl, $(C_1$-$C_6)$ alkylthio, oxo, halo$(C_1$-$C_6)$alkyl, hydroxy$(C_1$-$C_6)$alkyl, nitro, phosphate, azido, $(C_1$-$C_6)$alkoxycarbonyl, carboxy, $(C_1$-$C_6)$alkylcarboxy, $(C_1$-$C_6)$alkylamino, di$(C_1$-$C_6)$alkylamino, amino$(C_1$-$C_6)$alkyl, $(C_1$-$C_6)$alkylamino$(C_1$-$C_6)$ alkyl, di$(C_1$-$C_6)$alkylamino$(C_1$-$C_6)$alkyl, thio$(C_1$-$C_6)$alkyl, $(C_1$-$C_6)$alkylsulfonyl, arylsulfinyl, $(C_1$-$C_6)$alkylaminosulfonyl, arylaminosulfonyl, $(C_1$-$C_6)$alkylsulfonylamino, arylsulfonylamino, carbamoyl, $(C_1$-$C_6)$alkylcarbamoyl, di$(C_1$-$C_6)$ alkylcarbamoyl, arylcarbamoyl, $(C_1$-$C_6)$ alkylcarbonylamino, arylcarbonylamino, $(C_1$-$C_6)$cycloalkyl, and heterocycloalkyl.

9. The compound of claim 1, wherein unless otherwise defined, the optional substituent is chloro, methyl, ethyl, methoxy or ethoxy, wherein methyl, ethyl, methoxy and ethoxy are optionally substituted by one or more chloro.

10. The compound of claim 1, wherein:
$R^1$, $R^2$, $R^3$ and $R^4$ are each independently hydrogen, chloro, methyl, or methoxy;
$R^5$ and $R^6$ are each hydrogen, or $R^5$ and $R^6$ together are =O;
$R^7$ is hydrogen, optionally substituted $(C_1$-$C_6)$alkyl, optionally substituted $(C_5$-$C_6)$aryl, optionally substituted 5- or 6-membered heteroaryl, optionally substituted $(C_4$-$C_6)$cycloalkyl, optionally substituted 4- to 6-membered heterocycloalkyl, —CHO, or —C(O)($C_1$-$C_6)$alkyl; wherein when substituted, the substituent is 1, 2 or 3 substituents selected from the group consisting of methyl, ethyl, chloro, methoxy, and ethoxy;

$R^8$ is hydrogen or methyl;

and the configuration at * is (R) or (S) or a racemic mixture.

11. A pharmaceutical composition comprising one or more compound of Formula I,

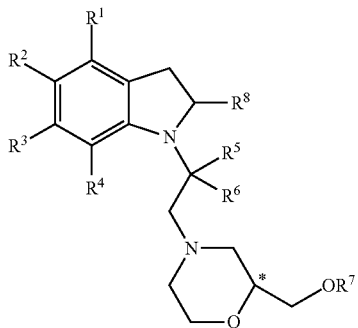

Formula I or a stereoisomer, or a pharmaceutically acceptable salt or solvate thereof, and a pharmaceutically acceptable carrier, wherein $R^1$, $R^2$, $R^3$ and $R^4$ are each independently selected from the group consisting of: hydrogen, halogen, hydroxy, optionally substituted alkyl, optionally substituted alkoxy;

$R^5$ and $R^6$ are each hydrogen, or $R^5$ and $R^6$ together are =O;

$R^7$ is hydrogen, optionally substituted alkyl, optionally substituted alkenyl, optionally substituted alkynyl, optionally substituted alkoxy, optionally substituted aryl, optionally substituted arylalkyl, optionally substituted heteroaryl, optionally substituted cycloalkyl, optionally substituted heterocycloalkyl, alkylcarbonyl, or —C(O)—$R^a$;

$R^a$ is selected from the group consisting of: H, ($C_1$-$C_6$)alkyl, ($C_1$-$C_6$)alkoxy, halo($C_1$-$C_6$)alkyl, hydroxy($C_1$-$C_6$)alkyl, ($C_5$-$C_6$)aryl, halo($C_5$-$C_6$)aryl, hydroxy($C_5$-$C_6$)aryl, alkoxy($C_5$-$C_6$)aryl, ($C_5$-$C_6$)aryloxy, a 5 or 6 membered heteroaryl optionally substituted with halogen, hydroxy or alkoxy; and a 4 to 6 membered heterocycloalkyl optionally substituted with halogen, hydroxy or alkoxy;

$R^8$ is hydrogen or optionally substituted alkyl;

and the configuration at * is (R), (S) or a racemic mixture.

12. A process for preparing a compound of claim 1, the process comprising:

(a) reacting a compound of Formula XIII:

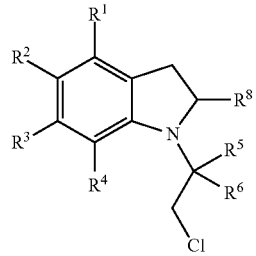

Formula XIII with a compound of Formula XIV:

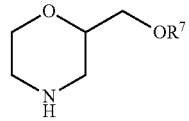

Formula XIV wherein $R^1$, $R^2$, $R^3$, $R^4$, $R^5$, $R^6$, $R^7$ and $R^8$ are as defined in claim 1.

13. The process of claim 12, wherein step (a) is carried out in the presence of:
(i) a base; or (ii) a solvent.

14. The process of claim 12, further comprising:
(b) reacting the product of step (a) with a compound of formula $R^7$-LG to form a compound of Formula I:

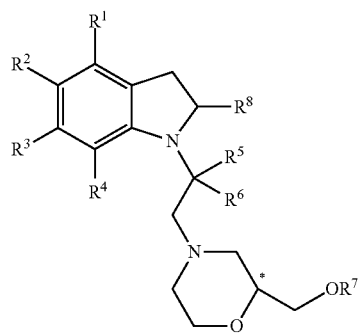

Formula I wherein LG is a leaving group, and wherein $R^7$ is defined according to claim 1.

15. The process of claim 14, wherein step (b) is a Mitsunobu reaction.

16. The process of claim 14, wherein step (b) is carried out in the presence of:
(i) a base;
(ii) diethyl azodicarboxylate (DEAD) or (iii) an organic solvent.

17. The compound of claim 1, wherein $R^1$, $R^2$, $R^3$ and $R^4$ are each independently hydrogen, halogen, hydroxy, alkyl, or alkoxy; and $R^7$ is hydrogen, alkyl, alkenyl, alkynyl, alkoxy, aryl, or arylalkyl.

18. The compound of claim 1, which is selected from the group consisting of:

(S)-2-(2-(hydroxymethyl)morpholino)-1-(indolin-1-yl)ethanone, (R)-2-(2-(hydroxymethyl)morpholino)-1-(indolin-1-yl)ethanone, (S)-(4-(2-(indolin-1-yl)ethyl)morpholin-2-yl)methanol, (R)-(4-(2-(indolin-1-yl)ethyl)morpholin-2-yl)methanol, (R)-1-(indolin-1-yl)-2-(2-((pyridin-2-yloxy)methyl)morpholino)ethanone, (R)-4-(2-(indolin-1-yl)ethyl)-2-((pyridin-2-yloxy)methyl)morpholine, (R)-1-(indolin-1-yl)-2-(2-(((4-methylpyridin-2-yl)oxy)methyl)morpholino)ethanone, (R)-4-(2-(indolin-1-yl)ethyl)-2-(((4-methylpyridin-2-yl)oxy)methyl)morpholine, (S)-1-(indolin-1-yl)-2-(2-(phenoxymethyl)morpholino)ethanone, (S)-4-(2-(indolin-1-yl)ethyl)-2-(phenoxymethyl)morpholine, (R)-1-(indolin-1-yl)-2-(2-((pyridin-3-yloxy)methyl)morpholino)ethanone, (R)-4-(2-(indolin-1-yl)ethyl)-2-((pyridin-3-yloxy)methyl)morpholine, (S)-1-(indolin- 1-yl)-2-(2-((pyridin-3-yloxy)methyl)morpholino) ethanone, (S)-4-(2-(indolin-1-yl)ethyl)-2-((pyridin-3-yloxy)methyl)morpholine, (R)-2-(2-((3-chlorophenoxy)methyl)morpholino)-1-(indolin-1-yl)ethanone, (R)-2-((3-chlorophenoxy)methyl)-4-(2-(indolin-1-yl)ethyl)morpholine, (S)-2-(2-((3-chlorophenoxy)methyl)morpholino)-1-(indolin-1-yl)ethanone, (S)-2-((3-chlorophenoxy)methyl)-4-(2-(indolin-1-yl)ethyl)morpholine, (S)-1-(indolin-1-yl)-2-(2-((3-methoxyphenoxy)methyl)morpholino)ethanone, (S)-4-(2-(indolin-1-yl)ethyl)-2-((3-methoxyphenoxy)methyl)morpholine, (R)-4-(2-(indolin-1-yl)ethyl)-2-((3-methoxyphenoxy)methyl)morpholine, (R)-4-(2-(indolin-1-yl)ethyl)-2-(((2-methylpyridin-3-yl)oxy)methyl)morpholine, (S)-4-(2-(indolin-1-yl)ethyl)-2-(((2-methylpyridin-3-yl)oxy)methyl)morpholine, (R)-2-(((5-chloropyridin-3-yl)oxy)methyl)-4-(2-(indolin-1-yl)ethyl)morpholine, (S)-2-(((5-chloropyridin-3-yl)oxy)methyl)-4-(2-(indolin-1-yl)ethyl)morpholine, (R)-4-(2-(indolin-1-yl)ethyl)-2-(((6-methylpyridin-3-yl)oxy)methyl)morpholine, (S)-4-(2-(indolin-1-yl)ethyl)-2-(((6-methylpyridin-3-yl)oxy)methyl)morpholine, (R)-2-(((2,4-dimethylpyridin-3-yl)oxy)methyl)-4-(2-(indolin-1-yl)ethyl)morpholine,